US008216777B2

(12) United States Patent
Biswal et al.

(10) Patent No.: US 8,216,777 B2

(45) Date of Patent: Jul. 10, 2012

(54) COMPOSITIONS AND METHODS FOR THE TREATMENT OR PREVENTION OF CHEMORESISTANT NEOPLASIA

(75) Inventors: Shyam Biswal, Ellicott City, MD (US); Anju Singh, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 466 days.

(21) Appl. No.: 11/920,907

(22) PCT Filed: May 26, 2006

(86) PCT No.: PCT/US2006/020579

§ 371 (c)(1), (2), (4) Date: Oct. 23, 2009

(87) PCT Pub. No.: WO2006/128041

PCT Pub. Date: Nov. 30, 2006

(65) Prior Publication Data

US 2010/0047368 A1 Feb. 25, 2010

(51) Int. Cl.

| | |
|---|---|
| ***G01N 33/53*** | (2006.01) |
| ***G01N 33/567*** | (2006.01) |
| ***G01N 33/574*** | (2006.01) |
| ***G01N 33/00*** | (2006.01) |
| ***C12Q 1/00*** | (2006.01) |
| ***C12Q 1/68*** | (2006.01) |

(52) U.S. Cl. ........... 435/4; 435/7.1; 435/7.21; 435/7.23; 435/7.9; 435/7.92; 435/6.1; 435/6.14

(58) Field of Classification Search ........................ None
See application file for complete search history.

(56) References Cited

U.S. PATENT DOCUMENTS

| | | | |
|---|---|---|---|
| 2002/0164576 | A1 | 11/2002 | Pedersen et al. |
| 2004/0005579 | A1 | 1/2004 | Birse et al. |
| 2004/0019001 | A1 | 1/2004 | McSwiggen |
| 2004/0219569 | A1 | 11/2004 | Yehiely et al. |
| 2004/0229843 | A1 | 11/2004 | Toole et al. |
| 2007/0042418 | A1 | 2/2007 | Yehiely et al. |
| 2007/0098728 | A1 | 5/2007 | Pedersen et al. |

FOREIGN PATENT DOCUMENTS

| | | |
|---|---|---|
| WO | 0157189 A2 | 8/2001 |
| WO | 0224867 A2 | 3/2002 |

OTHER PUBLICATIONS

Stedman's medical dictionary, 25th ed, 1990, p. 1029-1030.*
Korkola et al, 2005, Oncogene, 24: 5101-5107.*
Montesano, R et al, 1996, Intl J Cancer, 69(3): 225-235.*
Busken, C et al, Digestive Disease Week Abstracts and Itinerary Planner, 2003, abstract No. 850.*
Glinsky et al, 2004, J Clin Invest, 113: 913-923.*
Oesterreich, S et al, 1996 (Clin Cancer Res, 2: 1199-1206.*
Vandesompele J et al, 2003 (Oncogene, 22(3): 456-60).*
Tockman et al (Cancer Res., 1992, 52:2711s-2718s).*
Singh Anju et al: "RNAi-mediated silencing of nuclear factor erythroid-2-related factor 2 gene expression in non-small cell lung cancer inhibitis tumor growth and increases efficacy of chemotherapy." Oct. 1, 2008, Cancer Research, vol. 68, NR. 19, pp. 7975-7984.
Tarumoto Takahisa et al: "Ascorbic acid restores sensitivity to imatinib via suppression of Nrf2-dependent gene expression in the imatinib-resistant cell line" Experimental Hematology, New York, NY, US, vol. 32, No. 4, Apr. 1, 2004, pp. 375-381.
Chen et al. Serial Review: EpRE and its Sigrnaling Pathway Free Radical Biology & Medicine, Apr. 26, 2004, vol. 36. No. 12, pp. 1508-1512.
Timmulappa et al. Identification of Nrf2-regulated Genes induced by the chemopreventative agent sulforaphane by oligonucleotide microarray. Cancer Research. Sep. 2002, vol. 62. pp. 5196-5203.
U.S. Appl. No. 09/499,533, Yehiely et al.
Kotlo et al. "Nrf2 is an inhibitor of the Fas pathway as identified by Achilles' Heel Method, a new function-based approach to gene identification in human cells." Oncogene (2003) 22, 797-806.

* cited by examiner

*Primary Examiner* — Peter J Reddig

(74) *Attorney, Agent, or Firm* — Edwards Wildman Palmer LLP; Peter F. Corless; Melissa Hunter-Ensor, Esq.

(57) ABSTRACT

The invention generally features compositions and methods useful for the treatment and diagnosis of a neoplasia in a subject. In particular, the invention provides therapeutic compositions that decrease the expression of an Nfr2 nucleic acid molecule or polypeptide for the treatment of a neoplasia, such as a chemoresistant neoplasia, in a subject.

4 Claims, 24 Drawing Sheets

| FIG. 1A-1 |
| --- |
| FIG. 1A-2 |
| FIG. 1A-3 |
| FIG. 1A-4 |
| FIG. 1A-5 |

FIG. 8A
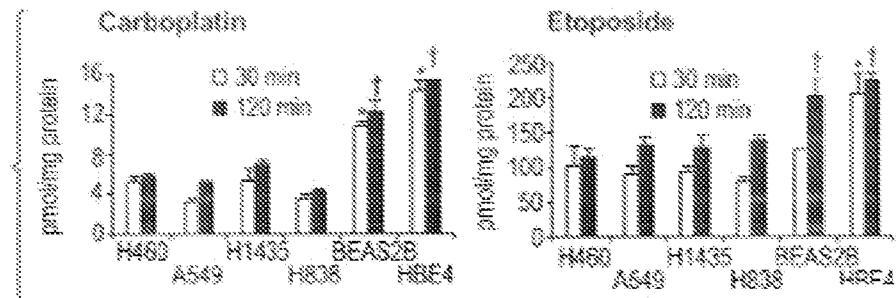
FIG. 8B
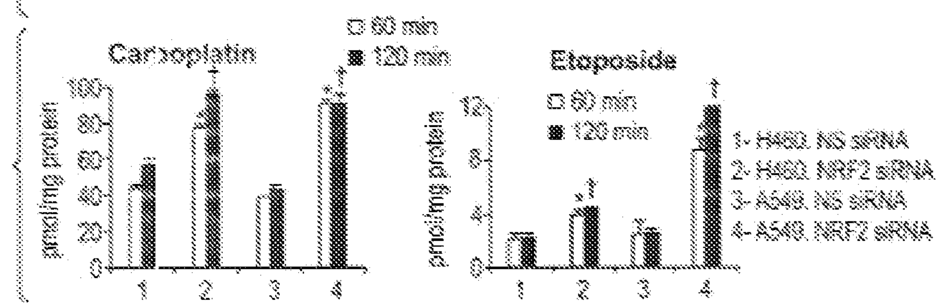
FIG. 8C
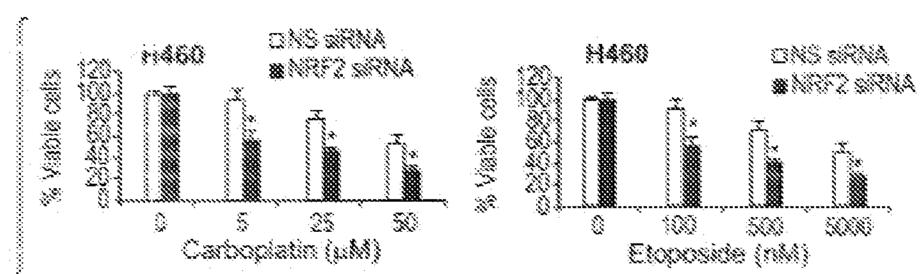
FIG. 8D
A549
NS siRNA
NRF2 siRNA
% Viable cells
Carboplatin (µM)
Etoposide (nM)
FIG. 8E
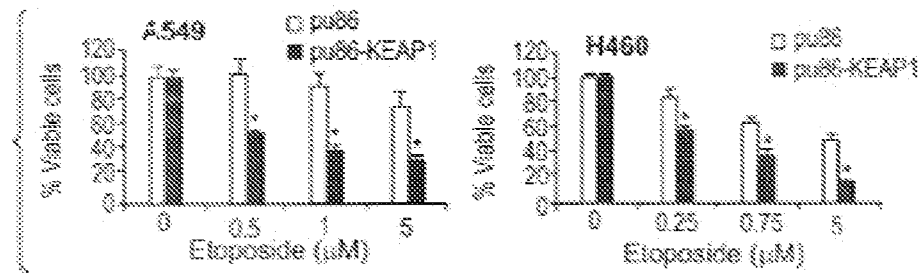

SEQUENCE LISTING

<160> NUMBER OF SEQ ID NOS: 50

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
cuagagcaag auuuagaucu u 21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
guaagaagcc agauguuaau u 21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
augaugucca aagagcaguu u 21

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
uucaucucuu gugagaugag ccucc 25

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5
gaucuaaauc uugcucuagu u 21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
uuaacaucug gcuucuuacu u 21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 7
acugcucuuu ggacaucauu u 21

<210> SEQ ID NO 8
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
ggaggcucau cucacagaga ugaa 24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
actgcatttg gtcttgctcc tc 22

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gcttcttcaa gcatctgaat gtagctgtg 29

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tgaagctgag gcacaggaat a 21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
atgatggaca ctacaccttc atcg 24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gcaaatggat tctgcttcac ctactt 26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tcaaactgtg gagactacac caccat 26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
catcacaatg tacgcggttc ctatta 26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggcacagaat caaaggtcac tgacta 26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gatgaacctg tctctttaag ggggaa 26

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ggagagagag aagcttggac tctatcagaa 30

<210> SEQ ID NO 19

<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gtgagaaggg agaggagaga ggaaaggtct 30

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
tccagctggg caacagagcg agaccttgtt t 31

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aagagactaa ggttttgcta tgttgc 26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
agctgaaact gaaggacaac tgtgtg 26

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ctgcgccccc atgagcgtgc cccttaaccg catc 34

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gatgcggtta aggggcacgc tcatgggggc gcag 34

<210> SEQ ID NO 25
<211> LENGTH: 32
<212> TYPE: DNA

<213> ORGANISM: Artificial Sequence
<220> FEATURE:
<223> OTHER INFORMATION: Description of Artificial Sequence: Synthetic primer

<400> SEQUENCE: 25
gatctacacc gcgggctgct acttccgaca gt 32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
actgtcggaa gtagcagccc gcggtgtaga tc 32

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gtaagaagcc agatgttaat t 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 28
ttaacaucug gcuucuuacu u 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
uagcgacuaa acacaucaau u 21

<210> SEQ ID NO 30
<211> LENGTH: 17
<212> TYPE: DNA
<213> ORGANISM: Homo sapiens

<400> SEQUENCE: 30
tcccgctctg gctcata 17

<210> SEQ ID NO 31
<211> LENGTH: 24
<212> TYPE: DNA
<213> ORGANISM: Homo sapiens

<400> SEQUENCE: 31
cgaagtgccc tggggatcac tgtc 24

<210> SEQ ID NO 32
<211> LENGTH: 17
<212> TYPE: DNA
<213> ORGANISM: Homo sapiens

<400> SEQUENCE: 32
ttctgcagct gcatctg 17

<210> SEQ ID NO 33
<211> LENGTH: 17
<212> TYPE: DNA
<213> ORGANISM: Homo sapiens

<400> SEQUENCE: 33
cgtggtgggc gggctgt 17

<210> SEQ ID NO 34
<211> LENGTH: 17
<212> TYPE: DNA
<213> ORGANISM: Homo sapiens

<400> SEQUENCE: 34
tcccgctctg gctaata 17

<210> SEQ ID NO 35
<211> LENGTH: 15
<212> TYPE: DNA
<213> ORGANISM: Homo sapiens

<400> SEQUENCE: 35
ccggcgagtc cacca 15

<210> SEQ ID NO 36
<211> LENGTH: 17
<212> TYPE: DNA
<213> ORGANISM: Homo sapiens

<400> SEQUENCE: 36
ttctgcagca gcatctg 17

<210> SEQ ID NO 37
<211> LENGTH: 15
<212> TYPE: DNA
<213> ORGANISM: Homo sapiens

<400> SEQUENCE: 37
cgtggtgcgg gctgt 15

<210> SEQ ID NO 38
<211> LENGTH: 17
<212> TYPE: DNA
<213> ORGANISM: Homo sapiens

<400> SEQUENCE: 38
gccgggacca cctgaac 17

<210> SEQ ID NO 39
<211> LENGTH: 17
<212> TYPE: DNA
<213> ORGANISM: Homo sapiens

<400> SEQUENCE: 39
ccgcgggctg ctacttc 17

<210> SEQ ID NO 40
<211> LENGTH: 17
<212> TYPE: DNA
<213> ORGANISM: Homo sapiens

<400> SEQUENCE: 40
cgtgcccctt aaccgca 17

<210> SEQ ID NO 41
<211> LENGTH: 17
<212> TYPE: DNA
<213> ORGANISM: Homo sapiens

<400> SEQUENCE: 41
gccgggacga cctgaac 17

<210> SEQ ID NO 42
<211> LENGTH: 17
<212> TYPE: DNA
<213> ORGANISM: Homo sapiens

<400> SEQUENCE: 42
ccgcgggcgg ctacttc 17

<210> SEQ ID NO 43
<211> LENGTH: 17
<212> TYPE: DNA
<213> ORGANISM: Homo sapiens

<400> SEQUENCE: 43
cgtgccccgt aaccgca 17

<210> SEQ ID NO 44
<211> LENGTH: 16
<212> TYPE: DNA
<213> ORGANISM: Homo sapiens

<400> SEQUENCE: 44
cattggggca ccaagt 16

<210> SEQ ID NO 45
<211> LENGTH: 17
<212> TYPE: DNA
<213> ORGANISM: Homo sapiens

<400> SEQUENCE: 45
tgcagtccga ctcccgc 17

<210> SEQ ID NO 46
<211> LENGTH: 16
<212> TYPE: DNA
<213> ORGANISM: Homo sapiens

<400> SEQUENCE: 46
actggggtca agttcg 16

<210> SEQ ID NO 47
<211> LENGTH: 17
<212> TYPE: DNA
<213> ORGANISM: Homo sapiens -continued

```
<400> SEQUENCE: 47

cattggggcc accaagt                                                    17


<210> SEQ ID NO 48
<211> LENGTH: 17
<212> TYPE: DNA
<213> ORGANISM: Homo sapiens

<400> SEQUENCE: 48

tgcagtccga ctcccgc                                                    17


<210> SEQ ID NO 49
<211> LENGTH: 15
<212> TYPE: DNA
<213> ORGANISM: Homo sapiens

<400> SEQUENCE: 49

actgggtcaa gtacg                                                      15


<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Val Val Pro Pro
1               5
```

COMPOSITIONS AND METHODS FOR THE TREATMENT OR PREVENTION OF CHEMORESISTANT NEOPLASIA

STATEMENT OF RIGHTS TO INVENTIONS MADE UNDER FEDERALLY SPONSORED RESEARCH

This work was supported by the following grants from the National Institutes of Health, Grant Nos: P50CA058184. The government may have certain rights in the invention

CROSS-REFERENCE TO RELATED APPLICATIONS

This application claims priority to U.S. provisional application No. 60/684,928, entitled "Novel Approach for Tracking Cancer Chemoresistance," which was filed on May 26, 2005 and is incorporated herein in its entirety by this reference. The contents of all patents, patent applications, and references cited throughout this specification are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Aug. 25, 2011, is named 65534.txt and is 10,506 bytes in size.

BACKGROUND OF THE INVENTION

The leading cause of death in cancer patients is intrinsic or acquired tumor resistance to chemotherapy. Tumors usually consist of mixed populations of malignant cells, some of which are drug sensitive while others are drug resistant. Chemotherapy that effectively kills drug sensitive cells or sensitizes tumor cells for radiotherapy has little effect on cells that have acquired drug resistance.

Lung carcinomas are the leading cause of cancer deaths in the United States and worldwide in both men and women. Chemotherapy for non-small-cell lung carcinoma (NSCLC), which accounts for approximately 85% of lung cancer cases, remains marginally effective. The major contributing factor to the failure of chemotherapy in lung cancer is the development of drug resistance.

Cancer cells have higher expression of Phase II enzymes and Phase III drug efflux proteins, both of which detoxify drugs. Phase II enzymes include the family of glutathione S-transferase enzymes, glutathione biosynthetic genes, UDP-glucoronosyltransferases (UGT), members of the aldo keto reductase superfamily, and several antioxidants that are involved in the detoxification of a broad spectrum of anti-cancer drugs. The multidrug resistance (MDR) proteins are ATP binding cassette transporters, and belong to the Phase III drug efflux class of proteins. The MDR proteins act as molecular pumps in the tumor cell membrane, actively expelling chemotherapy drugs from the interior of the cell, and allowing the tumor cell to subvert the chemotherapeutic effects of the administered compounds. Several studies have shown that the expression of Phase II genes [glutathione-S-transferases (GSTs)], antioxidants [glutathione (GSH)], and drug efflux proteins [multidrug resistance protein (MRP) family] are increased in NSCLC. Phase II detoxification enzymes in conjunction with Phase III drug efflux proteins act to detoxify cancer drugs, whereas antioxidants confer cyto-protection by attenuating drug-induced oxidative stress and apoptosis.

Presently, chemoresistance presents an obstacle to the treatment of cancer, and treatment options for subjects with multi drug resistant tumors are limited. Thus, there is an urgent need for methods of identifying and treating chemoresistant tumors.

SUMMARY OF THE INVENTION

As described below, the present invention features compositions and methods for the diagnosis, treatment, or prevention of a neoplasia (e.g., a chemoresistant neoplasia).

In general, the present invention provides for compositions and methods useful for the treatment and diagnosis of a neoplasia in a subject. In particular, the invention provides therapeutic compositions that decrease the expression of an Nfr2 nucleic acid molecule or polypeptide for the treatment of a neoplasia, such as a chemoresistant neoplasia, in a subject.

In one aspect, the invention generally features an inhibitory nucleic acid molecule that corresponds to or is complementary to at least a fragment of a Nrf2 nucleic acid molecule, and that decreases Nrf2 expression in a cell. In one embodiment, the inhibitory nucleic acid molecule is double-stranded. In another embodiment, the inhibitory nucleic acid molecule is single stranded. In yet another embodiment, the single stranded inhibitory nucleic acid molecule is an antisense nucleic acid molecule.

In another aspect, the invention features a double-stranded inhibitory nucleic acid molecule that corresponds to or is complementary to at least a fragment of a Nrf2 nucleic acid molecule that decreases Nrf2 expression in a cell. In a particular embodiment of the above aspect, the double-stranded nucleic acid molecule is an siRNA. In a related embodiment, the double-stranded nucleic acid molecule is an shRNA. In yet another embodiment, the double-stranded nucleic acid molecule is about 19-21 nucleotides in length. In an embodiment of the above aspect, the double-stranded nucleic acid molecule includes any one or more of the following nucleic acid sequences: SEQ ID NO: 1/ND1, SEQ ID NO: 2/ND3, SEQ ID NO: 3/ND4, and SEQ ID NO: 4/ND5. In a related embodiment of the above aspects, the nucleotide sequence comprises at least one modified linkage. In another embodiment, the inhibitory nucleic acid molecule comprises a modified backbone. In yet another embodiment, the modified backbone comprises a phosphorothioate or phosphorodithioate modification.

In another aspect, the invention features a vector encoding an inhibitory nucleic acid molecule of any of the above aspects. In a particular embodiment, the vector is a retroviral, adenoviral, adeno-associated viral, or lentiviral vector. In another embodiment, the vector contains a promoter suitable for expression in a mammalian cell. Another embodiment features a cell containing the vector of the above aspect, or an inhibitory nucleic acid molecule of any one of the above aspects. In a further embodiment of the aspect, the cell is a neoplastic cell in vivo.

In another aspect, the invention features a method of decreasing Nrf2 expression in a cell, the method involving contacting the cell with an effective amount of an inhibitory nucleic acid molecule corresponding to or complementary to at least a portion of a Nrf2 nucleic acid molecule, where the inhibitory nucleic acid molecule inhibits expression of a Nrf2 polypeptide, thereby decreasing Nrf2 expression in the cell. In a particular embodiment of the above aspect, the inhibitory nucleic acid molecule is an antisense nucleic acid molecule, a small interfering RNA (siRNA), or a double-stranded RNA (dsRNA). In a further embodiment of the method, the inhibitory nucleic acid molecule includes any one or more of the following nucleic acid sequences: SEQ ID NO: 1/ND1, SEQ ID NO: 2/ND3, SEQ ID NO: 3/ND4, and SEQ ID NO: 4/ND5, and SEQ ID NO: 5/ND5. SEQ ID NO: 1/ND1, SEQ ID NO: 2/ND3, SEQ ID NO: 3/ND4, and SEQ ID NO: 4/ND5. In another embodiment, the method decreases Nrf2 transcription or translation.

In yet another aspect, the invention features a method of increasing apoptosis in a neoplastic cell, the method involving contacting the cell with an effective amount of an inhibitory nucleic acid molecule of any one of claims 1-12, thereby increasing apoptosis in the cell. In a particular embodiment of the aspect, the cell is a human cell, a neoplastic cell, a cell that is in vivo or in vitro 23. In another embodiment, the method involves contacting the cell with an effective amount of a chemotherapeutic agent.

In yet another aspect, the invention features a method of treating a subject having a neoplasm, the method involving administering to the subject an effective amount of an inhibitory nucleic acid molecule corresponding to or complementary to a Nrf2 nucleic acid molecule, where the inhibitory nucleic acid molecule reduces Nrf2 expression thereby treating the neoplasm. In an embodiment of the above aspect, the method involves administering to the subject a chemotherapeutic agent. In a particular embodiment of the above aspect, the method decreases the size of the neoplasm relative to the size of the neoplasm prior to treatment. In another embodiment of the above aspect, administration of the inhibitory nucleic acid molecule decreases drug resistance of the neoplasm. In a particular embodiment, the inhibitory nucleic acid molecule is an antisense nucleic acid molecule, a small interfering RNA (siRNA), or a double-stranded RNA (dsRNA). In yet another embodiment of the method, the inhibitory nucleic acid molecule includes a nucleic acid sequence selected from the group that includes any one or more of the following nucleic acid sequences: SEQ ID NO: 1/ND1, SEQ ID NO: 2/ND3, SEQ ID NO: 3/ND4, and SEQ ID NO: 4/ND5. In a further embodiment of the method, the inhibitory nucleic acid molecule is delivered in a liposome, polymer, microsphere, gene therapy vector, or naked DNA vector. In a particular embodiment, the neoplasm is sensitized for effective radiotherapy.

In a further aspect, the invention features a method of treating a subject, (e.g. a human patient) having a neoplasm, the method involving administering to the subject an effective amount of an inhibitory nucleic acid molecule and a chemotherapeutic agent simultaneously or within 14 days of each other in amounts sufficient to inhibit the growth of the neoplasm. In one embodiment of the aspect, the inhibitory nucleic acid molecule and the chemotherapeutic agent are administered simultaneously or within 1, 3, 5, 7, 10, 14, 21, 28, 45 or 60 days of each other in amounts sufficient to inhibit the growth of the neoplasm. In another embodiment of the method, the chemotherapeutic agent is any one or more of cisplatin, etoposide, and carboplatin. In a particular embodiment of the above method, the inhibitory nucleic acid molecule is an antisense nucleic acid molecule, a small interfering RNA (siRNA), or a double-stranded RNA (dsRNA) that inhibits expression of a Nrf2 polypeptide. In yet another embodiment of the method, the inhibitory nucleic acid molecule includes a nucleic acid sequence selected from the group that includes any one or more of the following nucleic acid sequences: SEQ ID NO: 1/ND1, SEQ ID NO: 2/ND3, SEQ ID NO: 3/ND4, and SEQ ID NO: 4/ND5. In a further embodiment of the above aspects, a cell of the neoplasm overexpresses Nrf2. In another embodiment, the neoplasm is cancer, (e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. In a particular embodiment, the cancer is lung cancer. In another particular embodiment, the cancer is kidney cancer). In a further embodiment of the above aspects, the method involves identifying the subject as having a neoplasm.

In another aspect, the invention features a method of treating or preventing chemoresistance in a subject, (e.g. a human patient), having a neoplasm, the method involving administering to the subject an effective amount of an inhibitory nucleic acid molecule that corresponds to or is complementary to at least a fragment of a Nrf2 nucleic acid molecule, and that decreases Nrf2 expression thereby treating or preventing chemoresistance.

In one embodiment of the above method, the inhibitory nucleic acid molecule containing any one or more of the following: SEQ ID NO: 1/ND1, SEQ ID NO: 2/ND3, SEQ ID NO: 3/ND4, and SEQ ID NO: 4/ND5. In a further embodiment, the method involves administering a chemotherapeutic agent. In a particular embodiment, the inhibitory nucleic acid molecule is administered at a dosage of about 5 to 500 $mg/m^2$/day (e.g., 5, 25, 50, 100, 125, 150, 175, 200, 225, 250, 275, 300 $mg/m^2$/day). In another particular embodiment of the method, the chemotherapeutic agent is selected from the group that includes any one or more of the following: cisplatin, etoposide, and carboplatin. In still a further embodiment of the method, the neoplasm is cancer, (e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer). In one embodiment, the cancer is lung cancer. In a further embodiment, the cancer is kidney cancer. A further related embodiment of the method involves identifying the subject as being in need of a treatment or prevention of chemoresistance.

In yet another aspect, the invention describes a method of identifying an agent that inhibits chemoresistance, the method involving contacting a cell that expresses Nrf2 nucleic acid molecule with an agent, and then comparing the level of Nrf2 nucleic acid molecule or polypeptide expression in the cell contacted by the agent with the level of expression in a control cell, where an agent that decreases Nrf2 expression thereby inhibits chemoresistance. In one embodiment of the method, the decrease in expression is a decrease in transcription or translation.

In another aspect, the invention features a pharmaceutical composition for decreasing chemoresistance in a subject involving a therapeutically effective amount of an inhibitory nucleic acid molecule that corresponds to or is complementary to at least a fragment of a Nrf2 nucleic acid molecule in a pharmaceutically acceptable excipient. In one embodiment of the aspect, the amount of the inhibitory nucleic acid molecule is from about 100 to about 300 $mg/m^2$/day.

In a further aspect, the invention features a pharmaceutical composition for treating a neoplasm in a subject involving a therapeutically effective amount of an inhibitory nucleic acid molecule that corresponds to or is complementary to at least a fragment of a Nrf2 nucleic acid molecule and a chemotherapeutic agent in a pharmaceutically acceptable excipient. In a particular embodiment of the aspect, the chemotherapeutic agent is selected from the group consisting of: cisplatin, etoposide, and carboplatin.

In another aspect, the invention features a method for diagnosing a subject as having or having a propensity to develop chemoresistance, the method involving measuring markers in a biological sample from a patient at risk for developing chemoresistance and detecting an alteration in the expression of test marker molecules relative to the sequence or expression of a reference molecule, where the markers are selected from the group consisting of: Nrf2, Keap1, GSH, GST, and NQO1.

In yet another aspect, the invention features a method for diagnosing a subject as having or having a propensity to develop a neoplasia, the method involving measuring the level of a Nrf2, Keap1, GSH, GST, or NQO1 nucleic acid molecule or polypeptide marker in a biological sample from the subject, and detecting an alteration in the level of the marker in the sample relative to the level in a control sample, where detection of an alteration in the marker level indicates the subject has or has a propensity to develop a neoplasia. In one embodiment of the above method, the level of expression is determined in an immunological assay. In another embodiment of the method, the level of expression is determined in a microchip assay. In a further embodiment, the method involves measuring the level of Nrf2, Keap1, GSH, GST, and NQO1 nucleic acid molecule or polypeptide markers.

In another aspect, the invention features a method of diagnosing a subject as having, or having a propensity to develop, a neoplasia, the method involving identifying a mutation in Keap1 gene present in a biological sample from the subject, where the mutation indicates that the subject has or has a propensity to develop a neoplasia.

In another aspect, the invention features a method of diagnosing a subject as having, or having a propensity to develop a chemoresistant neoplasia, the method involving identifying a mutation in Keap1 gene present in a biological sample from the subject, where the mutation indicates that the subject has or has a propensity to develop a chemoresistant neoplasia. In various embodiments of the above aspects, the mutation is a deletion, insertion, missense or frameshift. In other embodiments, the mutation in the Keap1 gene is a loss of heterozygozity. In yet another embodiment the loss of heterozygosity is detected with microsatellite markers. In a further embodiment, the microsatellite markers comprise KEAP-UM1 and KEAP-DM1.

In another aspect, the invention features a kit for the diagnosis of a neoplasia in a subject, the kit containing any one or more of the following nucleic acid molecules: Nrf2, Keap 1, GSH, GST, NQO1, or probes for detecting these molecules, and written instructions for use of the kit for detection of a neoplasia in a biological sample.

In a further aspect, the invention features a diagnostic kit for the diagnosis of chemoresistance in a subject, the kit containing any one or more of the following nucleic acid molecules: Nrf2, Keap1, GSH, GST, NQO1, or probes for detecting these molecules, and written instructions for use of the kit for the detection of chemoresistance.

In yet another aspect, the invention features a method of identifying an agent that inhibits neoplasia or chemoresistance, the method involving contacting a cell that expresses a Nrf2 polypeptide or nucleic acid molecule with the agent; and comparing the level of expression of the Nrf2 polypeptide or nucleic acid molecule in the cell contacted by the candidate compound with the level of Nrf2 polypeptide or nucleic acid molecule expression in a control cell, where a decrease in the expression of the Nrf2 polypeptide or nucleic acid molecule thereby identifies the agent as inhibiting chemoresistance.

In a further aspect, the invention features a method of identifying an agent that inhibits a neoplasia or chemoresistance, the method involving contacting a cell that expresses a Nrf2 polypeptide with an agent; and comparing the biological activity of the polypeptide in the cell contacted by the agent with the level of biological activity in a control cell not contacted by the agent, where a decrease in the biological activity of the Nrf2 polypeptide thereby identifies the agent as inhibiting a neoplasia or chemoresistance. In a particular embodiment of the above method, the cell is a human cell, a neoplastic cell, or a cell that is in vivo or in vitro.

In another aspect, the invention features a method of identifying an agent that inhibits a neoplasia, the method involving contacting a cell containing a Nrf2 nucleic acid molecule present in an expression vector that includes a reporter construct; detecting the level of reporter gene expression in the cell contacted with the candidate compound with a control cell not contacted with the candidate compound, where an alteration in the level of the reporter gene expression identifies the candidate compound as a candidate compound that inhibits a neoplasia.

In yet another aspect, the invention features a method of identifying a therapeutic regimen for a subject having a neoplasia, the method involving measuring the level of a Nrf2, Keap1, GSH, GST, or NQO1 nucleic acid molecule or polypeptide marker in a biological sample from the subject; and detecting an alteration in the level of the marker in the sample relative to the level in a control sample, where detection of the alteration in the marker level identifies a therapeutic regiment for treatment of the neoplasm in the subject. In one embodiment of the above method, the method identifies a chemoresistant neoplasia that requires aggressive chemotherapy. In another embodiment of the method, the treatment regimen includes a Nrf2 inhibitory nucleic acid molecule and a chemotherapeutic. In yet another embodiment, the above method identifies a neoplasia that is susceptible to treatment with convention chemotherapy.

In another aspect, the invention features a packaged pharmaceutical containing a therapeutically effective amount of an inhibitory nucleic acid molecule corresponding or complementary to at least a fragment of a Nrf2 nucleic acid molecule, that decreases Nrf2 expression in a cell, and instructions for use in treating a subject having a neoplasm. In a particular embodiment, the packaged pharmaceutical further involves a chemotherapeutic agent.

In yet another aspect, the invention features a packaged pharmaceutical containing a therapeutically effective amount of an inhibitory nucleic acid molecule corresponding or complementary to at least a fragment of a Nrf2 nucleic acid molecule, that decreases Nrf2 expression in a cell, and instructions for use in treating or preventing chemoresistance in a subject.

In another aspect, the invention features the methods of the above named aspects, further involving obtaining the inhibitory nucleic acid molecule.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Nrf2 polypeptide" is meant a protein or protein variant, or fragment thereof, that is substantially identical to at least a portion of GenBank Accession No. NP_006164 (human nuclear factor (erythroid-derived 2)-like 2) and that has a Nrf2 biological activity (e.g., activation of target genes through binding to antioxidant response element (ARE), regulation of expression of antioxidants and xenobiotic metabolism genes).

By "Nrf2 nucleic acid molecule" is meant a polynucleotide encoding an Nrf2 polypeptide or variant, or fragment thereof.

The phrase "in combination with" is intended to refer to all forms of administration that provide the inhibitory nucleic acid molecule and the chemotherapeutic agent together, and can include sequential administration, in any order.

The term "subject" is intended to include vertebrates, preferably a mammal. Mammals include, but are not limited to, humans.

By "marker" is meant any protein or polynucleotide having an alteration in expression level or activity that is associated with a disease or disorder.

The term "drug resistance" as used herein is defined as a cell's increasing resistance to drug therapy, such as chemotherapy.

The term "loss of heterozygozity" is intended to mean the loss of one allele at a specific locus, caused by a deletion; or loss of a chromosome from a chromosome pair, resulting in abnormal hemizygosity.

The term "microsattelite marker" refers to PCR primers that are unique to one locus in the genome and that base pair on either side of the locus; the markers are used to detect microsatellites, sometimes referred to as a variable number of tandem repeats or VNTRs, short segments of DNA that have a repeated sequence.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibitory nucleic acid" is meant a single or double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises or corresponds to at least a portion of a target nucleic acid molecule, or an ortholog thereof, or comprises at least a portion of the complementary strand of a target nucleic acid molecule.

By "antisense nucleic acid", it is meant a non-enzymatic nucleic acid molecule that binds to target RNA by means of RNA-RNA or RNA-DNA interactions and alters the activity of the target RNA (for a review, see Stein et al. 1993; Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk N A et al., 1999; Delihas N et al., 1997; Aboul-Fadl T, 2005.)

By "small molecule" inhibitor is meant a molecule of less than about 3,000 daltons having Nrf2 antagonist activity.

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

By "corresponds to an Nrf2 gene" is meant comprising at least a fragment of the double-stranded gene, such that each strand of the double-stranded inhibitory nucleic acid molecule is capable of binding to the complementary strand of the target Nrf2 gene.

The term "microarray" is meant to include a collection of nucleic acid molecules or polypeptides from one or more organisms arranged on a solid support (for example, a chip, plate, or bead).

By "neoplasia" is meant any disease that is caused by or results in inappropriately high levels of cell division, inappropriately low levels of apoptosis, or both. For example, cancer is an example of a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioepdotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant protein of the invention, or an RNA molecule).

By "reference" is meant a standard or control condition.

The term "pharmaceutically-acceptable excipient" as used herein means one or more compatible solid or liquid filler, diluents or encapsulating substances that are suitable for administration into a human.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "transformed cell" is meant a cell into which (or into an ancestor of which) has been introduced, by means of recombinant DNA techniques, a polynucleotide molecule encoding (as used herein) a protein of the invention.

BRIEF DESCRIPTION OF THE DRAWINGS

FIGS. 1A-1D describe somatic alterations in the KEAP1 nucleic acid sequence that occur in lung cancer. FIGS. 1A-1 to 1A-5 shows loss of heterozygosity (LOH) at the 19p13.1-13.3 chromosomal region. The heatmap shown depicts microsatellite-based LOH at 19p13.1-19p13.3 in 181 lung cancer cell lines. Retained alleles are depicted in dark grey. Single nucleotide polymorphisms (SNPs) demonstrating allelic loss are shown in light grey. Non-informative markers are shown in black. The following abbreviations are used in FIGS. 1A-1 to 1A-5: SCC, Small cell carcinoma; ET, Endocrine tumors; NS, No subtype specified. FIG. 1B shows a sequence analysis of KEAP1 mutations in lung cancer. FIG. 1B, column (a) identifies a mutation in an H838 cell line that has a C-A substitution (G-T, Plus strand) that results in a termination codon. The wild-type (WT) sequence is from BEAS2B. A wild-type allele was not detected in the H838 cell line. FIG. 1B, column (b) identifies an 18 base pair deletion that was detected in one allele, but not in the other allele, in the pleural fluid (PF) DNA sample from the PF-8. FIG. 1B, column (c) characterizes a mutation in lung tumor PT-23 showing an A-T substitution in one allele, but not in the other allele. FIG. 1B, column (d) characterizes a 2-base pair deletion in the 4th exon of KEAP1 that was detected in one allele of a primary tumor PT-17. Samples showing deletion mutations were further confirmed by subcloning and sequencing. FIG. 1C shows the results of sequence analysis. The top panels show representative DNA sequence data from three lung cancer cell lines: H460, A549 and H1435. The bottom panels are WT sequences from non-malignant cell line, BEAS2B. Sequence analysis revealed mutations in KEAP1 in lung cancer cell lines and tumor tissues. Only the mutant allele was detected in the H460, A549 and H1435 cancer cell lines. FIG. 1D shows representative electropherograms depicting some of the KEAP1 mutations identified in NSCLC tumor tissues. All the mutations identified in patients were heterozygous.

FIG. 2A is a schematic diagram that summarizes LOH patterns of 39 lung tumors. Retained microsattelites are indicated in dark grey, markers demonstrating allelic loss are indicated in light grey, markers showing genomic instability are indicated in dark grey with 'x' markings, and non-informative markers are indicated in black. FIG. 2B includes four representative electropherograms showing partial and complete loss of one allele and microsatellite instability at chromosomal locus 19p13.2.

FIG. 3A is a series of four micrographs showing the results of an immunohistochemical analysis of NRF2 in NSCLC tissues. FIG. 3A(a) shows NRF2 staining in a sample obtained from a patient (PT-18) with a mutation in KEAP1. This sample shows strong nuclear and cytoplasmic staining. FIG. 3A(b) shows NRF2 staining in a tissue sample obtained from a patient (PT-28) that does not have a mutation in NRF2. This sample shows only weak cytoplasmic staining. FIG. 3A(c) shows NRF2 staining in a sample obtained from a patient that does not have an NRF2 mutation (PT-20) showing increased nuclear and cytoplasmic staining in tumor tissue. FIG. 3A (d) shows that normal bronchus from the same patient have only weak NRF2 staining (PT-20). FIG. 3B is a heat map that depicts total glutathione (GSH) and enzyme activities of NAD(P)H dehydrogenase, quinone 1 (NQO1) and total glutathione-S-transferases (GST) in matched NSCLC and normal tissues. Symbols as indicated in the figure legends are as follows: *nmol/mg protein; .dagger., nmol DCPIP reduced/min/mg protein; .dagger-dbl., nmol of product formed/min/mg protein. FIG. 3C depicts an immunoblot analysis showing increased nuclear localization of NRF2 in nuclear extracts (NE) from cancer cells. Cell lines used are listed above the lanes. Cancer cells showed lower levels of KEAP1 and higher NRF2 in total protein (TP) lysates. NIVT, KIVT: NRF2 or KEAP1 in vitro transcribed/translated product, respectively. FIG. 3D is a heat map showing relative expression of KEAP1, NRF2 and NRF2-dependent genes by real time RT-PCR. FIG. 3E is a graph illustrating the effect of NRF2 siRNA on NRF2 activity. The graph shows that silencing of NRF2 by siRNA down-regulated the expression of its target genes. A non-specific siRNA (NS siRNA) was used as control. FIG. 3F is a graph showing the quantitation of normalized NRF2 levels for the heat map provided at FIG. 3D. FIG. 3G is a graph showing the quantitation of normalized total NRF2 and total KEAP1 levels for the heat map provided at FIG. 3D.

FIGS. 4A-D are graphs showing Nrf2 dependent enzyme activities in cancer cells and normal cells. FIG. 4A shows total GSH levels in cancer cells and normal cells. FIG. 4B shows total GST activity in cancer cells and normal cells. FIGS. 4C and 4D are graphs that compare NQO1 and glutathione reductase 1 (GSR) activity in cancer and normal cell lines. The data represent mean plus or minus the standard deviation, with a sample size, n=3. Symbols on the graphs correspond as follows: *, p, 0.005; **, p, 0.05, relative to normal cells as determined by the t-test.

FIG. 5 is a graph showing repression activity of the KEAP1 mutants as monitored by a luciferase assay. Wild type and mutant KEAP1 cDNA constructs were transfected into cells stably transfected with an ARE luciferase reporter plasmids. L413R refers to Leucine to Arginine mutation found in H1435 cell line and G333C refers to Glycine to serine substitution found in A549 cell line. The data represent the mean, plus or minus the standard deviation, with a sample size n=3.

FIGS. 8A-8E are graphs showing carboplatin and etoposide accumulation in cancer cells and normal cells at thirty and one hundred-twenty minutes following drug administration. FIG. 8A is a graph showing the drug accumulation profile of normal and cancer cells. In the graph, the symbol "*" represents $P<0.05$, relative to cancer cells at 30 minutes and 120 minutes, respectively. FIG. 8B shows accumulation of $^{14}C$ labeled carboplatin and $^{3}H$ labeled etoposide in A549 and H460 cells transfected with NRF2 siRNA. A non-targeting NS siRNA was used as control. In the graph, the symbol "*" represents $P<0.001$, relative to NS siRNA at 60 minutes and 120 minutes. FIG. 8C is a graph depicting enhanced sensitivity of NRF2 siRNA transfected A549 and H460 cells to etoposide and carboplatin. Cells were exposed to drugs for 96 hours and viable cells were determined using the MTT [3-(4,5-dimethylthiazol-2-yl)-2,5-diphenyltetrazolium bromide] assay, as described in the methods section. Data is represented as the percentage of viable cells relative to vehicle treated control. The Data represent the mean of 6 independent replicates, combined to generate the mean plus or minus the standard deviation for each concentration. The symbol "*" represents $P<0.001$ relative to control NS siRNA. FIG. 8D and FIG. 8E are graphs showing increased sensitivity of A549 and H460 cells over-expressing pUb6-KEAP1 (WT-KEAP1) to etoposide, when compared to control cells expressing an empty vector. Expression of Wild type KEAP1 enhanced the drug sensitivity of A549 and H460 cells. The symbol * represents $P<0.001$ relative to vector control. All experiments were repeated three times with similar results. Significance was determined using paired t test.

FIG. 9A is a graph depicting dose response of cells treated with cisplatin, Nrf2 siRNA, or a combination of both after 24 hours. FIG. 9B is a graph depicting dose response of cells treated with cisplatin, Nrf2 siRNA, or a combination of both after 48 hours. Percent survival is indicated on the Y-axis, as quantified from cell proliferation measured using the MTT assay as described in the materials and methods.

FIG. 12A shows the total tumor weight and FIG. 12B shows the total volume of the primary tumor in the kidney measured four weeks after injection.

DETAILED DESCRIPTION OF THE INVENTION

Figures 1, 1A:
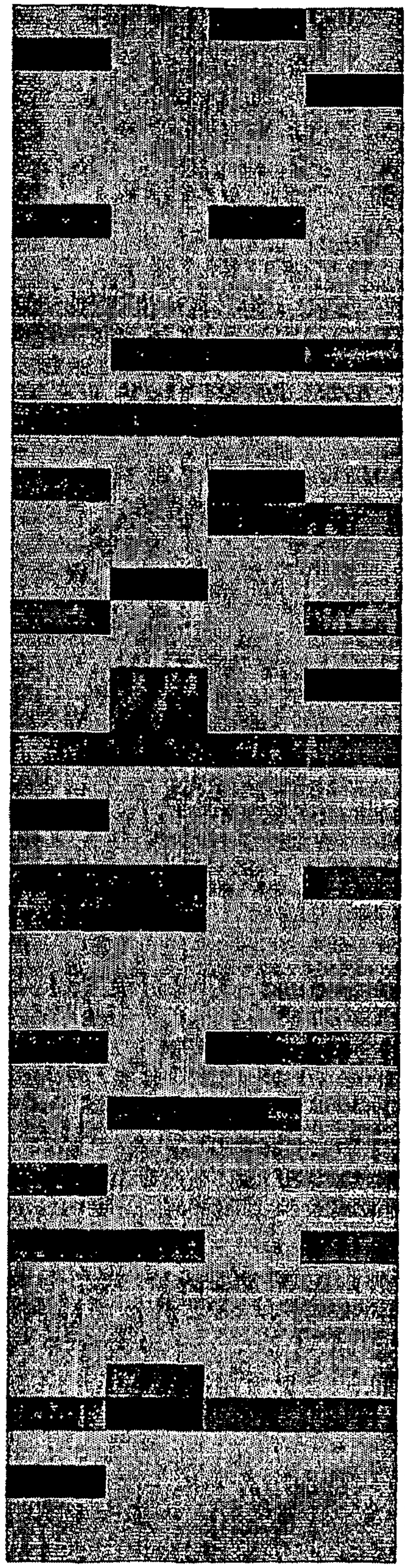
Figures 1, 1A, 2:
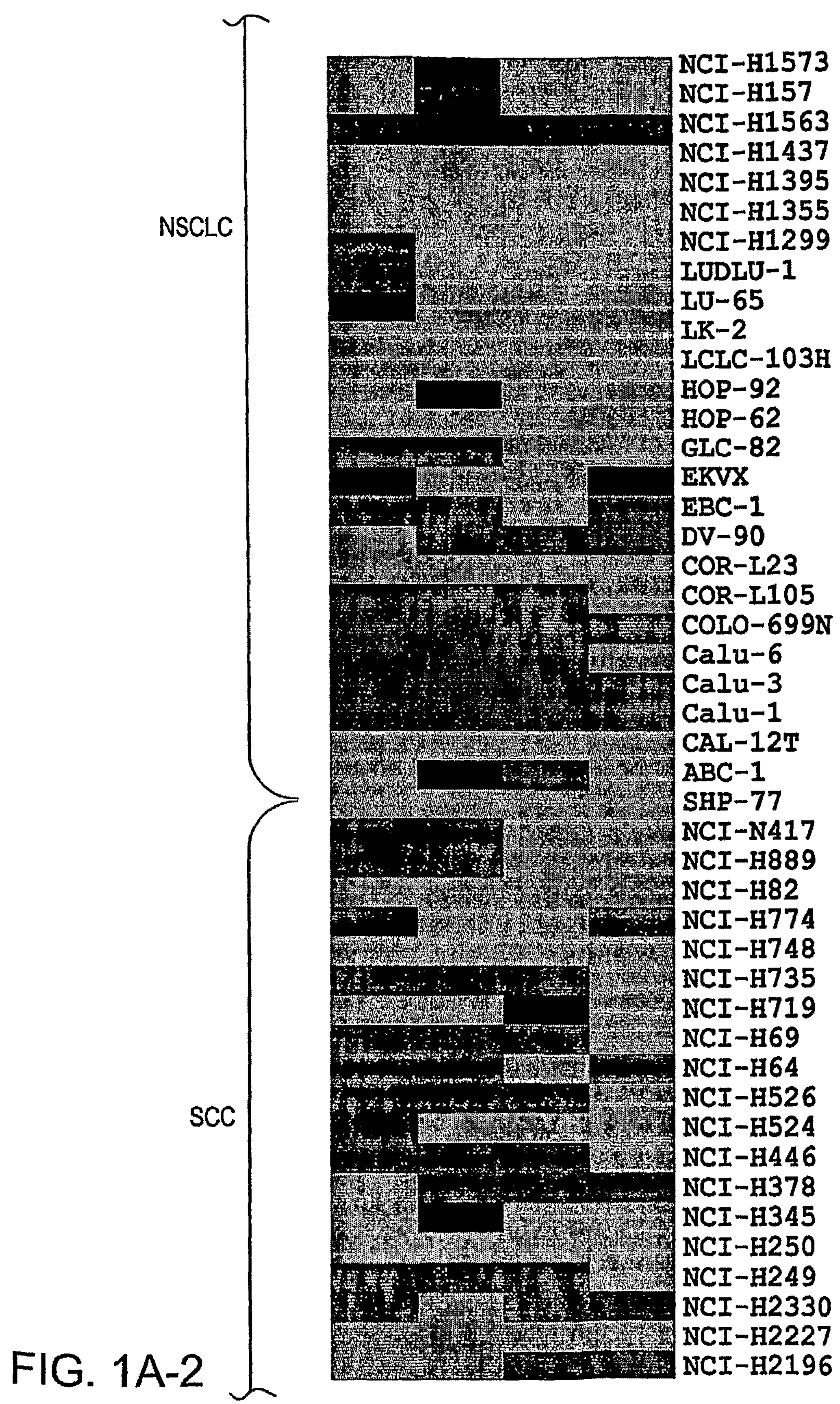
Figures 1, 1A, 2, 3:
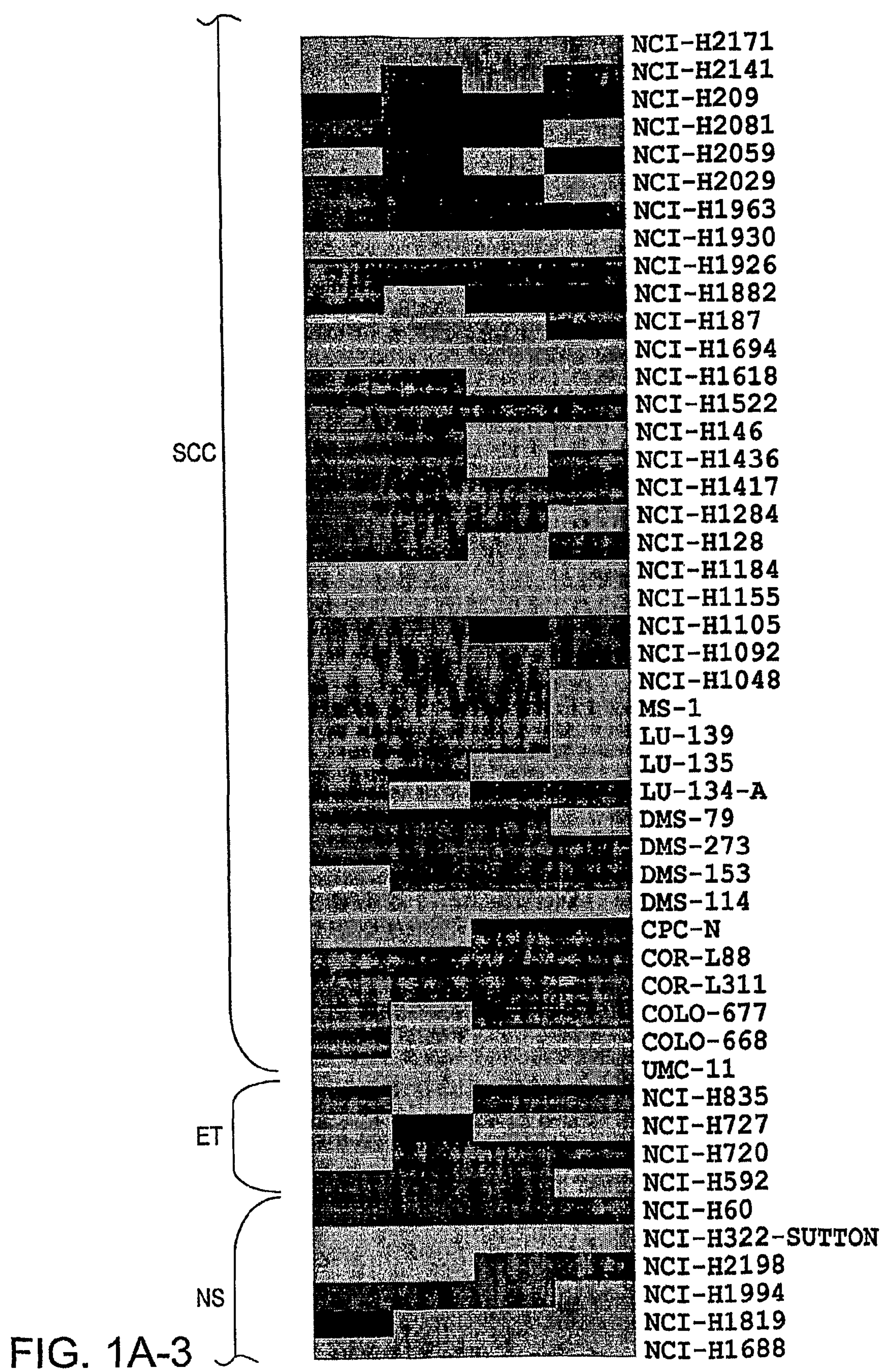
Figures 1, 1A, 2, 3, 4:
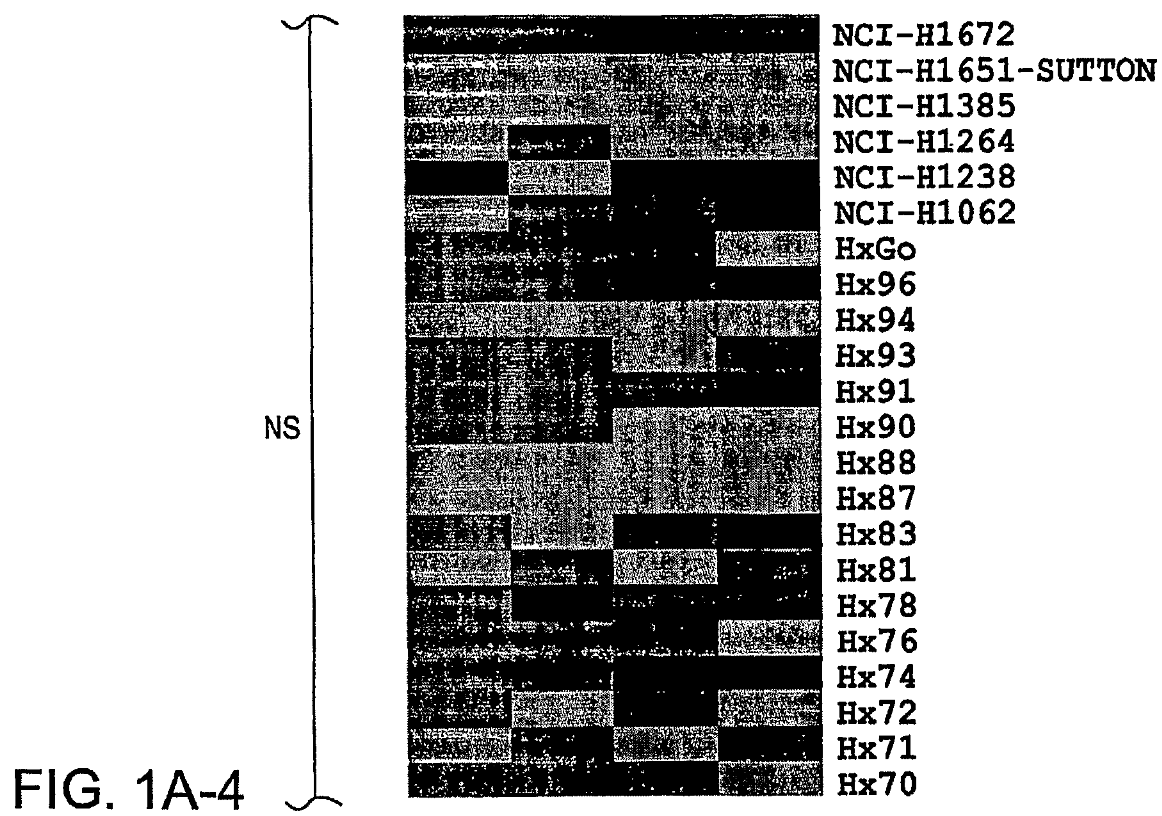

The invention generally features compositions and methods useful for the treatment and diagnosis of a neoplasia in a subject. In particular, the invention provides therapeutic compositions (e.g., inhibitory nucleic acid molecules, such as siRNAs, antisense RNAs, and shRNAs) that decrease the expression of an Nfr2 nucleic acid molecule or polypeptide for the treatment of a neoplasia in a subject.

Nuclear Factor E2p45-Related Factor (Nrf2)

Nuclear factor erythroid-2 related factor 2 (NRF2), a cap-and-collar basic leucine zipper transcription factor, regulates a transcriptional program that maintains cellular redox homeostasis and protects cells from oxidative insult, including from chemotherapeutic agents (Rangasamy T, et al., *J Clin Invest* 114, 1248 (2004); Thimmulappa R K, et al. *Cancer Res* 62, 5196 (2002); So H S, et al. *Cell Death Differ* (2006)). NRF2 activates transcription of its target genes through binding specifically to the antioxidant-response element (ARE) found in those gene promoters. The NRF2-regulated transcriptional program includes a broad spectrum of genes, including antioxidants [γ-glutamyl cysteine synthetase modifier subunit (GCLm), γ-glutamyl cysteine synthetase catalytic subunit (GCLc), heme oxygenase-1, superoxide dismutase, glutathione reductase (GSR), glutathione peroxidase, thioredoxin, thioredoxin reductase, peroxiredoxins (PRDX), cysteine/glutamate transporter (SLC7A11) (7, 8)], phase II detoxification enzymes [NADP(H) quinone oxidoreductase 1 (NQO1), GST, UDP-glucuronosyltransferase (Rangasamy T, et al. *J Clin Invest* 114: 1248 (2004); Thimmulappa R K, et al. *Cancer Res* 62: 5196 (2002)), and several ATP-dependent drug efflux pumps, including MRP1, MRP2 (Hayashi A, et al. *Biochem Biophy Res Commun* 310: 824 (2003)); Vollrath V, et al. *Biochem J* (2006)); Nguyen T, et al. *Annu Rev Pharmacol Toxicol* 43: 233 (2003)).

KEAP1

KEAP1 is a cytoplasmic anchor of NRF2 that also functions as a substrate adaptor protein for a Cul3-dependent E3 ubiquitin ligase complex to maintain steady-state levels of NRF2 and NRF2-dependent transcription A. Kobayashi et al., *Mol Cell Biol* 24: 7130 (2004); Zhang D D et al. *Mol Cell Biol* 24: 10491 (2004)). The Keap1 gene is located at human chromosomal locus 19p13.2. The KEAP1 polypeptide has three major domains: (1) an N-terminal Broad complex, Tramtrack, and Bric-a-brac (BTB) domain; (2) a central intervening region (IVR); and (3) a series of six C-terminal Kelch repeats (Adams J, et al. *Trends Cell Biol* 10:17 (2000). The Kelch repeats of KEAP1 bind the Neh2 domain of NRF2, whereas the IVR and BTB domains are required for the redox-sensitive regulation of NRF2 through a series of reactive cysteines present throughout this region (Wakabayashi N, et al. *Proc Natl Acad Sci USA* 101: 2040 (2004)). KEAP1 constitutively suppresses NRF2 activity in the absence of stress. Oxidants, xenobiotics and electrophiles hamper KEAP1-mediated proteasomal degradation of NRF2, which results in increased nuclear accumulation and, in turn, the transcriptional induction of target genes that ensure cell survival (Wakabayashi N, et al. *Nat Genet.* 35: 238 (2003)). Germline deletion of the KEAP1 gene in mice results in constitutive activation of NRF2 (Wakabayashi N, et al *Nat Genet.* 35: 238 (2003)). Recently, a somatic mutation (G430C) in KEAP1 in one lung cancer patient and a small-cell lung cancer cell line (G364C) have been described (Padmanabhan B, et al. *Mol Cell* 21: 689 (2006)). Prothymosin α, a novel binding partner of KEAP1, has been shown to be an intranuclear dissociator of NRF2-KEAP1 complex and can upregulate the expression of Nrf2 target genes (Karapetian R N, et al. *Mol Cell Biol* 25: 1089 (2005)).

As reported in more detail below, KEAP1 activity was inappropriately regulated in non-small-cell lung cancer (NSCLC) tumors due to mutations and loss of heterozygosity. Decreased KEAP1 activity in cancer cells induced greater nuclear accumulation of NRF2 causing enhanced transcriptional induction of antioxidant and xenobiotic metabolism enzymes that counteract oxidative stress as well as cytotoxicity induced by drugs and other electrophiles. These results indicate that increased NRF2 activity is an important survival mechanism for NSCLC cells that leads to chemoresistance.

Accordingly, the invention provides therapeutic compositions and methods of decreasing Nrf2 expression for the treatment of a neoplasia, including inhibitory nucleic acid molecules, such as siRNAs. Such compositions are particularly useful when administered in combination with a chemotherapeutic agent for the treatment of a chemoresistant neoplasia. The invention further provides diagnostic methods that identify a subject as having a neoplasia or a chemoresistant neoplasia by identifying an increase in the expression of Nrf2 or an Nrf2 dependent gene. Nrf2 and Nrf2 dependent genes are particularly useful as Markers for the diagnosis of chemoresistant neoplasias.

Nrf2 RNA Interference

RNA interference (RNAi) is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of shRNAs using a plasmid-based expression system is currently being used to create loss-of-function phenotypes in mammalian cells. As described herein, siRNAs that target Nrf2 decrease Nrf2 expression in vivo.

Nrf2 Inhibitory Nucleic Acid Molecules

Nrf2 inhibitory nucleic acid molecules are essentially nucleobase oligomers that may be employed as single-stranded or double-stranded nucleic acid molecule to decrease Nrf2 expression. In one approach, the Nrf2 inhibitory nucleic acid molecule is a double-stranded RNA used for RNA interference (RNAi)-mediated knock-down of Nrf2 gene expression. In one embodiment, a double-stranded RNA (dsRNA) molecule is made that includes between eight and twenty-five (e.g., 8, 10, 12, 15, 16, 17, 18, 19, 20, 21, 22, 23, 24, 25) consecutive nucleobases of a nucleobase oligomer of the invention. The dsRNA can be two complementary strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. Double stranded RNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference. An inhibitory nucleic acid molecule that "corresponds" to an Nrf2 gene comprises at least a fragment of the double-stranded gene, such that each strand of the double-stranded inhibitory nucleic acid molecule is capable of binding to the complementary strand of the target Nrf2 gene. The inhibitory nucleic acid molecule need not have perfect correspondence to the reference Nrf2 sequence. In one embodiment, an siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleobase sequence of the inhibitory nucleic acid molecule exhibits 1, 2, 3, 4, 5 or more mismatches.

The inhibitory nucleic acid molecules provided by the invention are not limited to siRNAs, but include any nucleic acid molecule sufficient to decrease the expression of an Nrf2 nucleic acid molecule or polypeptide. Each of the DNA sequences provided herein may be used, for example, in the discovery and development of therapeutic antisense nucleic acid molecule to decrease the expression of Nrf2. The invention further provides catalytic RNA molecules or ribozymes. Such catalytic RNA molecules can be used to inhibit expression of an Nrf2 nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. In various embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

After a subject is diagnosed as having a neoplasia (e.g., prostate cancer) a method of treatment is selected. A number of standard treatment regimens are known to clinicians. Neoplasias that have not acquired chemoresistance are likely to be susceptible to treatment with conventional chemotherapeutics. Neoplasias that have developed chemoresistance are unlikely to be susceptible to treatment with conventional chemotherapy and are likely to require a more aggressive method of treatment. While conservative methods of treatment are appropriate for less aggressive neoplasias, more aggressive neoplasias require more aggressive therapeutic regimens. A more aggressive treatment regimen would typically involve the use of higher dosages of a chemotherapeutic agent or the use of chemotherapeutic agents having increased toxicity or adverse side effects.

In one embodiment, the inhibitory nucleic acid molecules of the invention are administered systemically in dosages between about 1 and 100 mg/kg (e.g., 1, 5, 10, 20, 25, 50, 75, and 100 mg/kg). In other embodiments, the dosage ranges from between about 25 and 500 $mg/m^2$/day. Desirably, a human patient having a chemoresistant neoplasia, or a neoplasia at risk of developing chemoresistance, receives a dosage between about 50 and 300 $mg/m^2$/day (e.g., 50, 75, 100, 125, 150, 175, 200, 250, 275, and 300).

Modified Inhibitory Nucleic Acid Molecules

A desirable inhibitory nucleic acid molecule is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed to enhance the stability or efficacy of an inhibitory nucleic acid molecule.

Inhibitory nucleic acid molecules include nucleobase oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957;

5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleobase oligomers, both the sugar and the internucleoside linkage, i.e., the backbone, are replaced with novel groups. The nucleobase units are maintained for hybridization with an Nrf2 nucleic acid molecule. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Nrf2 Polynucleotides

In general, the invention includes any nucleic acid sequence encoding an Nrf2 polypeptide. Also included in the methods of the invention are any nucleic acid molecule containing at least one strand that hybridizes with such a Nrf2 nucleic acid sequence (e.g., an inhibitory nucleic acid molecule, such as a dsRNA, siRNA, shRNA, or antisense molecule). The inhibitory nucleic acid molecules of the invention encoding a Nrf2 polypeptide can be 19-21 nucleotides in length. In some embodiments, the inhibitory nucleic acid molecules of the invention comprises 20, 19, 18, 17, 16, 15, 14, 13, 12, 11, 10, 9, 8, or 7 identical nucleotide residues. In yet other embodiments, the single or double stranded antisense molecules are 60%, 65%, 70%, 75%, 80%, 85%, 90%, 95%, 96%, 97%, 98%, 99% complementary to the Nrf2 target sequence. An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Further embodiments can include any of the above inhibitory polynucleotides, directed to Keap1, Phase II genes, including glutathione-S-transferases (GSTs), antioxidants (GSH), and Phase II drug efflux proteins, including the multidrug resistance proteins (MRPs), or portions thereof.

Delivery of Nucleobase Oligomers

Naked oligonucleotides are capable of entering tumor cells and inhibiting the expression of Nrf2. Nonetheless, it may be desirable to utilize a formulation that aids in the delivery of an inhibitory nucleic acid molecule or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Nrf2 Polynucleotide Therapy

Polynucleotide therapy featuring a polynucleotide encoding a Nrf2 inhibitory nucleic acid molecule or analog thereof is another therapeutic approach for treating a neoplasia or treating multidrug resistance in a subject. Expression vectors encoding inhibitory nucleic acid molecules can be delivered to cells of a subject having a neoplasia. The nucleic acid molecules must be delivered to the cells of a subject in a form in which they can be taken up and are advantageously expressed so that therapeutically effective levels can be achieved.

Methods for delivery of the polynucleotides to the cell according to the invention include using a delivery system such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a Nrf2 inhibitory nucleic acid molecule, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of an Nrf2 inhibitory nucleic acid molecule therapeutic to a cell of a patient diagnosed as having a neoplasia. For example, a Nrf2 inhibitory nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), orby micro-injection under surgical conditions (Wolff et al., Science 247:1465, 1990). Preferably the Nrf2 inhibitory nucleic acid molecules are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell.

Nrf2 inhibitory nucleic acid molecule expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

For any particular subject, the specific dosage regimes should be adjusted over time according to the individual need and the professional judgment of the person administering or supervising the administration of the compositions.

Pharmaceutical Compositions

As reported herein, increased Nrf2 expression is associated with the development of chemoresistance in neoplastic cells. Accordingly, the invention provides therapeutic compositions that decrease Nrf2 expression to treat or prevent chemoresistance in a neoplasm, such as lung cancer. In one embodiment, the present invention provides a pharmaceutical composition comprising an Nrf2 inhibitory nucleic acid molecule (e.g., an antisense, siRNA, or shRNA polynucleotide) that decreases the expression of an Nrf2 nucleic acid molecule or polypeptide. If desired, the Nrf2 inhibitory nucleic acid molecule is administered in combination with a chemotherapeutic agent. Since Nrf2 regulates drug detoxification enzymes, targeting this molecule has a broad effect on all anticancer drugs. In various embodiments, the Nrf2 inhibitory nucleic acid molecule is administered prior to, concurrently with, or following administration of a chemotherapeutic. Without wishing to be bound by theory, administration of an Nrf2 inhibitory nucleic acid molecule likely enhances the accumulation or efficacy of a chemotherapeutic agent. Polynucleotides of the invention may be administered as part of a pharmaceutical composition. The compositions should be sterile and contain a therapeutically effective amount of the polypeptides or nucleic acid molecules in a unit of weight or volume suitable for administration to a subject.

An inhibitory nucleic acid molecule of the invention, or other negative regulator of Nrf2, may be administered within a pharmaceutically-acceptable diluents, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracistemal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for Nrf2 inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleobase oligomer of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm. With respect to a subject having chemoresistance, an effective amount is sufficient to stabilize, slow, reduce, or reverse the chemoresistance. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the Nrf2 polynucleotide or polypeptide compositions of the present invention.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracistemal, intracerebroventricular, intratracheal, nasal, transdermal, within/on implants, e.g., fibers such as collagen, osmotic pumps, or grafts comprising appropriately transformed cells, etc., or parenteral routes.

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with an inhibitory nucleic acid molecule of the invention may be combined with therapies for the treatment of proliferative disease (e.g., radiotherapy, surgery, or chemotherapy). For any of the methods of application described above, an inhibitory nucleic acid molecule of the invention is desirably administered intravenously or is applied to the site of neoplasia (e.g., by injection).

After a subject is diagnosed as having a neoplasia (e.g., prostate cancer) a method of treatment is selected. A number of standard treatment regimens are known to clinicians. Neoplasias that have not acquired chemoresistance are likely to be susceptible to treatment with conventional chemotherapeutics. Neoplasias that have developed chemoresistance are unlikely to be susceptible to treatment with conventional chemotherapy and are likely to require a more aggressive method of treatment. While conservative methods of treatment are appropriate for less aggressive neoplasias, more aggressive neoplasias require more aggressive therapeutic regimens. A more aggressive treatment regimen would typically involve the use of higher dosages of a chemotherapeutic agent or the use of chemotherapeutic agents having increased toxicity or adverse side effects.

Diagnostics

Nuclear factor erythroid-2 related factor 2 (NRF2) is a redox-sensitive transcription factor that regulates the expression of antioxidants and xenobiotic metabolism genes and confers cytoprotection against oxidative stress. Kelchlike ECH-associated protein (KEAP1) negatively regulates NRF2 activity by targeting it for proteasomal degradation. Neoplastic tissues may express higher levels of Nrf2 nucleic acid molecule or polypeptide and its target antioxidant and xenobiotic metabolism nucleic acid molecules or polypeptides than corresponding normal tissues. Thus, an alteration in the expression level of one or more of the following markers is used to diagnose a neoplasia, or to identify a chemoresistant neoplasia: Nrf2, Keap1, Phase II genes, including glutathione-S-transferases (GSTs), antioxidants (GSH), and Phase III drug efflux proteins, including the multidrug resistance proteins (MRPs).

In one embodiment, subjects may be diagnosed for a propensity to develop a neoplasia (e.g., a chemoresistant neoplasia), the method involves measuring markers in a biological sample from a patient at risk for developing a neoplasia, and detecting an alteration in the expression of a test marker molecule relative to the sequence or expression of a reference molecule. The markers can be selected from Nrf2, Keap1, Phase II genes, including glutathione-S-transferases (GSTs), antioxidants (GSH), and Phase III drug efflux proteins, including the multidrug resistance proteins (MRPs). In a further embodiment, subjects may be diagnosed for a propensity to develop chemoresistance, the method comprising measuring markers in a biological sample from a patient at risk for developing chemoresistance, and detecting an alteration in the expression of test marker molecules relative to the sequence or expression of a reference molecule. The markers can be selected from Nrf2, Keap1, Phase II genes, including glutathione-S-transferases (GSTs), antioxidants (GSH), and Phase III drug efflux proteins, including the multidrug resistance proteins (MRPs). While the following approaches describe diagnostic methods featuring Nrf2, the skilled artisan will appreciate that any one or more of the markers set forth above is useful in such diagnostic methods.

Increased expression of a Nrf2 nucleic acid molecule or polypeptide is correlated with neoplasia and is further correlated with chemoresistance. Accordingly, the invention provides compositions and methods for identifying a neoplasia or a chemoresistant neoplasia in a subject. The present invention provides a number of diagnostic assays that are useful for the identification or characterization of a neoplasia or chemoresistance. Alterations in gene expression are detected using methods known to the skilled artisan and described herein. Such information can be used to diagnose a neoplasia or chemoresistance.

In one approach, diagnostic methods of the invention are used to assay the expression of a Nrf2 polypeptide in a biological sample relative to a reference (e.g., the level of Nrf2 polypeptide present in a corresponding control tissue). In one embodiment, the level of an Nrf2 polypeptide is detected using an antibody that specifically binds a Nrf2 polypeptide. Exemplary antibodies that specifically bind an Nrf2 polypeptide are described herein. By "antibody" is meant any immunoglobulin polypeptide, or fragment thereof, having immunogen binding ability. Such antibodies are useful for the diagnosis of a neoplasia. Such antibodies are also useful for the diagnosis of chemoresistance. Methods for measuring an antibody-Nrf2 complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Other useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology Antibodies in Cell Biology, volume 37 (Asai, ed. 1993); Basic and Clinical Immunology (Stites & Terr, eds., 7th ed. 1991); and Harlow & Lane, supra. Immunoassays can be used to determine the quantity of Nrf2 in a sample, where an increase in the level of the Nrf2 polypeptide is diagnostic of a patient having a neoplasia.

In one approach, quantitative PCR methods are used to identify an increase in the expression of an Nrf2 nucleic acid molecule. In another approach, PCR methods are used to identify an alteration in the sequence of an Nrf2 nucleic acid molecule. The invention provides probes that are capable of detecting a Nrf2 nucleic acid molecule, including genomic sequences, or closely related molecules. Such probes may be used to hybridize to a nucleic acid sequence derived from a patient having a neoplasia. The specificity of the probe determines whether the probe hybridizes to a naturally occurring sequence, allelic variants, or other related sequences. Hybridization techniques may be used to identify mutations indicative of a neoplasia or chemoresistance, or may be used to monitor expression levels of these genes (for example, by Northern analysis (Ausubel et al., supra).

Another embodiment encompasses a method of diagnosing a subject as having, or having a propensity to develop, a neoplasia or a chemoresistant neoplasia. The method comprises sequencing the Keap1 gene in a subject sample, wherein a mutation in Keap1 relative to a reference indicates that the subject has, or has a propensity to develop a neoplasia. Further, the method can encompass diagnosing a subject as having, or having a propensity to develop, chemoresistance. The method comprises sequencing the Keap1 gene in a subject sample, wherein a mutation in Keap1 relative to a reference indicates that the subject has, or has a propensity to develop chemoresistance.

In general, the measurement of a nucleic acid molecule in a subject sample is compared with a diagnostic amount present in a reference. A diagnostic amount distinguishes between a neoplastic or chemoresistant tissue and a control tissue. The skilled artisan appreciates that the particular diagnostic amount used can be adjusted to increase sensitivity or specificity of the diagnostic assay depending on the preference of the diagnostician. In general, any significant increase (e.g., at least about 10%, 15%, 30%, 50%, 60%, 75%, 80%, or 90%) in the level of test nucleic acid molecule or test polypeptide in the subject sample relative to a reference may be used to diagnose a neoplasia or chemoresistance. Test molecules include Nrf2, Keap1, Phase II genes, including glutathione-S-transferases (GSTs), antioxidants (GSH), and Phase III drug efflux proteins, including the multidrug resistance proteins (MRPs). In one embodiment, the reference is the level of test polypeptide or nucleic acid molecule present in a control sample obtained from a patient that does not have a neoplasia or multi-drug resistance. In another embodiment, the reference is a baseline level of test molecule present in a biologic sample derived from a patient prior to, during, or after treatment for a neoplasia. In yet another embodiment, the reference can be a standardized curve.

Types of Biological Samples

The level of markers in a biological sample from a patient at risk for developing chemoresistance can be measured, and an alteration in the expression of test marker molecules relative to the sequence or expression of a reference molecule, can be determined in different types of biologic samples. Test markers include Nrf2, Keap1, Phase II genes glutathione-S-transferases (GSTs), antioxidants such as glutathione (GSH) and Phase III drug efflux proteins, including the multi drug resistance protein (MRP) family. The biological samples are generally derived from a patient, preferably as a bodily fluid (such as blood, cerebrospinal fluid, phlegm, saliva, or urine) or tissue sample (e.g. a tissue sample obtained by biopsy).

Kits

The invention provides kits for the diagnosis or monitoring of a neoplasia, such as a chemoresistant neoplasia. In one embodiment, the kit detects an alteration in the expression of a Marker (e.g., Nrf2, Keap1, Phase II genes, including glutathione-S-transferases (GSTs), antioxidants (GSH), and Phase III drug efflux proteins, including the multidrug resistance proteins (MRPs)) nucleic acid molecule or polypeptide relative to a reference level of expression. In another embodiment, the kit detects an alteration in the sequence of a Keap1 nucleic acid molecule derived from a subject relative to a reference sequence. In related embodiments, the kit includes reagents for monitoring the expression of a Nrf2 nucleic acid molecule, such as primers or probes that hybridize to a Nrf2 nucleic acid molecule. In other embodiments, the kit includes an antibody that binds to a Nrf2 polypeptide.

Optionally, the kit includes directions for monitoring the nucleic acid molecule or polypeptide levels of a Marker in a biological sample derived from a subject. In other embodiments, the kit comprises a sterile container which contains the primer, probe, antibody, or other detection regents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

Patient Monitoring

The disease state or treatment of a patient having a neoplasia can be monitored using the methods and compositions of the invention. In one embodiment, the chemoresistance of a patient can be monitored using the methods and compositions of the invention. Such monitoring may be useful, for example, in assessing the efficacy of a particular drug in a patient. Therapeutics that alter the expression of a Nrf2 nucleic acid molecule or Nrf2 polypeptide are taken as particularly useful in the invention. Other nucleic acids or polypeptides according to the invention that are useful for monitoring or in aspects of the invention include Nrf2, Keap1, Phase II genes, including glutathione-S-transferases (GSTs), antioxidants (GSH), and Phase II drug efflux proteins, including the multidrug resistance proteins (MRPs).

Screening Assays

One embodiment of the invention encompasses a method of identifying an agent that inhibits chemoresistance. Accordingly, compounds that modulate the expression or activity of a Nrf2 nucleic acid molecule, polypeptide, variant, or portion thereof are useful in the methods of the invention for the treatment or prevention of a neoplasm (e.g., breast, colon, lymph, ovary, stomach, thyroid, testis, and uterine cancer) or chemoresistance. The method of the invention may measure a decrease in transcription or translation. Any number of methods are available for carrying out screening assays to identify such compounds. In one approach, the method comprises contacting a cell that expresses Nrf2 nucleic acid molecule with an agent and comparing the level of Nrf2 nucleic acid molecule or polypeptide expression in the cell contacted by the agent with the level of expression in a control cell, wherein an agent that decreases Nrf2 expression thereby inhibits chemoresistance. In another approach, candidate compounds are identified that specifically bind to and alter the activity of a polypeptide of the invention (e.g., a Nrf2 activity associated with cell proliferation, mitosis or maintenance of chromosomal stability). Methods of assaying such biological activities are known in the art and are described herein. The efficacy of such a candidate compound is dependent upon its ability to interact with a Nrf2 nucleic acid molecule, Nrf2 polypeptide, a variant, or portion. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate cell proliferation, mitosis, or maintenance of chromosomal stability. Standard methods for perturbing or reducing Nrf2 expression include mutating or deleting an endogenous Nrf2 sequence, interfering with Nrf2 expression using RNAi, or microinjecting an Nrf2-expressing cell with an antibody that binds Nrf2 and interferes with its function. Alternatively, chromosomal nondysjunction can be assayed in vivo, for example, in a mouse model in which Nrf2 has been knocked out by homologous recombination, or any other standard method.

Potential agonists and antagonists of an Nrf2 polypeptide include organic molecules, peptides, peptide mimetics, polypeptides, nucleic acid molecules (e.g., double-stranded RNAs, siRNAs, antisense polynucleotides), and antibodies that bind to a nucleic acid sequence or polypeptide of the invention and thereby inhibit or extinguish its activity. Potential antagonists also include small molecules that bind to the Nrf2 polypeptide thereby preventing binding to cellular molecules with which the Nrf2 polypeptide normally interacts, such that the normal biological activity of the Nrf2 polypeptide is reduced or inhibited. Small molecules of the invention preferably have a molecular weight below 2,000 daltons, more preferably between 300 and 1,000 daltons, and still more preferably between 400 and 700 daltons. It is preferred that these small molecules are organic molecules.

Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized to identify compounds that interact with Nrf2 nucleic acid or polypeptide. Interacting compounds isolated by this method (or any other appropriate method) may, if desired, be further purified (e.g., by high performance liquid chromatography). Compounds isolated by any approach described herein may be used as therapeutics to treat a neoplasia in a human patient.

In addition, compounds that inhibit the expression of an Nrf2 nucleic acid molecule whose expression is increased in a subject having a neoplasia, or a subject with multi drug resistance, are also useful in the methods of the invention. Any number of methods are available for carrying out screening assays to identify new candidate compounds that alter the expression of a Nrf2 nucleic acid molecule. In one approach, the effect of candidate compounds can be measured at the level of polypeptide production to identify those that promote an alteration in a Nrf2 polypeptide level. The level of Nrf2 polypeptide can be assayed using any standard method. Standard immunological techniques include Western blotting or immunoprecipitation with an antibody specific for an Nrf2 polypeptide (e.g., Nrf2, a Nrf2 variant). For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, Western blot, or RIA assay) to measure the level of the polypeptide. In some embodiments, a compound that promotes a decrease in the expression or biological activity of the polypeptide is considered particularly useful. Again, such a molecule may be used, for example, as a therapeutic to delay, ameliorate, or treat a neoplasia or chemoresistance in a human patient.

Each of the DNA sequences listed herein may also be used in the discovery and development of a therapeutic compound for the treatment of neoplasia. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

The invention also includes novel compounds identified by the above-described screening assays. Optionally, such compounds are characterized in one or more appropriate animal models to determine the efficacy of the compound for the treatment of a neoplasia. Desirably, characterization in an animal model can also be used to determine the toxicity, side effects, or mechanism of action of treatment with such a compound. Furthermore, novel compounds identified in any of the above-described screening assays may be used for the treatment of a neoplasia or multi-drug resistance in a subject. Such compounds are useful alone or in combination with other conventional therapies known in the art.

Test Compounds and Extracts

In general, compounds capable of inhibiting the growth or proliferation of a neoplasia by decreasing the expression or biological activity of a Nrf2 nucleotide or a Nrf2 polypeptide are identified from large libraries of either natural product or synthetic (or semi-synthetic) extracts or chemical libraries according to methods known in the art. Methods for making siRNAs are known in the art and are described in the Examples. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptide libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Biotechniques* 13:412-421, 1992), or on beads (Lam, *Nature* 354:82-84, 1991), chips (Fodor, *Nature* 364: 555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof or the elimination of replicates or repeats of materials already known for their anti-neoplastic activity should be employed whenever possible.

In an embodiment of the invention, a high throughput approach can be used to screen different chemicals for their potency to affect Nrf2 activity. A cell based transcriptional reporter approach, as described in Example 7 can be used to identify agents that inhibit Nrf2 transcription.

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of a Nrf2 polypeptide, variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogeneous extracts are known in the art. If desired, compounds shown to be useful agents for the treatment of a neoplasm are chemically modified according to methods known in the art.

Methods of Assaying Nrf2 Biological Activity

Therapeutics useful in the methods of the invention include, but are not limited to, those that have an anti-neoplastic activity or those that alter a Nrf2 biological activity associated with chemoresistance. Neoplastic cell growth is not subject to the same regulatory mechanisms that govern the growth or proliferation of normal cells. Compounds that reduce the growth or proliferation of a neoplasm are useful for the treatment of neoplasms. Methods of assaying cell growth and proliferation are known in the art. See, for example, Kittler et al. (Nature. 432 (7020): 1036-40, 2004) and by Miyamoto et al. (Nature 416(6883):865-9, 2002). Assays for cell proliferation generally involve the measurement of DNA synthesis during cell replication. In one example, proliferation is measured using a tetrazolium compound in the CELL TITER 96® Assay. Alternatively, [$^{3}$H]-Thymidine or 5-bromo-2'-deoxyuridine [BrdU], can be added to cells (or animals) and then the incorporation of these precursors into genomic DNA during the S phase of the cell cycle (replication) can be detected (Ruefli-Brasse et al., Science 302(5650):1581-4, 2003; Gu et al., Science 302 (5644):445-9, 2003).

Candidate compounds that reduce the survival of a neoplastic cell are also useful as anti-neoplasm therapeutics. Assays for measuring cell viability are known in the art, and are described, for example, by Crouch et al. (J. Immunol. Meth. 160, 81-8); Kangas et al. (Med. Biol. 62, 33843, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett.: 611, 1991; Cory et al., Cancer Comm. 3, 207-12, 1991; Paull J. Heterocyclic Chem. 25, 911, 1988). Assays for cell viability are also available commercially. These assays include CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay.

Candidate compounds that increase neoplastic cell death (e.g., increase apoptosis) are also useful as anti-neoplasm therapeutics. Assays for measuring cell apoptosis are known to the skilled artisan. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Combination Therapies

Compositions and methods of the invention may be used in combination with any conventional therapy known in the art. In one embodiment, Nrf2 inhibitory nucleic acid molecules having anti-neoplastic or anti-multi-drug resistance activity may be used in combination with any anti-neoplastic therapy known in the art. Exemplary anti-neoplastic therapies include, for example, chemotherapy, cryotherapy, hormone therapy, radiotherapy, and surgery. A Nrf2 polynucleotide composition of the invention may, if desired, include one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide (SEQ ID NO: 50), cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine. Other examples of chemotherapeutic agents can be found in Cancer Principles and Practice of Oncology by V. T. Devita and S. Hellman (editors), 6th edition (Feb. 15, 2001), Lippincott Williams & Wilkins Publishers.

The following examples are put forth so as to provide those of ordinary skill in the art with a complete disclosure and description of how to make and use the assay, screening, and therapeutic methods of the invention, and are not intended to limit the scope of what the inventors regard as their invention.

EXEMPLIFICATION

Abbreviations are as follows: ND, Nrf2 Duplex; SC siRNA, scramble control siRNA; shRNA, short hairpin RNA; CIS, cisplatin.

Example 1

KEAP-1 Mutation is a Frequent Genetic Alteration in Non-Small Cell Lung Carcinoma A genome wide search for loss of heterozygosity (LOH) in lung cancer cell lines identified chromosome 19p as a candidate tumor suppressor region showing more than 60% loss of heterozygosity (Girard L et al. *Cancer Res* 6: 4894 (2000)). Evaluation of loss of heterozygosity at 19p13.2 in 191 lung cancer cell lines from the cancer genome project database at the Sanger Center, United Kingdom, revealed allelic losses in 38% of the cancer cell lines tested. Results are depicted in a heat map (FIGS. 1A-1 to 1A-5). Heat maps were constructed using GeneCluster and Treeview software (Eisen lab, Stanford, Calif.). To determine whether mutations in the Keap1 gene KEAP1 are present in NSCLC, all 5 protein-coding exons and intron-exon boundaries of KEAP1 gene were amplified and sequenced in a set of 12 lung cancer cell lines. Table 1, shown below, is a summary of these results.

TABLE 1

KEAP1 sequence alterations in lung tumor-derived cell lines and patients; PT, primary tumor; PF, pleural fluid; aa, amino acid.

| Cell line/ Patient | Nucleotide Mutation | Amino acid Change | Amino acid Position | Domain |
|---|---|---|---|---|
| H460 | G-C | D-H | 236 | IVR |
| A549 | G-T | G-C | 333 | 1st Kelch domain |
| H1435 | G-T | L-R | 413 | 3rd kelch domain |
| H838 | G-T | Frameshift (Stop codon) | 443 | 3rd kelch domain |
| H1395 | G-A | G-S | 350 | 1st kelch domain |
| H1993 | G-A | G-S | 350 | 1st kelch domain |
| PT-23, 35 | A-T | Q-L | 284 | IVR |
| PT-29 | G-T | V-F | 167 | BTB |
| PT-17 | 2 bp deletion (GG) | Frameshift (Stop codon) | 413 | 3rd kelch domain |
| PT-18 | 1 bp deletion (G) | Frameshift (Stop codon) | 237 | IVR |
| PT-31 | 1 bp deletion (G) | Frameshift (Stop codon) | 457 | 3rd kelch domain |
| PF-3 | G-A | I-V | 264 | IVR |
| PF-4 | G-Insertion | Frameshift (Stop codon) | 348 | 1st kelch domain |
| PF-8, 9 | 18 bp deletion | 6 aa deletion | 555-560 | 6th kelch domain |

H460, A549, H1435, and H838 had only the mutant allele. H1395 and H1993 were heterozygous for mutation. H23, H358, H1299, H1703, H292, and H1666 had no mutations.

Figures 1, 1A, 2, 3, 4, 5:
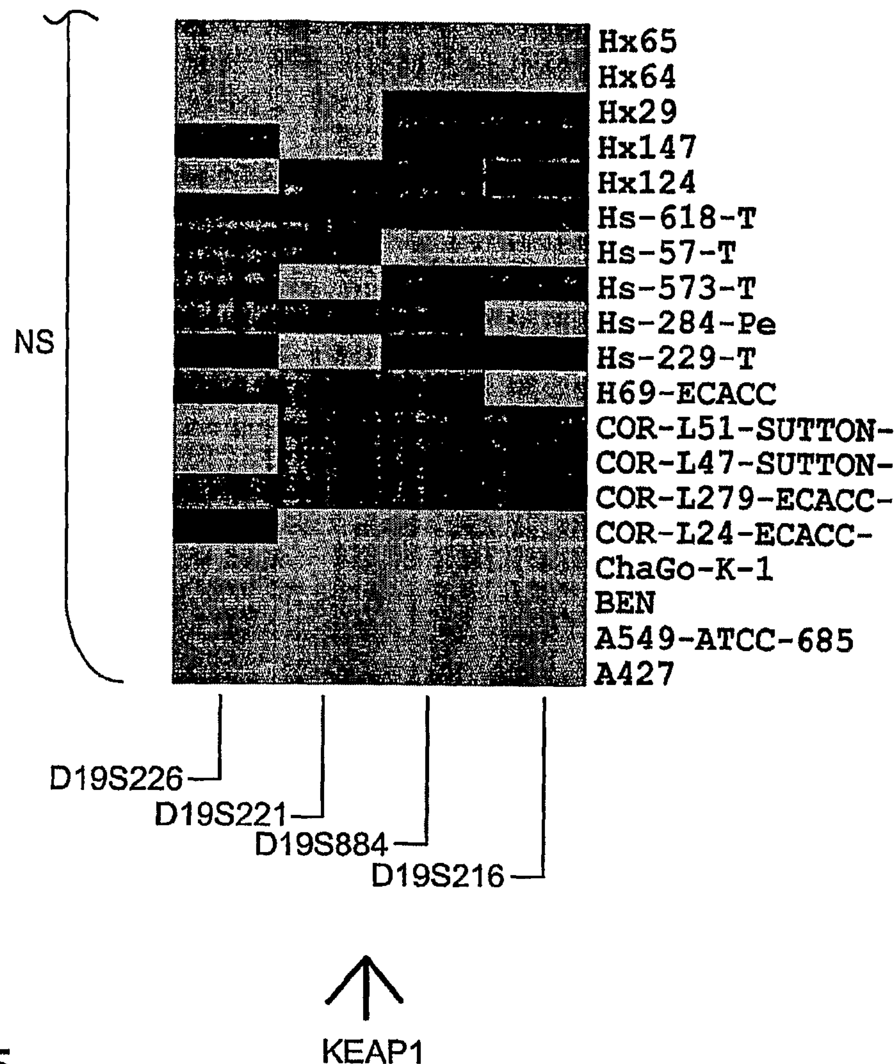
Figure 1B:
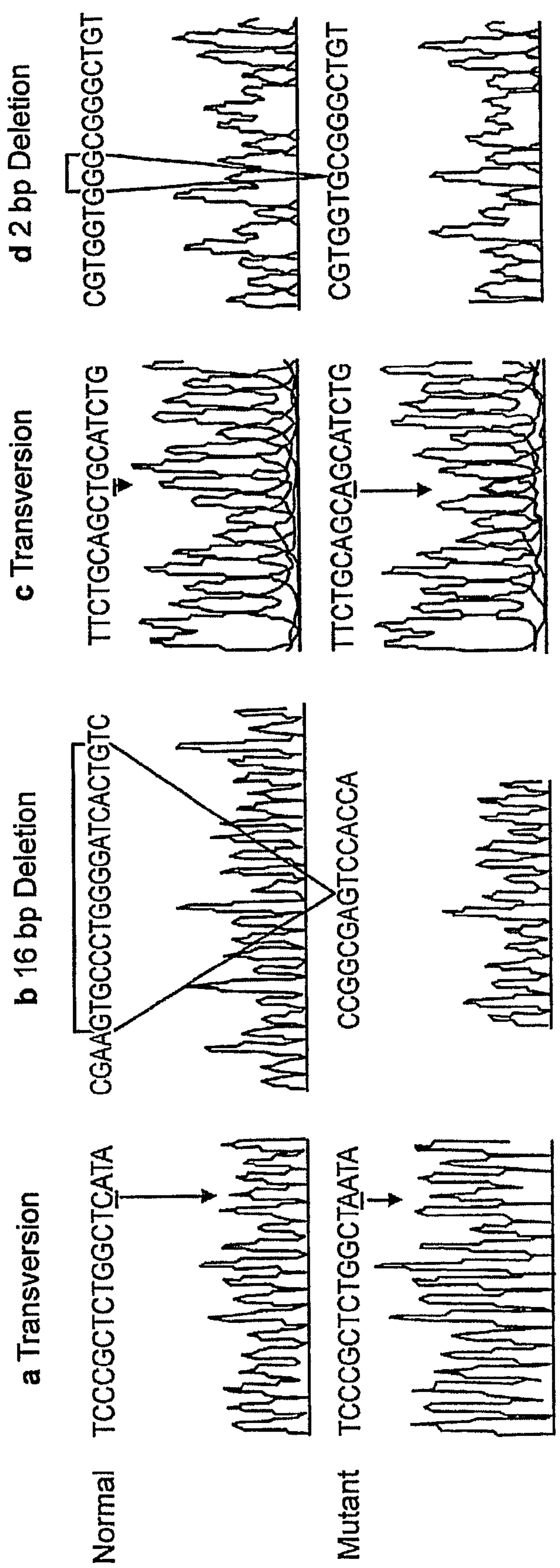
Figure 1C:
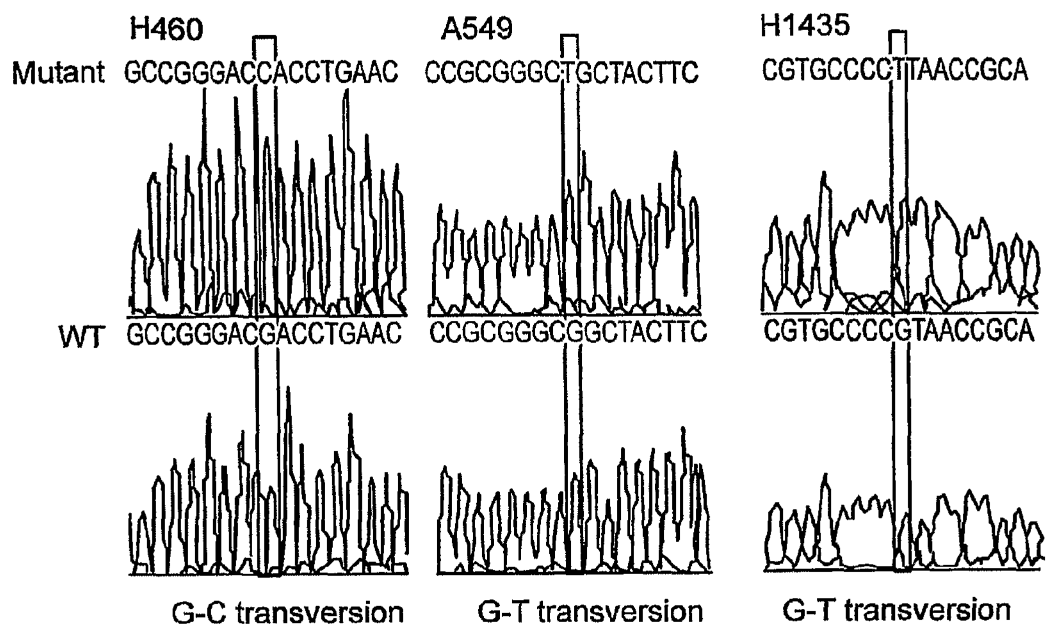
Figure 1D:
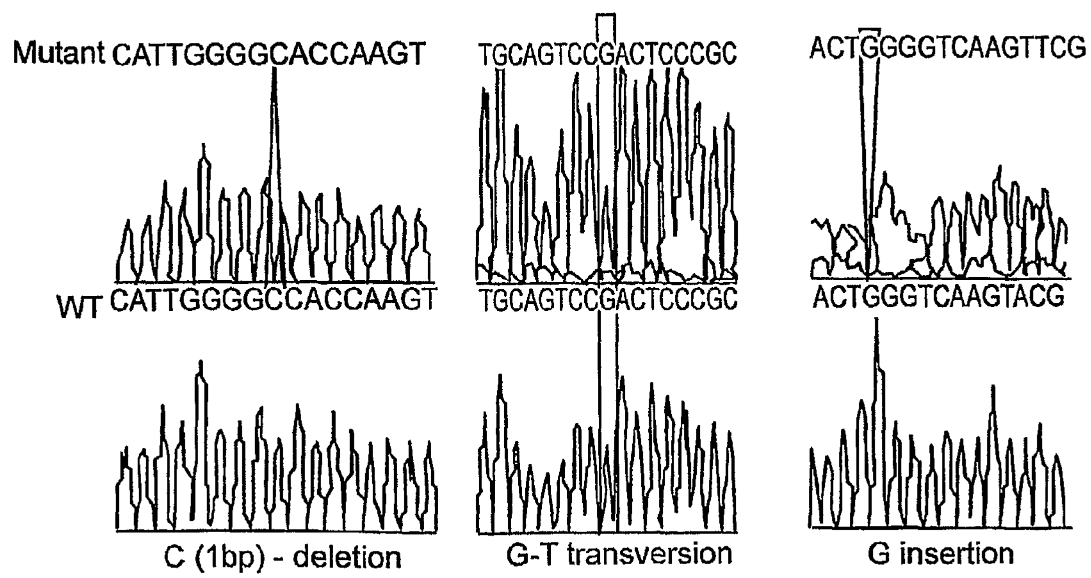

Point mutations, leading to non conservative aminoacid substitutions and nonsense mutations, were detected in 50% (6/12) of these cell lines. All mutations were within highly conserved amino acid residues located in the Kelch or UVR domain of the KEAP1 protein suggesting that these mutations would likely abolish KEAP1 repressor activity. Only the mutant allele and not the wild-type was detected in the H460, A549, H1435 and H838 cell lines indicating that the mutations were hemizygous, with corresponding loss of heterozygoity affecting the other allele. Representative electropherograms of the mutations are shown in FIG. 1B, FIG. 1C and FIG. 1D. The microsattelite database at the Sanger Centre showed that the H460, A549 and H838 cell lines had allelic loss at 19p13.2, which confirmed that the wild-type KEAP1 allele was lost by loss of heterozygoity and that the retained allele was inactivated by somatic mutations. H1435 was not included in the Sanger Centre database.

All the mutations identified in patients were heterozygous. KEAP1 was also sequenced in 4 non-malignant (normal) human lung epithelial cell lines (BEAS2B, NL20, HBE4, and NHBE). These normal cell lines expressed only the wild type Keap1 sequence, as shown in Table 2 below.

TABLE 2

| Cell line Name/No. | Pathology | Tumor Derived | Normal Derived | DNA change | Amino acid change | LOH status (Sanger center database) |
|---|---|---|---|---|---|---|
| NHBE | N.D. | N.A. | Yes | WT | None | No Information |
| BEAS2B | N.D. | N.A. | Yes | WT | None | No Information |
| HBE4 | N.D. | N.A. | Yes | WT | None | No Information |
| NL20 | N.D. | N.A. | Yes | WT | None | No Information |
| A549 | Adenocarcinoma | Yes | N.A. | G-T transversion | G-C | Complete Loss |
| H838 | Adenocarcinoma | Yes | N.A. | G-T transversion | Stop codon | Complete Loss |
| H1435 | Adenocarcinoma | Yes | N.A. | G-T transversion | L-R | No Information |
| H460 | Large Cell | Yes | N.A. | G-C transversion | D-H | Complete Loss |
| H1395 | Adenocarcinoma | Yes | N.A. | G-A transition | G-S | Complete Loss |
| H1993 | Adenocarcinoma | Yes | N.A. | G-A transition | G-S | Complete Loss |
| H23 | NSCLC | Yes | N.A. | WT | None | Partial loss |
| H1668 | Bronchioloalveolar | Yes | N.A. | WT | None | No loss |
| H358 | Bronchioloalveolar | Yes | N.A. | WT | None | Partial loss |
| H1299 | Large Cell | Yes | N.A. | WT | None | Complete Loss |
| H292 | Mucoepidermoid | Yes | N.A. | WT | None | No Information |
| H1703 | Adenocarcinoma | Yes | N.A. | WT | None | Complete Loss |

N.A, Not Available; N.D., Not Determined

KEAP1 was also sequenced in 40 primary lung tumors, 25 of which were paired with normal tissue samples, and 16 pleural fluid samples from lung cancer patients at Johns Hopkins Hospital, Baltimore, USA. The primary tumors included 19 adenocarcinoma, 6 large cell carcinoma, and 15 squamous cell carcinoma samples. The pleural fluid samples included 14 non-small-cell adenocarcinoma and 2 small-cell carcinoma samples. Exon sequencing of the genomic DNA from tumor tissues showed deletion, insertion, missense, and frameshift mutations in KEAP1 in a total of 10 tumors Frequency of mutation in primary tumors and pleural fluid was 15.0% (6/40) and 25% (4/16), respectively (FIG. 1B). The majority of the mutations identified affected highly conserved amino acids located in functionally important domains of KEAP1, as shown in Table 1, above. Four different deletions and one single base pair insertion were found. All of these alterations, with the exception of the 18 base pair deletion, introduced a premature stop codon that resulted in a truncated KEAP1 protein. All sequence alterations in this group were heterozygous in tumor DNA. These mutations were detected only in adenocarcinomas. No mutations were detected in the paired normal tissue, which confirms that the tumor-derived mutations were somatic in origin. As shown in Table 3, an overall mutation frequency of 18.51% (10/54) for the KEAP1 gene in NSCLC tissues indicated that KEAP1 mutation is a frequent genetic alteration in non-small cell lung cancer.

TABLE 3

| | | | | | | | | LOH status | |
|---|---|---|---|---|---|---|---|---|---|
| Patient Number | Race | Pathology | Stage | Tumor DNA Sequenced | Normal DNA Sequenced | Mutation Status | Amino acid change | KEAP-DM1 | KEAP-UM1 |
| PT-1 | AS | Adenocarcinoma | 2B | Yes | Yes | WT | None | WT | MIC |
| PT-2 | AA | Adenocarcinoma | 1A | Yes | Yes | WT | None | LOH | LOH |
| PT-3 | CA | Adenocarcinoma | 2B | Yes | Yes | WT | None | WT | NI |
| PT-4 | CA | Squamous | 1A | Yes | Yes | WT | None | WT | WT |
| PT-5 | CA | Squamous | 1B | Yes | Yes | WT | None | LOH | NI |
| PT-6 | CA | Adenocarcinoma | 2B | Yes | Yes | WT | None | LOH | NI |
| PT-7 | CA | Adenocarcinoma | 2B | Yes | Yes | WT | None | NI | NI |
| PT-8 | CA | Adenocarcinoma | 3B | Yes | Yes | WT | None | WT | NI |
| PT-9 | CA | Squamous | 1A | Yes | Yes | WT | None | WT | NI |
| PT-10 | AA | Squamous | 1B | Yes | Yes | WT | None | LOH | MIC |
| PT-11 | CA | Squamous | 1B | Yes | Yes | WT | None | WT | NI |
| PT-12 | CA | Large Cell | 1B | Yes | Yes | WT | None | WT | MIC |
| PT-13 | AA | Squamous | 1B | Yes | Yes | WT | None | WT | WT |
| PT-14 | AA | Squamous | 1A | Yes | Yes | WT | None | LOH | LOH |
| PT-15 | CA | Squamous | 1B | Yes | Yes | WT | None | WT | WT |
| PT-16 | CA | Adenocarcinoma | 2B | Yes | Yes | WT | None | WT | NI |
| PT-17 | CA | Adenocarcinoma | 3B | Yes | Yes | 2 bp deletion | Stop Codon | LOH | NI |
| PT-18 | CA | Adenocarcinoma | 1B | Yes | Yes | 1 bp deletion | Stop Codon | LOH | WT |
| PT-19 | CA | Squamous | 2A | Yes | Yes | WT | None | WT | NI |
| PT-20 | CA | Squamous | 3A | Yes | Yes | WT | None | WT | WT |
| PT-21 | CA | Squamous | 3B | Yes | Yes | WT | None | MIC | WT |
| PT-22 | CA | Squamous | 1B | Yes | Yes | WT | None | WT | MIC |
| PT-23 | AA | Adenocarcinoma | 3A | Yes | Yes | A-T transversion | Q-L | LOH | LOH |
| PT-24 | CA | Adenocarcinoma | 3A | Yes | N.D. | WT | None | WT | WT |
| PT-25 | AA | Squamous | 1B | Yes | N.D. | WT | None | WT | WT |
| PT-26 | CA | Large Cell | 1B | Yes | N.D. | WT | None | WT | NI |
| PT-27 | CA | Large Cell | 1B | Yes | N.D. | WT | None | LOH | NI |
| PT-28 | AA | Squamous | 1B | Yes | N.D. | WT | None | WT | NI |
| PT-29 | AA | Adenocarcinoma | 1B | Yes | N.D. | G-T transversion | V-F | LOH | LOH |
| PT-30 | CA | Adenocarcinoma | 1B | Yes | N.D. | WT | None | MIC | WT |
| PT-31 | CA | Adenocarcinoma | 1B | Yes | N.D. | 1 bp deletion | Stop Codon | MIC | NI |
| PT-32 | CA | Adenocarcinoma | 4 | Yes | N.D. | WT | None | WT | WT |
| PT-33 | CA | Adenocarcinoma | 2B | Yes | Yes | WT | None | NI | LOH |
| PT-34 | CA | Large Cell | 1B | Yes | N.D. | WT | None | WT | WT |
| PT-35 | CA | Large Cell | 1B | Yes | Yes | A-T transversion | Q-L | LOH | WT |
| PT-36 | CA | Adenocarcinoma | 3A | Yes | N.D. | WT | None | LOH | LOH |
| PT-37 | CA | Squamous | 1B | Yes | N.D. | WT | None | LOH | LOH |
| PT-38 | CA | Adenocarcinoma | 1A | Yes | N.D. | WT | None | LOH | MIC |
| PT-39 | CA | Large Cell | 1B | N.D. | N.D. | WT | None | LOH | NI |
| PT-40 | CA | Adenocarcinoma | 3A | N.D. | N.D. | N.D. | N.D. | N.D. | N.D. |
| PT-41 | CA | Adenocarcinoma | 1B | N.D. | N.D. | N.D. | N.D. | N.D. | N.D. |
| PT-42 | CA | Squamous | 3A | N.D. | N.D. | N.D. | N.D. | N.D. | N.D. |
| PT-43 | AA | IMT | 4 | N.D. | N.D. | N.D. | N.D. | N.D. | N.D. |
| PT-44 | CA | Squamous | 2B | N.D. | N.D. | N.D. | N.D. | N.D. | N.D. |
| PT-45 | CA | Adenocarcinoma | UK | Yes | N.D. | WT | None | N.D. | N.D. |

| | | | | | | | | LOH status | |
|---|---|---|---|---|---|---|---|---|---|
| Patient Number | Race | Pathology | Stage | PF DNA Sequenced | Normal DNA Sequenced | Mutation Status | Amino acid change | KEAP-DM1 | KEAP-UM1 |
| PF-1 | CA | Adenocarcinoma | 4 | Yes | NA | WT | None | NI | NI |
| PF-2 | AA | Adenocarcinoma | 4 | Yes | NA | WT | Nona | NI | NI |
| PF-3 | CA | Adenocarcinoma | 4 | Yes | NA | G-A | I-V | NI | NI |
| PF-4 | AA | Adenocarcinoma | 4 | Yes | NA | 1 bp Insertion | Stop codon | NI | NI |
| PF-5 | CA | NSCLC | 3B | Yes | NA | WT | None | NI | NI |
| PF-6 | CA | Adenocarcinoma | UK | Yes | NA | WT | None | NI | NI |
| PF-7 | CA | Adenocarcinoma | 4 | Yes | NA | WT | None | NI | NI |
| PF-8 | CA | Adenocarcinoma | 3B | Yes | NA | 18 bp Deletion | 6 aa deletion | NI | NI |
| PF-9 | CA | Adenocarcinoma | 3B | Yes | NA | 18 bp Deletion | 6 aa deletion | NI | NI |
| PP-10 | CA | Adenocarcinoma | 4 | Yes | NA | WT | None | NI | NI |
| PF-11 | AA | Adenocarcinoma | 3B | Yes | NA | WT | None | NI | NI |
| PF-12 | CA | Adenocarcinoma | 4 | Yes | NA | WT | None | NI | NI |
| PF-13 | AA | Adenocarcinoma | 4 | Yes | NA | WT | None | NI | NI |
| PF-14 | CA | Small Cell | 4 | Yes | NA | WT | None | NI | NI |
| PF-15 | CA | Small Cell | 4 | Yes | NA | WT | None | NI | NI |
| PF-16 | CA | Adenocarcinoma | 4 | Yes | NA | WT | None | NI | NI |

Figure 2A:
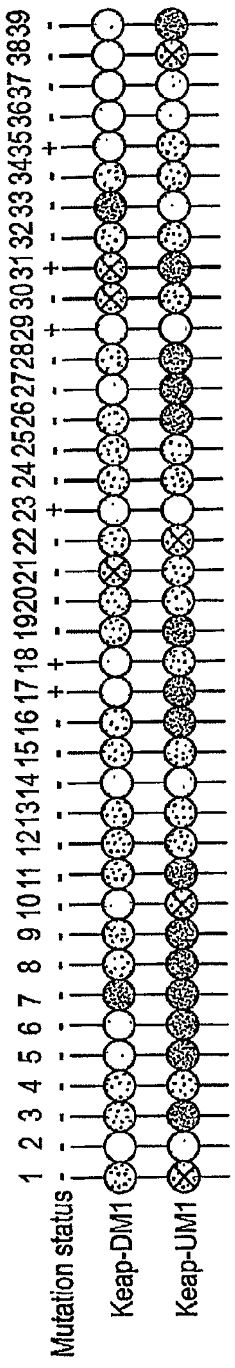
FIGS. 2A and 2B show loss of heterozygosity (LOH) at the Keap1 locus in human primary lung tumors.
Figure 2B:
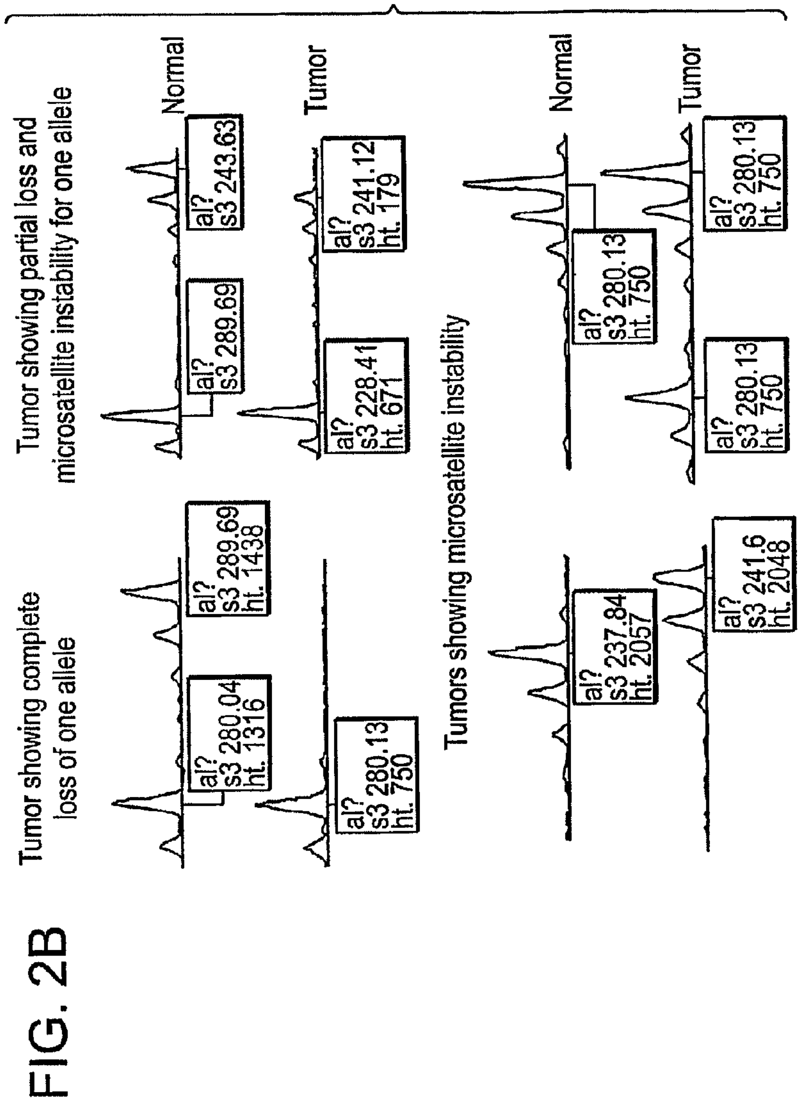

PT, primary tumor; AA, African American; CA, Caucasian; AS, Asian; UK, Unknown; NI, Non-Informative, WT, wild type; N.D., Not determined; aa, amino acid; IMT, inflammatory myofibroblastic tumor PF, Pleural fluid sample; AA, African American; CA, Caucasian; UK, Unknown; NA, Not avaliable; NI, Non-informative; WT, wild type; aa, amino acid;

To characterize the KEAP1 locus in primary lung tumors, two microsattelite markers, were used: KEAP-UM1 and KEAP-DM1. These microsattelite markers flank the KEAP1 gene within ~300 kb on either side. Pleural fluid DNA samples were not used for the loss of heterozygosity studies because the corresponding normal DNA was not available for these samples. Thirty-nine pairs of primary tumor and paired normal tissues were genotyped with these markers. Loss of heterozygosity was found for at least one of the markers in 41.0% (16/39) of the primary tumors. Six tumors showed only microsattelite instability in the region defined by these markers. Five of the six primary tumors (5/6) harboring KEAP1 mutations showed loss of heterozygosity of KEAP1; thus, as defined by the Knudson two-hit model, there was biallelic inactivation of KEAP1 in these tumors (Knudson A G Jr. *Cancer Res* 45: 1437 (1985)). According to Knudson, in familial cases, a mutation in one allele is inherited whereas the other mutation was acquired later. In sporadic tumours, both changes were somatic, with a similar mutation rate for both hits. Representative electropherograms showing the microsattelite instability and loss of heterozygosity are shown in FIGS. 2A and 2B.

Taken together, these results identified Keap1 mutation as a frequent genetic alteration in NSCLC.

Example 2

The Status of KEAP1 and Nrf2 is Altered in NSCLC

In this example, Keap1 and Nrf2 expression in NSCLC were characterized.

Figure 3A:
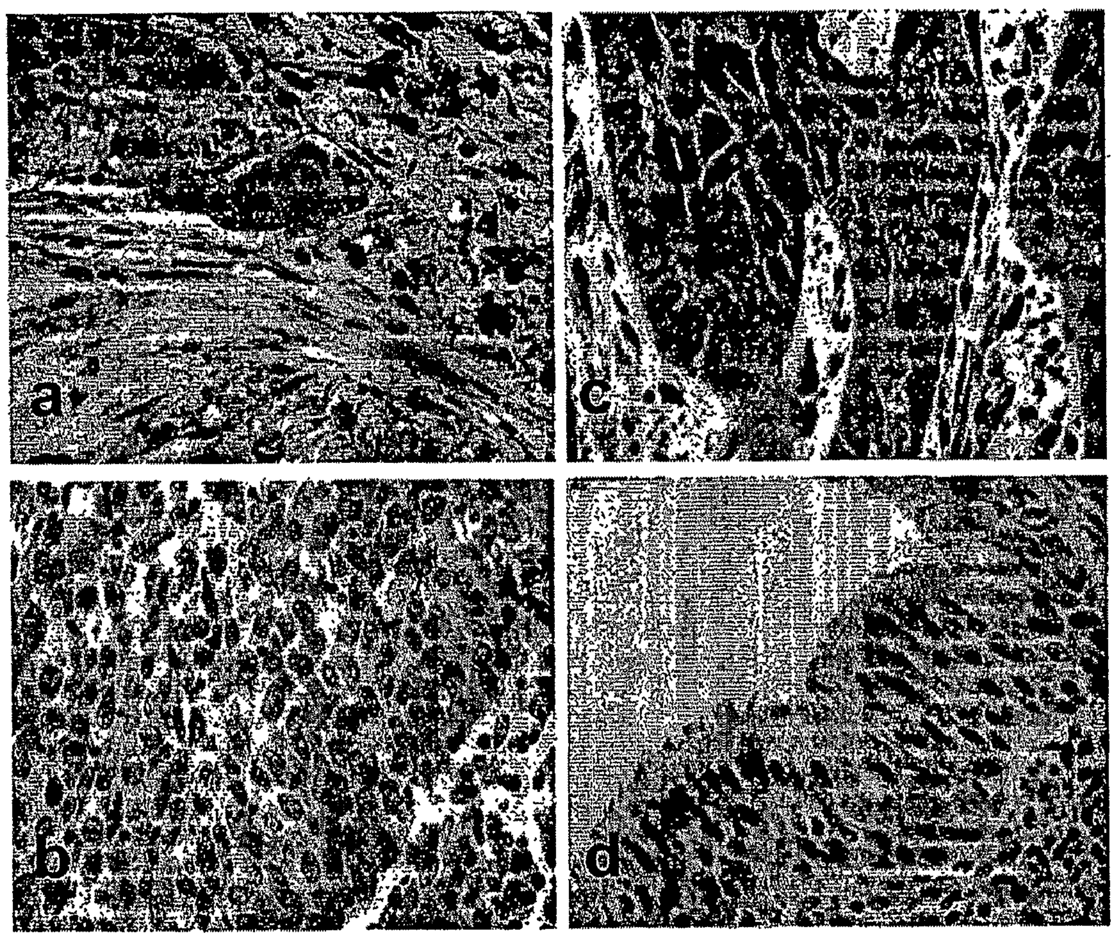
FIGS. 3A-3G show that NRF2 polypeptide levels and localization is altered in NSCLC.

Consistent with the findings described above, which indicated a loss of functional KEAP1 in lung cancers, immunohistochemical staining of NRF2 in lung adenocarcinoma tissues showed increased staining in tumor tissue relative to the staining observed in paired normal tissue (FIG. 3A). NRF2 immunohistochemistry was carried out using the following methods.

Figure 3B:
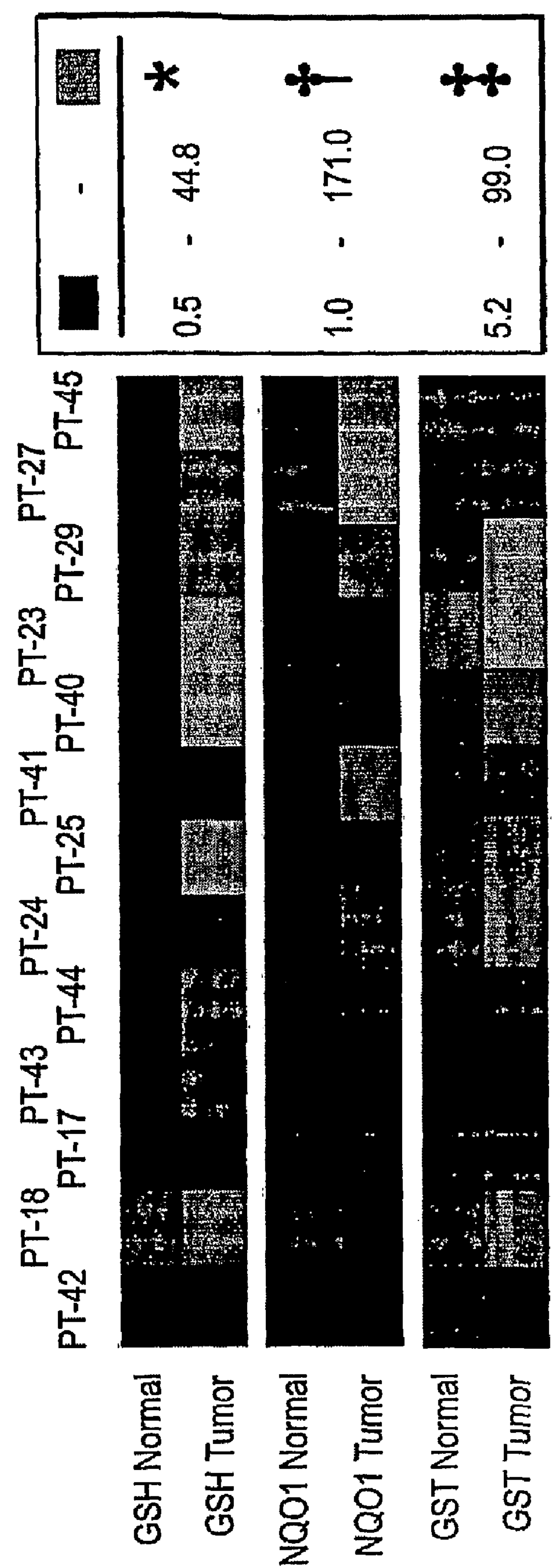

Formalin fixed tissues were treated with anti-NRF2 antibody (H-300, Santa Cruz) at a dilution of 1:250 for 1 hour and developed using horseradish peroxidase (DAKO). Prominent NRF2 staining was detected in both the nucleus and cytoplasm of tumor tissue. Levels of known NRF2 targets in the samples were examined by measuring NAD(P)H dehydrogenase, quinone 1 (NQO1) and glutathione-S-transferases (GST) enzyme activities and total glutathione (GSH) levels in 13 pairs of primary NSCLC tumors and adjacent normal tissues. NQO1 and GST activity was increased in the tumors relative to corresponding activity in matched normal tissue (FIG. 3B and Table 4).

TABLE 4

| Patient# | PT-42 | PT-18* | PT-17* | PT-43 | PT-44 | PT-24 | PT-25 | PT-41 | PT-40 | PT-23* | PT-29* | PT-27 | PT-45 | Mean ± SEM |
|---|---|---|---|---|---|---|---|---|---|---|---|---|---|---|
| GSH Normal | 0.5 | 16.4 | 6.0 | 0.1 | 3.4 | 6.6 | 5.6 | 6.2 | 6.7 | 2.4 | 2.2 | 7.4 | 2.0 | 5.0 ± 1.1 |
| GSH Tumor | 0.6 | 24.4 | 0.4 | 16.8 | 20.0 | 7.3 | 31.5 | 9.6 | 32.3 | 44.8 | 22.6 | 22.2 | 35.9 | 20.6 ± 3.7* |
| NQO1 Normal | 3.6 | 28.6 | 17.1 | 5.7 | 5.2 | 4.3 | 5.7 | 12.9 | 3.8 | 23.3 | 14.3 | 23.3 | 20.0 | 12.9 ± 2.4 |
| NQO1 Tumor | 3.3 | 1.0 | 22.9 | 8.6 | 26.2 | 34.8 | 22.4 | 68.1 | 21.9 | 3.8 | 51.4 | 135.2 | 171.0 | 43.9 ± 14.6‡ |
| GST Normal | 15.6 | 23.4 | 18.8 | 5.2 | 12.0 | 25.0 | 22.9 | 18.8 | 16.7 | 37.0 | 24.0 | 21.9 | 31.8 | 21.0 ± 2.2 |
| GST Tumor | 6.3 | 40.6 | 19.8 | 14.1 | 20.3 | 45.3 | 32.3 | 23.4 | 42.7 | 99.0 | 81.3 | 27.1 | 23.4 | 36.6 ± 7.3‡ |

*Patients whose tumors had somatic mutations. Total GSH is expressed as umol/mg protein. Data for NQO1 and GST is expressed as nmol DCPIP reduced/min/mg protein and nmol of product formed/min/mg protein respectively.
*$\rho < 0.005$;
‡±$\rho < 0.05$ (paired t_test)

Figure 3C:
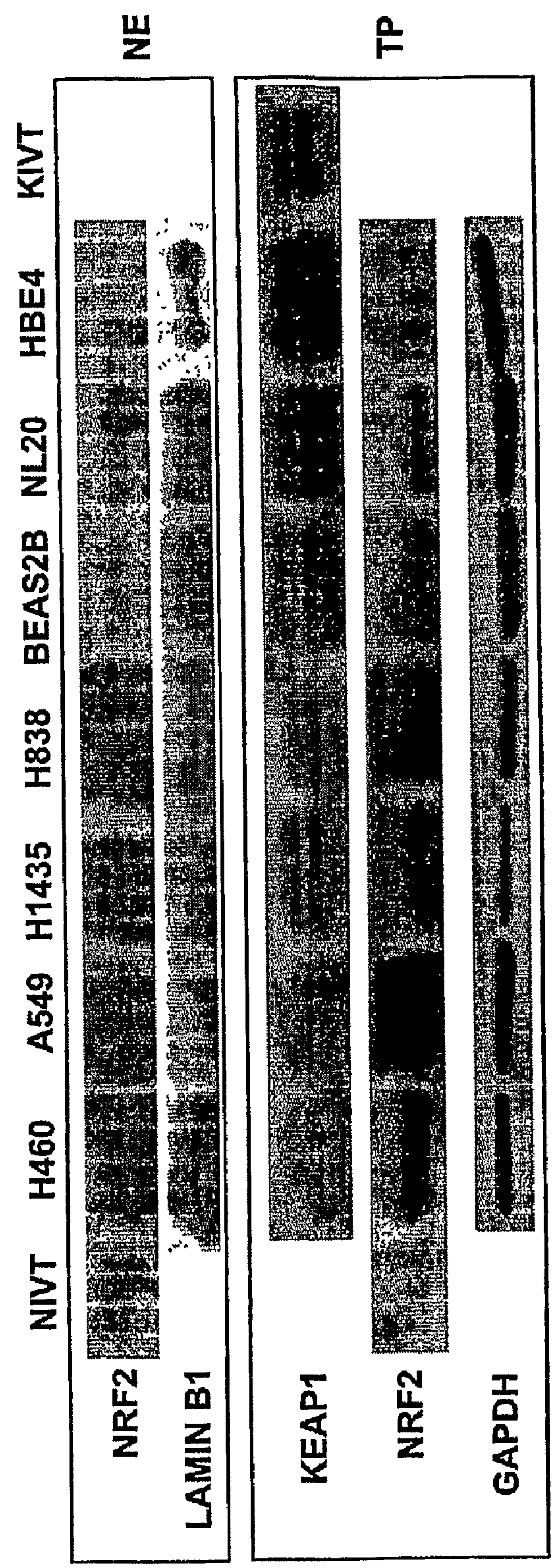

To determine gene expression values for the different normal and cancer cell lines, the relative fold-changes for individual cell lines were normalized to the maximum fold-change value across all cell lines for a particular gene. These studies showed that total glutathione activity was significantly higher in tumor tissues (FIG. 3B). To determine whether KEAP1 mutation correlated with NRF2 activation, immunoblot analysis was used to study the nuclear accumulation of NRF2. As shown in FIG. 3C, the cancer cells demonstrated an increased nuclear accumulation of NRF2 as well as an increase in total NRF2 (FIG. 3C). NAD(P)H dehydrogenase, quinone 1 (NQO1) and glutathione reductase 1 (GSR) enzyme activities and GSH levels were significantly higher in cancer cells. Total glutathione activity in H1435 and H838 was higher, whereas GST activity in A549 and H460 was similar to values from normal cells (FIGS. 4A-4D). GSH and related detoxification enzymes, including GS-conjugating efflux pumps, are involved in the detoxification of antineoplastic drugs and byproducts of oxidative stress. Table 5 below summarizes these results. Up-regulation of GSH and related enzymes in tumor tissues likely contributes to the observed high resistance to cytotoxic drugs and cell death (Soini Y et al., *Cancer* 92: 2911 (2001)).

TABLE 5

| Gene | KEAP1 | NRF2 | NQO1 | QSR | GCLC | GCLM |
|---|---|---|---|---|---|---|
| H460 | 2.29 ± 0.008 | 1.74 ± 0.017 | 20.15 ± 0.154 | 2.49 ± 0.015 | 0.77 ± 0.012 | 2.63 ± 0.027 |
| A549 | 0.50 ± 0.001 | 0.91 ± 0.000 | 23.89 ± 0.093 | 3.64 ± 0.012 | 3.64 ± 0.069 | 4.90 ± 0.085 |
| H1435 | 0.30 ± 0.005 | 1.18 ± 0.003 | 32.89 ± 0.193 | 7.02 ± 0.045 | 1.005 ± 0.294 | 4.31 ± 0.005 |
| H838 | 0.24 ± 0.000 | 0.66 ± 0.001 | 12.61 ± 0.062 | 1.79 ± 0.010 | 1.35 ± 0.035 | 5.90 ± 0.173 |
| BEAS2B | 1.00 ± 0.001 | 1.00 ± 0.001 | 1.00 ± 0.011 | 1.00 ± 0.001 | 1.00 ± 0.009 | 1.00 ± 0.005 |
| NL20 | 1.43 ± 0.001 | 1.33 ± 0.002 | 6.55 ± 0.000 | 1.46 ± 0.017 | 0.11 ± 0.001 | 1.25 ± 0.007 |

TABLE 5-continued

| HBE4 | 1.58 ± 0.004 | 1.63 ± 0.004 | 7.0 ± 0.082 | 1.34 ± 0.035 | 1.15 ± 0.050 | 1.67 ± 0.080 |
|---|---|---|---|---|---|---|

| Gene | GSTA2 | GSTA3 | PRDX1 | MRP1 | MRP2 |
|---|---|---|---|---|---|
| H460 | 0.02 ± 0.000 | 6.45 ± 0.007 | 6.91 ± 0.141 | 1.28 ± 0.004 | 681.40 ± 382.725 |
| A549 | 1.81 ± 0.004 | 0.45 ± 0.005 | 5.08 ± 0.080 | 3.07 ± 0.005 | 907.60 ± 431.769 |
| H1435 | 6.75 ± 0.007 | 4.25 ± 0.080 | 5.91 ± 0.055 | 1.44 ± 0.002 | 200.00 ± 499.295 |
| H838 | 0.06 ± 0.000 | 3.22 ± 0.013 | 3.12 ± 0.010 | 1.56 ± 0.002 | 297.00 ± 14.148 |
| BEAS2B | 1.00 ± 0.001 | 1.00 ± 0.001 | 1.00 ± 0.005 | 1.00 ± 0.001 | 1.00 ± 0.758 |
| NL20 | 1.25 ± 0.001 | 1.92 ± 0.022 | 1.02 ± 0.004 | 1.15 ± 0.004 | 2.00 ± 1.273 |
| HBE4 | 0.90 ± 0.000 | 2.30 ± 0.029 | 1.20 ± 0.011 | 0.96 ± 0.014 | 2.80 ± 1.864 |

All relative fold changes were normalized to BEAS2B. Values represent Mean - SD of triplicate samples.

Figure 3D:
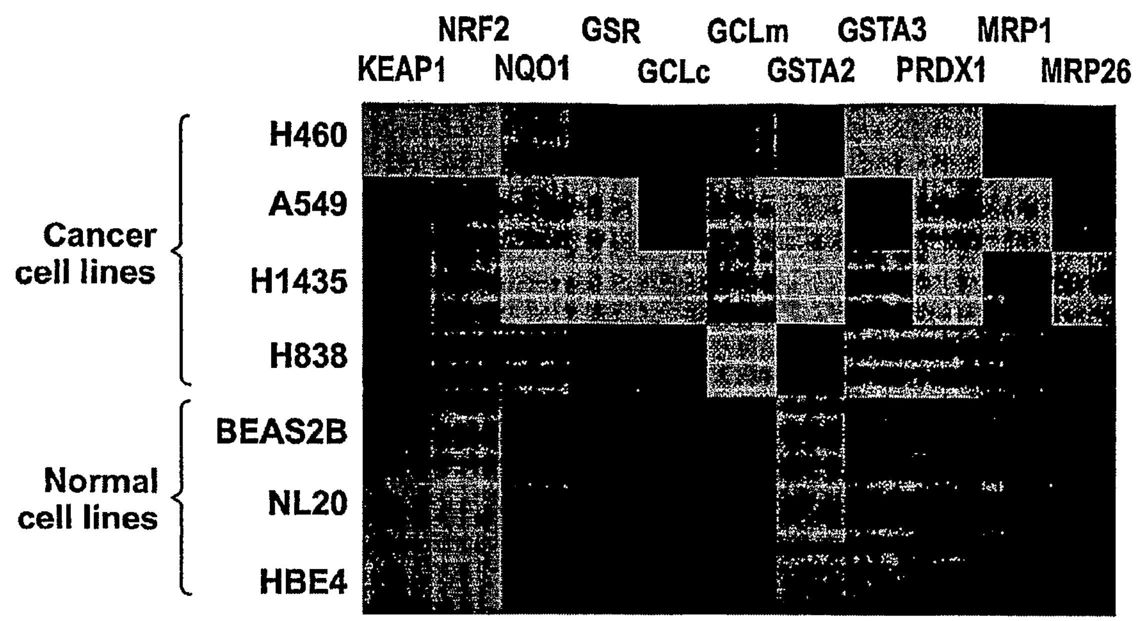

The mechanism contributing to the increased expression of cytoprotective enzymes in tumors was examined using 4 human NSCLC cell lines (H460, A549, H1435, and H838) and 3 non-malignant cell lines (BEAS2B, NL20, and HBE4). Real-time PCR analysis of the expression of NRF2, KEAP1, and various NRF2-dependent genes showed that transcript levels of the various NRF2-dependent antioxidant genes, detoxification enzymes, and drug efflux pump was up-regulated in cancer cells (FIG. 3D). Multidrug resistance associated protein 2 (MRP2), which is known to confer resistance against several chemotherapeutic drugs (Young L C et al. *Cancer Research* 7:1798 (2001)) showed very high levels of expression in cancer cells. Transcript levels of NRF2 did not differ significantly between normal and cancer cells. Expression of KEAP1 mRNA was down-regulated in 3 of the 4 NSCLC cell lines studied. As shown by immunoblotting, the expression of KEAP1 protein was also down-regulated in cancer cell lines (FIG. 3C).

Figure 3E:
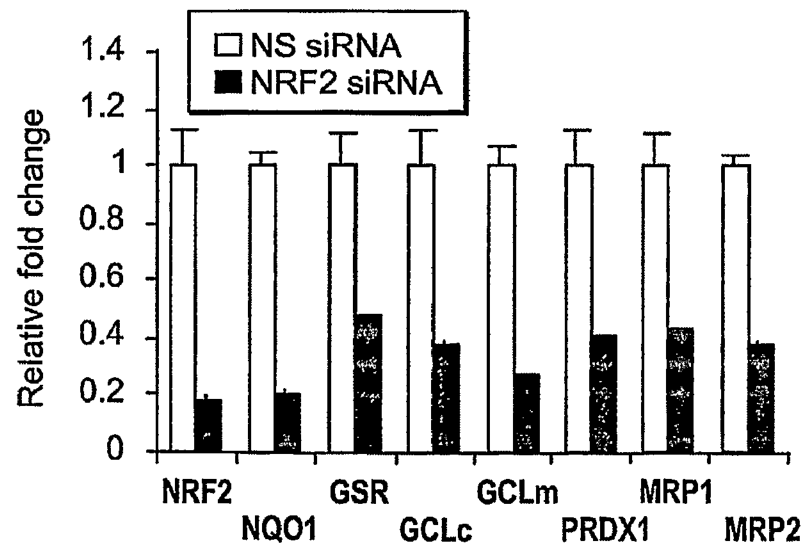
Figure 3F:
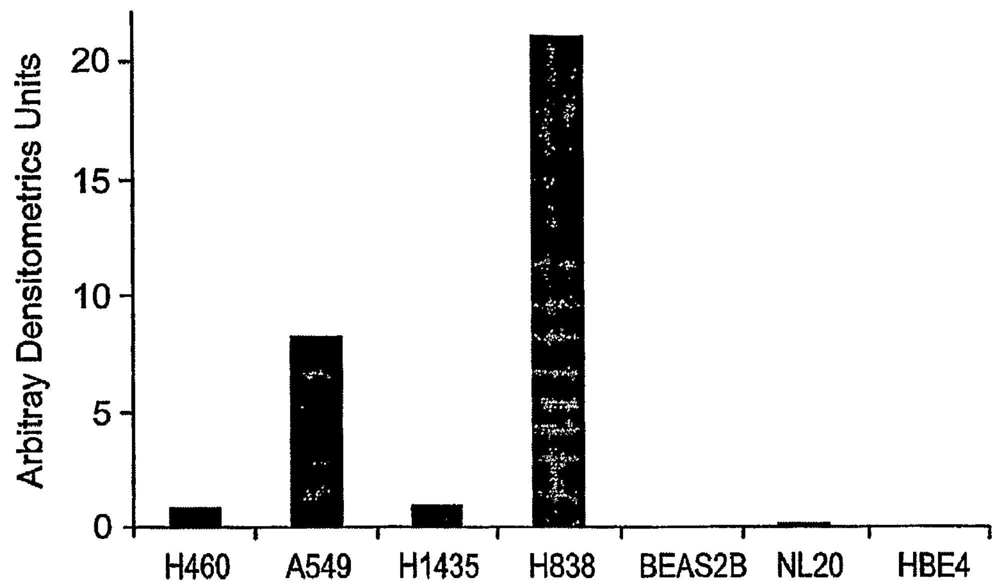
Figure 3G:
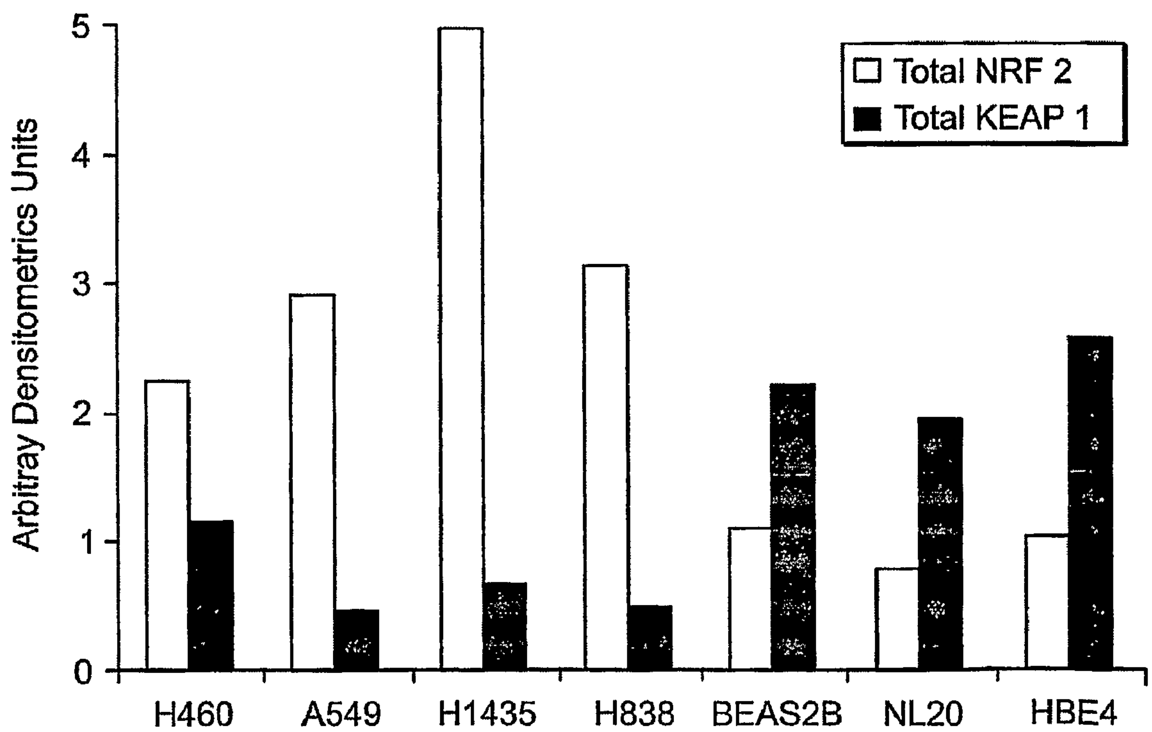
Figure 4:
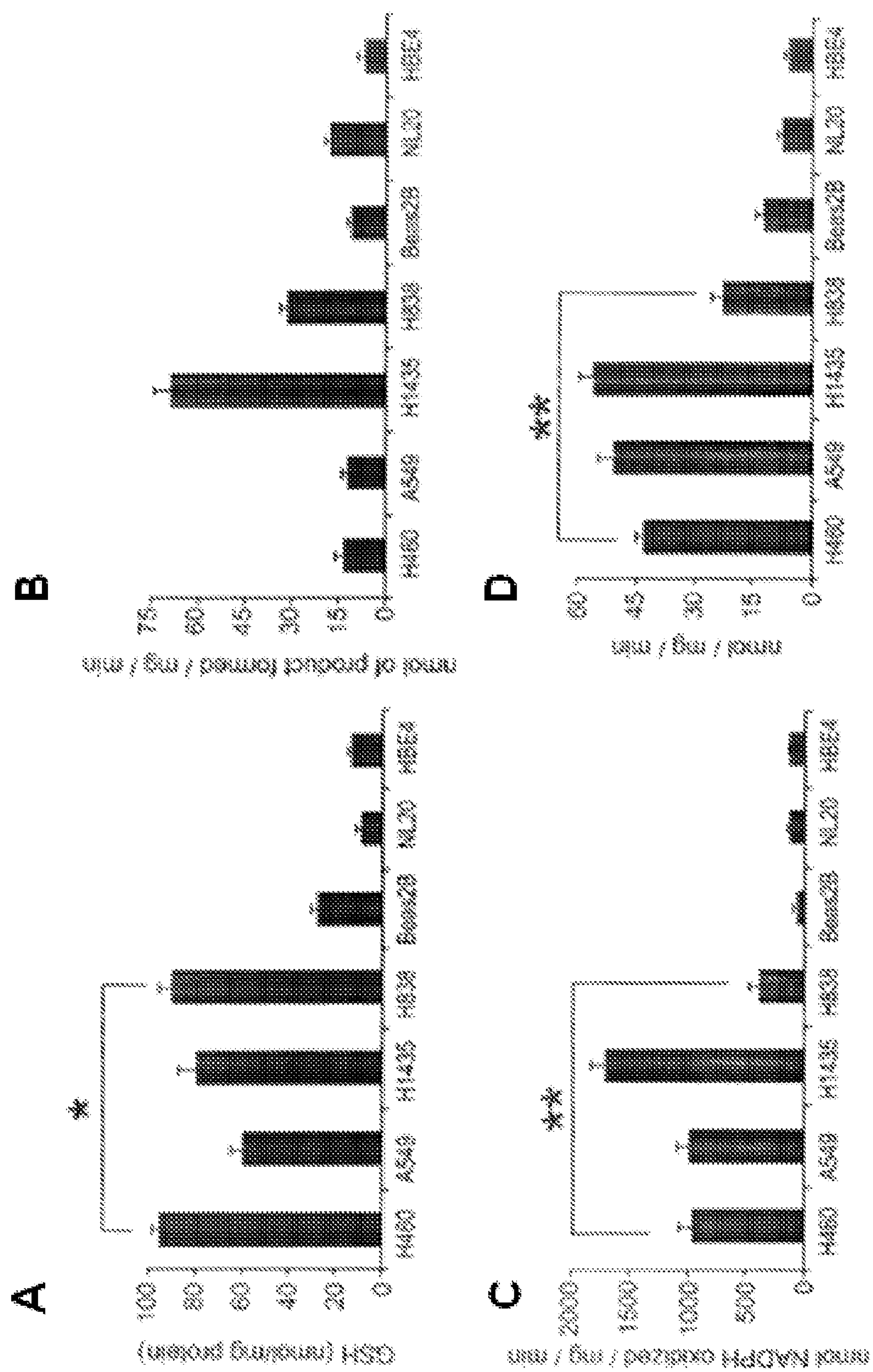
Figure 5:
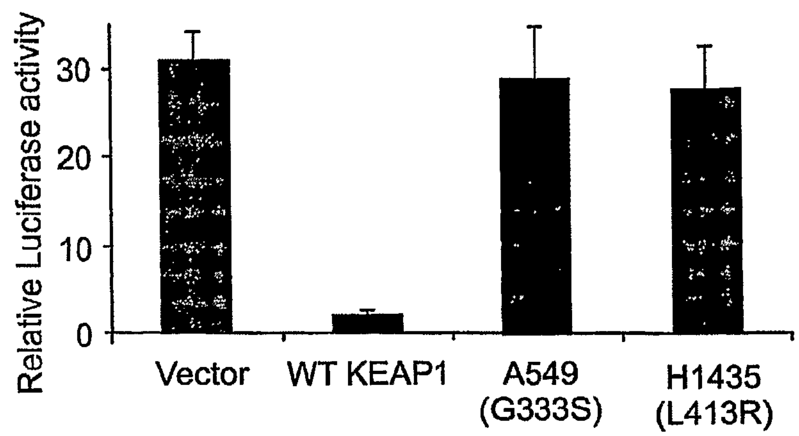

To determine the functional consequences of tumor-derived mutations on KEAP1 activity and resultant increases in NRF2, cDNAs harboring the same mutations seen in tumor cell lines A549 and H1435 were generated. The wild-type and mutant constructs of KEAP1 were transfected into H838 cells stably expressing an ARE reporter. Transfections with wild-type KEAP1 completely abolished ARE reporter activity, whereas overexpression of the mutant construct did not (FIG. 5). These results indicate that somatic mutations hamper the association between KEAP1 and NRF2 and consequently activate NRF2. The enhanced expression of various antioxidants and detoxification genes was shown to be NRF2-dependent because siRNA targeted against NRF2 transcript attenuated the expression of these NRF2-dependent genes in A549 cells (FIG. 3E).

Example 3

Identification of siRNAs Targeting Nrf2

A number of 19 base pair siRNA duplexes for the human Nrf2 gene were designed using publicly available software from sites such as Qiagen, Ambion and Invitrogen. The Nrf2 mRNA sequence (accession number: NM_006164) was downloaded from the National Center for Biotechnology Information database, and putative siRNA oligomers were identified using these publicly available siRNA design sites. A list of sequences generated using the programs of a three different siRNA design sites was generated. The sequences were compared, and siRNA sequences present on all three lists were selected for further characterization. The selected sequences were used in a BLAST comparison against the human genome database. Only the sequences specifically targeting Nrf2 mRNA were selected, as described by SEQ ID NO: 1, SEQ ID NO: 2, SEQ ID NO:3, SEQ ID NO:4 below: All of the siRNA duplexes were synthesized by Dharmacon Research, Inc.

Position in Nrf2 mRNA sequence(NM_006164) for the siRNA duplex (ND1): 1686-1704

```
Sense strand siRNA:                  (SEQ ID NO: 1)
CUAGAGCAAGAUUUAGAUCUU

Antisense strand siRNA:              (SEQ ID NO: 5)
GAUCUAAAUCUUGCUCUAGUU
```

Position in Nrf2 mRNA sequence(NM_006164) for the siRNA duplex (ND3): 1903-1921

```
Sense strand siRNA:         (SEQ ID NO: 2)
GUAAGAAGCCAGAUGUUAAUU

Antisense strand siRNA:     (SEQ ID NO: 6)
UUAACAUCUGGCUUCUUACUU
```

Position in Nrf2 mRNA sequence(NM_006164) for the siRNA duplex (ND4): 1563-1581

```
Sense strand siRNA:         (SEQ ID NO: 3)
AUGAUGUCCAAAGAGCAGUUU

Antisense strand siRNA:     (SEQ ID NO: 7)
ACUGCUCUUUGGACAUCAUUU
```

Position in Nrf2 mRNA sequence (NM_006164) for the siRNA duplex (ND5): 1485-1463

```
Antisense Strand siRNA:              (SEQ ID NO: 4)
UUCAUCUCUUGUGAGAUGAGCCUCC

Sense strand siRNA:                  (SEQ ID NO: 8)
GGAGGCUCAUCUCACAGAGAUGAA
```

Figure 6:
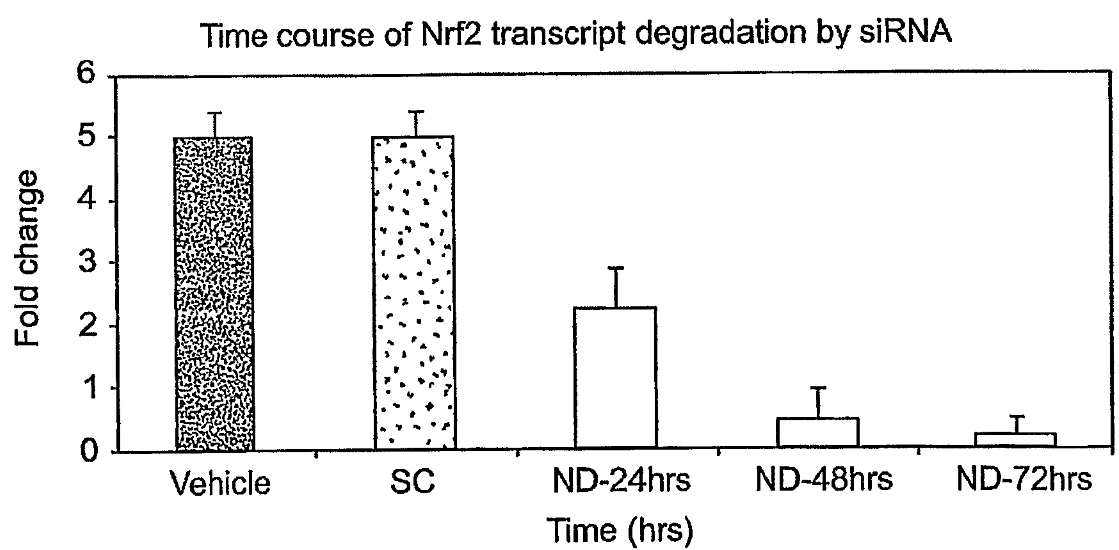
FIG. 6 is a graph showing Nrf2 transcript degradation over time following the transfection of A549 cells with Nrf2 siRNA (ND), scrambled control siRNA (SC), or vehicle control. Transcript degradation is measured by real-time PCR, and represented as fold-change.
Figure 7:
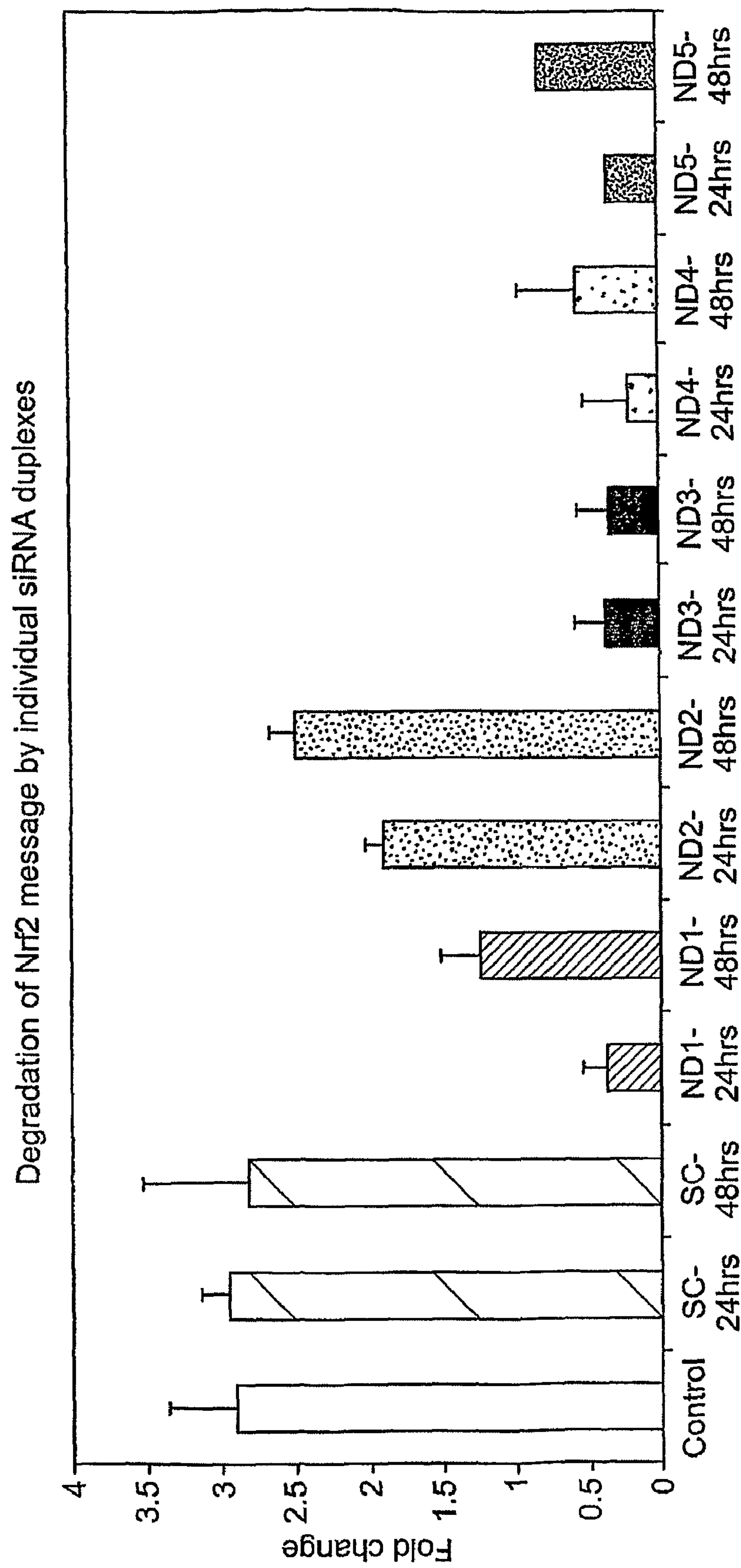
FIG. 7 is a graph showing Nrf2 transcript degradation over time following the transfection of A549 cells with Nrf2 siRNA (ND), scrambled control siRNA (SC), or vehicle control. Individual Nrf2 siRNA duplexes are represented as ND1, ND2, ND3, ND4, and ND5. Transcript degradation is measured by real-time PCR, and represented as fold-change.
Figure 7A:
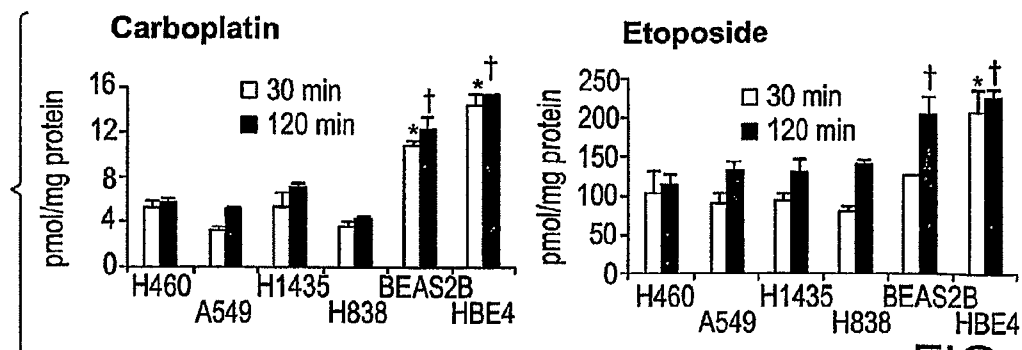
Figure 7B:
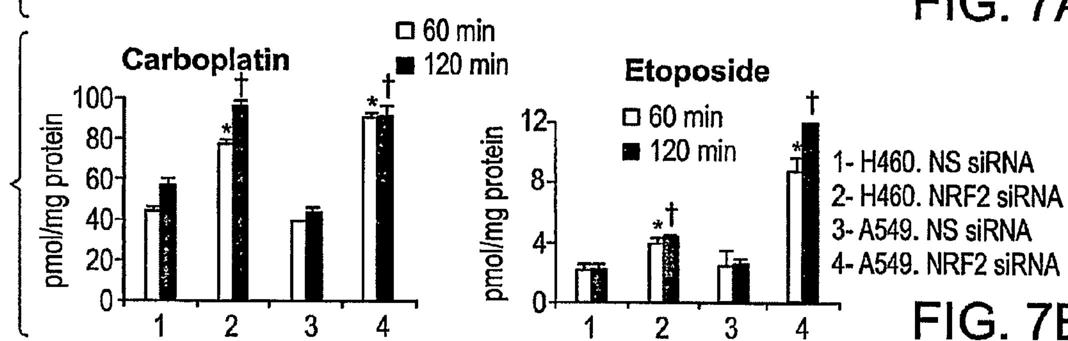
Figure 7C:
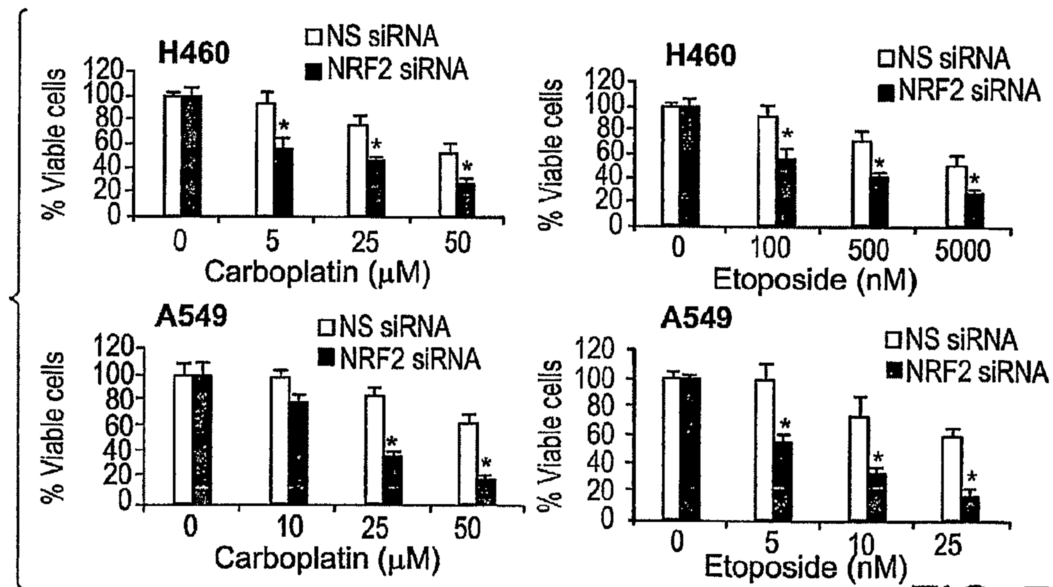
Figure 7D:
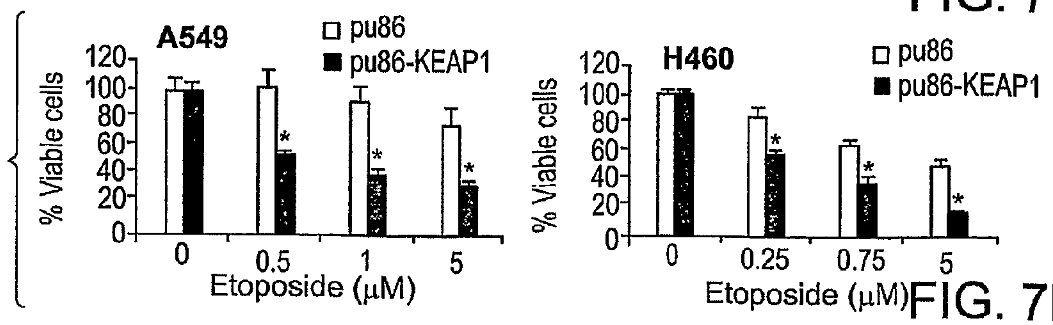

To study the degradation of Nrf2 mRNA with siRNA in a time dependent manner, a pooled mixture of the generated duplexes were transfected into A549 human non-small cell lung carcinoma cell line. As a control, a non-specific scrambled siRNA duplex (SC) was used. Transfection vehicle alone was also used as control. Total RNA was isolated after 24, 48 and 72 hours. The amount of Nrf2 transcript was measured using real time TAQMAN PCR. FIG. 6 shows that Nrf2 message in the pooled Nrf2 siRNA transfected cells decreased significantly over time. Based on the results from these experiments, five siRNA duplexes for Nrf2 (indicated as ND1, ND2, ND3, ND4, and ND5) were selected which showed maximum silencing. These five ND duplexes were again screened using the same assay to measure amount of Nrf2 transcript as described above. The results are shown in FIG. 7. All of the Nrf2 siRNA duplexes employed in the assay displayed some degree of degradation of Nrf2 message after 24 and 48 hours. The ND1, ND3, ND4 and ND5 appear to be the most potent siRNA duplexes, with the Nrf2 siRNA duplex designated as ND3 displayed maximum message degradation after 24 and 48 hours.

Example 4

Altered Expression of Nrf2 and KEAP1 Effects Chemoresistance

In this example, the effect of Keap1 and Nrf2 on the chemoresistance of various cancer cells is described.

The high antioxidant capacity of NSCLC cells increases cell survival and proliferation and protects against oxidants, radiation, and chemotherapies, thus conferring the intrinsic chemoresistance phenotype (Tew K D *cancer Res* 54:4313 (1994); Soini Y, et al. *Cancer* 92:2911 (2001)). Levels of GSH-conjugating enzymes are higher in cell lines derived from NSCLC cells than in small-cell lung cancer cell lines D'Arpa P, et al, *Biochim Biophys Acta* 989: 163 (1989)). These alterations may account for the differences in drug sensitivity between these tumor types (Gottesman MM *Ann Rev Med* 53:615 (2002)). Several studies have documented that glutathione concentrations are high in drug-resistant cancer cell lines and that cell viability can be modulated with buthionine sulfoximine, which causes glutathione depletion (Rudin C M, et al., *Cancer Res* 63: 312 (2003); Hamilton D et al. *Curr Oncol Rep* 6, 116 (2004)).

To elucidate the role of NRF2 in chemoresistance, the accumulation of radiolabeled carboplatin ($^{14}$C) and etoposide ($^{3}$H) was compared in normal lung epithelial cells and cancer cells using the following methods. Cells transfected with NRF2 siRNA and control NS siRNA were seeded at a density of $0.3\times10^{6}$ cells/ml in 6-well plates. After 12 hours, growth medium was aspirated and replaced with 1.5 ml of RPMI 1640 containing 0.2 μM of [$^{3}$H]Etoposide (646 mCi/mmol; Moravek Biochemicals) and [$^{14}$C] Carboplatin (53 mCi/mmol; Amersham Biosciences). Cells were incubated with radiolabeled drug for the indicated period of time and then cooled on ice, washed four times with ice-cold PBS, and solubilized with 1.0 ml of 1% SDS. The radioactivity in each sample was determined by scintillation counting. Results are presented as means±standard deviation (SD). Drug accumulation was higher in normal cells (~1.5- to 2-fold; FIG. 8A). Cancer cells transfected with NRF2 siRNA accumulated 2 to 3 times as much of the drugs as did cells treated with non-targeting NS siRNA (FIG. 8B) indicating that NRF2 functions in the regulation of drug detoxification. The drug-resistant phenotype of A549 and H460 cells was also analyzed to determine the influence of NRF2 siRNA on drug sensitivity. As shown in FIGS. 8C and 8D, silencing of NRF2 by siRNA in cancer cells enhanced the sensitivity of these cells to etoposide and carboplatin. Alternatively, expression of wild-type KEAP1 cDNA in A549 and H460 cells partially abolished the drug-resistant phenotype of these cells and restored the sensitivity of these cells to etoposide (FIG. 8D and FIG. 8E). Increased drug accumulation and enhanced sensitivity to etoposide and carboplatin in cancer cells with reduced levels of NRF2 indicated that NRF2 contributes to drug resistance by regulating the expression of several plasma membrane efflux pumps, such as MRP1 and MRP2, and Phase II detoxification enzymes.

These results demonstrate that altered expression of Keap1 and Nrf2 effects chemoresistance, and when Nrf2 expression is decreased, a cell becomes more sensitive to chemotherapeutics.

Example 5

Degradation of Nrf2 Sensitizes Cancer Cells to Chemotherapeutic Agents

In this example, Nrf2 siRNA-directed degradation of Nrf2 sensitization of cancer cells to chemotherapeutic agents is described.

Nrf2 siRNA duplexes were shown to be effective in degrading the Nrf2 message over time in cancer cells. Because Nrf2 is considered a master regulator of detoxification enzymes and multidrug resistance proteins, and because over-expression of Nrf2 has been shown to be associated with the malignant phenotype (Hayes J D et al. 2006), regulation of Nrf2 expression likely represents a means to alter the drug sensitivity of a cell. The effect of Nrf2 siRNA on the killing of A549 non-small cell lung cancer cells was examined using cisplatin, a widely used anticancer drug using the following methods.

Figure 9A:
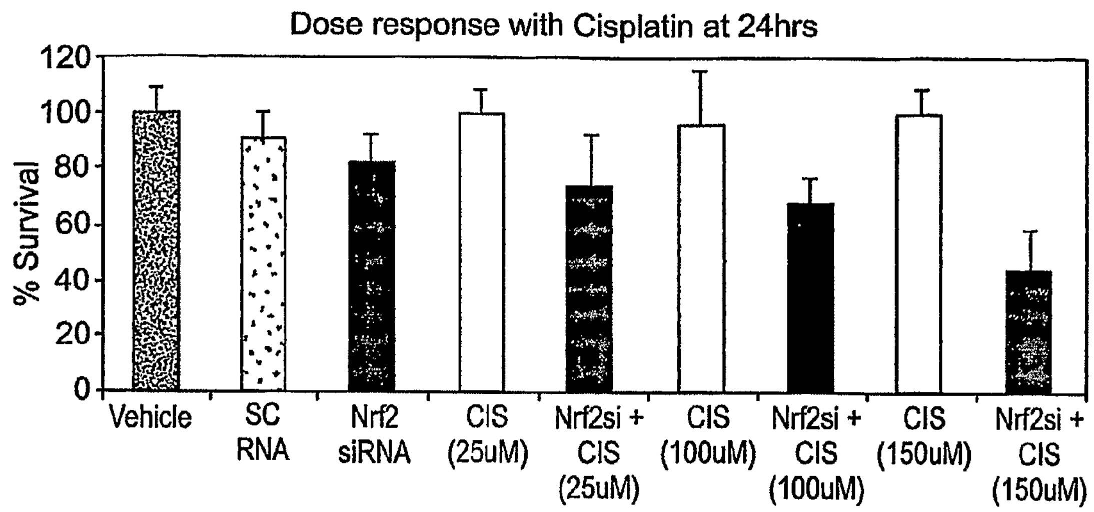
FIGS. 9A and 9B are graphs showing that silencing of Nrf2 sensitizes A549 cells to cisplatin.
Figure 9B:
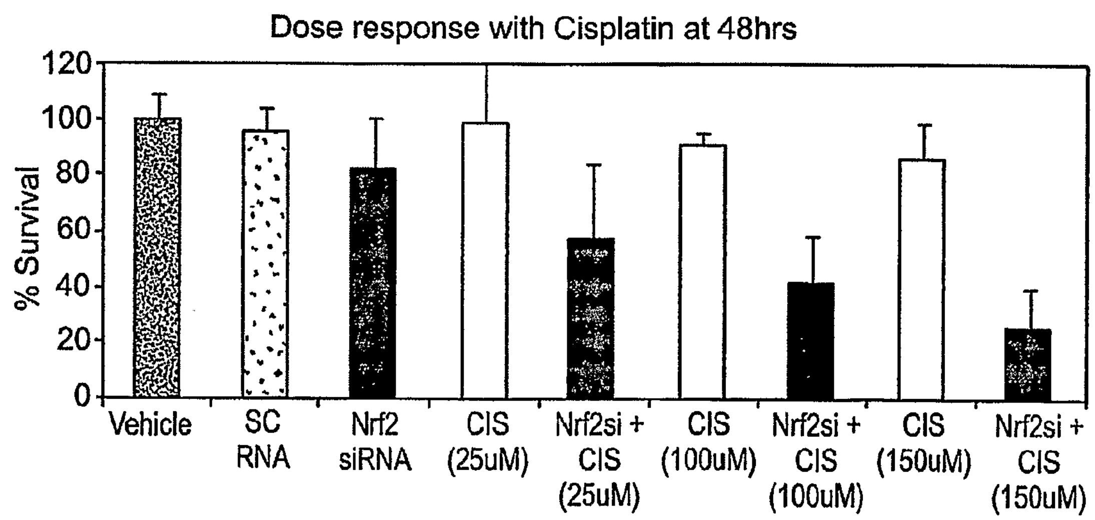

Briefly, 10,000 cells were grown in a 96 well plate for 24 hours, and transfected with Nrf2 siRNA (ND siRNA) or a non-specific scramble duplex control siRNA (SC siRNA). After 24 hours, cisplatin was added at a range of doses (0-100 μM). After 24 or 48 hours cell proliferation was quantified using the CELL TITER 96 Aqueous Assay Kit (Promega), and then expressed as percent survival over control. FIG. 9A shows the percent cell survival after 24 hours, and FIG. 9B shows the percent cell survival after 48 hours. The results of FIGS. 9A and B show A549 cells that have been transfected with Nrf2 siRNA, and therefore have decreased expression of the Nrf2 master regulator, show increased sensitivity to treatment with cisplatin at concentrations ranging from 25-100 μM. Cells that appear to have been resistant to cisplatin treatment when treated with just the chemotherapeutic agent alone, become sensitive to treatment with the agent when combined with the Nrf2 siRNA duplexes.

Figure 10:
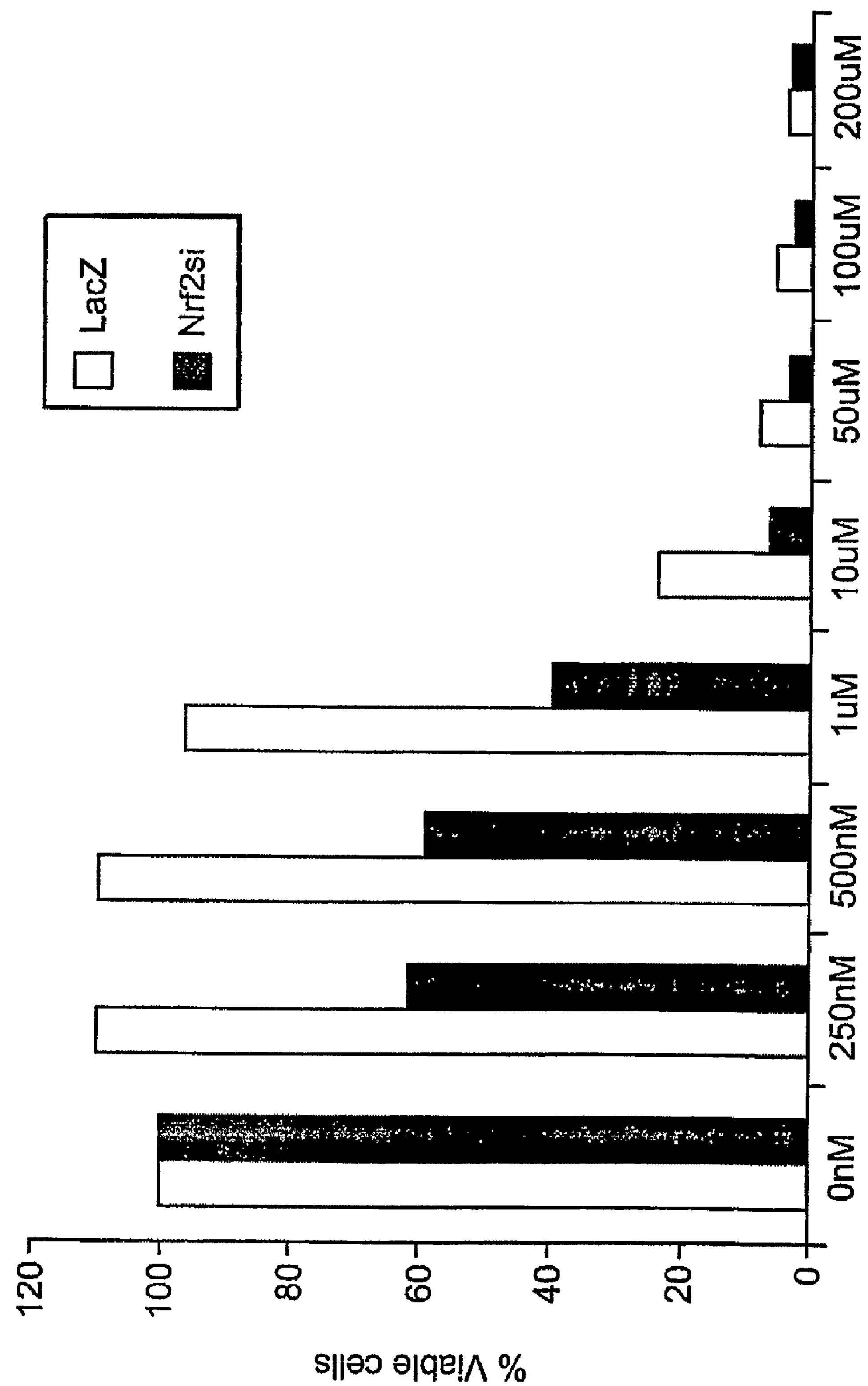
FIG. 10 is a graph showing that silencing of Nrf2 sensitizes cancer cells to etoposide. The renal carcinoma cell line Renca was stably transfected with Nrf2 siRNA (dark bars) or non-specific LacZ siRNA (light bars), and treated with etoposide at a range of concentrations. Cell viability is indicated on the Y-axis, measured using the MTT assay, after 48 hours.

The effect of Nrf2 siRNA on the killing of Renca renal carcinoma cells was examined using etoposide, another widely used anticancer drug. To generate stable Renca cell lines that over-expressed Nrf2 siRNA and non-specific scramble siRNA (SC siRNA), the siRNA sequence was converted into short hairpin RNA (shRNA) and cloned in to a BLOCK-IT U6 RNAi Entry Vector (Invitrogen). The shRNA construct was packaged into a lentiviral vector, and transduced into Renca cell lines. Recombinants were selected with antibiotic. Renca cells stably expressing Nrf2 siRNA and non-specific LacZ siRNA were screened, and two clones expressing Nrf2 siRNA showing maximum knockdown of Nrf2 message were selected for further characterization. A cell viability assay was performed using these clones using etoposide as the chemotherapeutic drug. Briefly, 10,000 cells were plated in 96 well plates and exposed to concentrations of etoposide ranging from 1-200 μM. Cell viability was measured using the MTT [3-(4,5-dimethylthiazol-2-yl)-2,5-diphenyltetrazolium bromide] assay after 48 hours. Briefly, cells were transfected with 50 nM siRNAs two times within a 48 h interval and, 24 hours after the second transfection, cells were plated at a density of 7,500 cells/well in 180 μl of growth media in 96-well plates. After 6 hrs incubation at 37° C., cells were treated with various concentrations of chemotherapeutic agents. After 96 h, drug cytotoxicity was evaluated by using a 3-(4,5-dimethylthiazol-2-yl)-2,5-diphenyl tetrazolium bromide (MTT; Sigma) reduction conversion assay. The results are shown in FIG. 10. Renca cells expressing Nrf2 siRNA were more susceptible to etoposide induced cell death than the LacZ expressing control cells. Etoposide concentrations as low as 250 μM, while ineffective on Renca cells expressing LacZ (~100% viable cells), kill Renca cells in which the Nrf2 regulator has been silenced, such that viability decreases to –60%.

Taken together, this data demonstrated that Nrf2 siRNA-directed degradation of Nrf2 sensitizes cancer cells to chemotherapeutic agents.

Example 6

Alteration of Nrf2 In Vivo Affects the Growth of Cancer Cells

In this example, over-expression of Nrf2 was shown to promote the growth of cancer cells. Further, the use and effectiveness of Nrf2 siRNA oligomers in vivo was demonstrated.

First, to study the effect of Nrf2 over-expression in cancer cells, Nrf2 cDNA was cloned into the pUB6/V5-His vector and then transformed in to Renca cells. Renca transformants that stably overexpressed Nrf2 cDNA were screened by Real Time PCR. Two clones that showed a 3-fold increase in expression of the Nrf2 message were selected.

Figure 11:
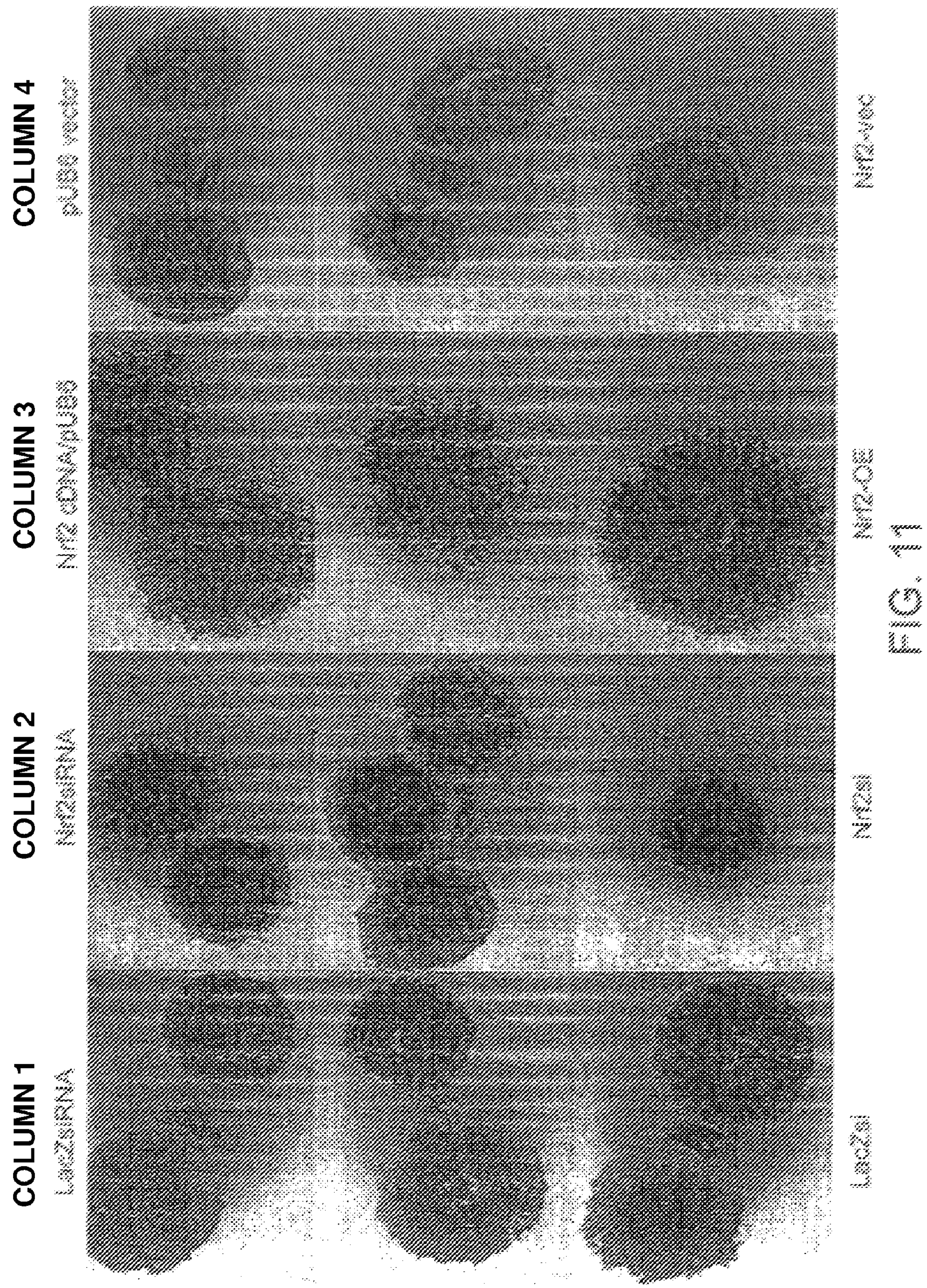
FIG. 11 provides twelve panels showing photographs of colonies formed by Renca cells stably transfected with Nrf2 siRNA, LacZ siRNA control, Nrf2 cDNA, or vector control, in colony formation assay. Column 1 shows LacZ siRNA control cells. Column 2 shows Nrf2 siRNA transfected cells. Column 3 shows cells that overexpress Nrf2 cDNA. Column 4 shows cells transfected with empty vector as control.

To study the effect of Nrf2 knockdown or Nrf2 over-expression on proliferation and colony formation, a colony formation assay was carried out. Briefly, 500 cells were plated in a 10 cm tissue culture dish. After 12 days of incubation, the colonies were stained with crystal violet to visualize viable colonies. Colonies were measured, counted and recorded. FIG. 11 shows that Renca cells stably expressing Nrf2 cDNA (column 3) formed the largest colonies as compared to those cells stably expressing LacZ siRNA control (column 1), Nrf2si RNA (column 2), or vector control (column 4). Thus, over-expression of the master regulator Nrf2 increased the size of colonies formed, while Nrf2siRNA expression decreased the colony size.

Example 7

Nrf2 siRNA Reduced Nrf2 Expression In Vivo

Figure 12A:
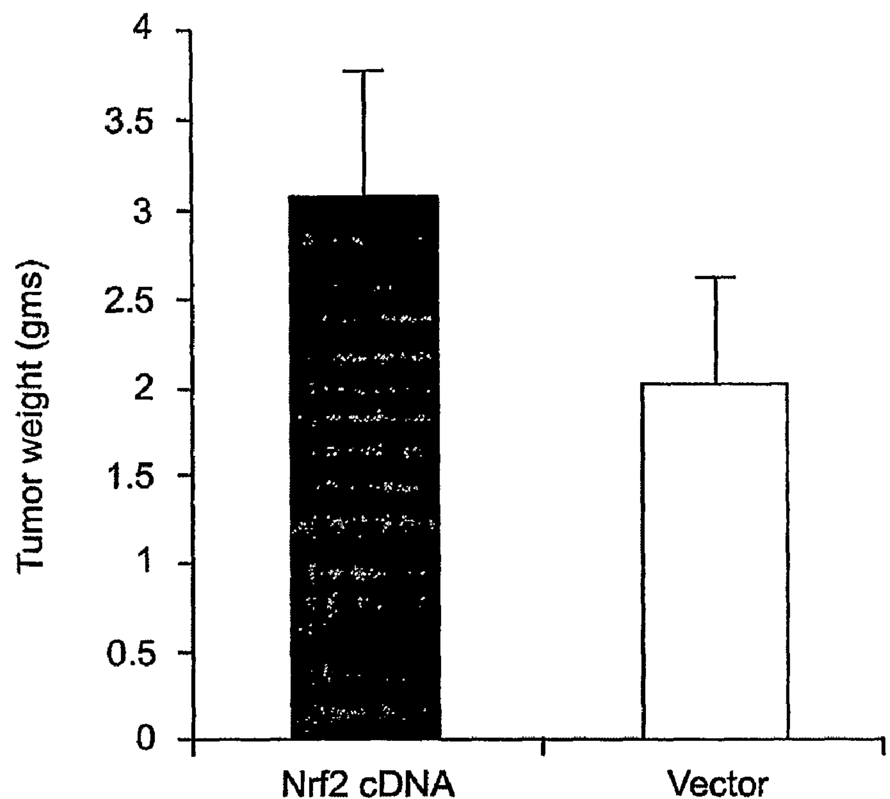
FIGS. 12A and 12B are graphs showing that cells over-expressing Nrf2 have increased tumor volume and weight when grown in a nude mouse model. Renca cells over-expressing Nrf2 or vector alone were implanted into Balb/c mice.
Figure 12B:
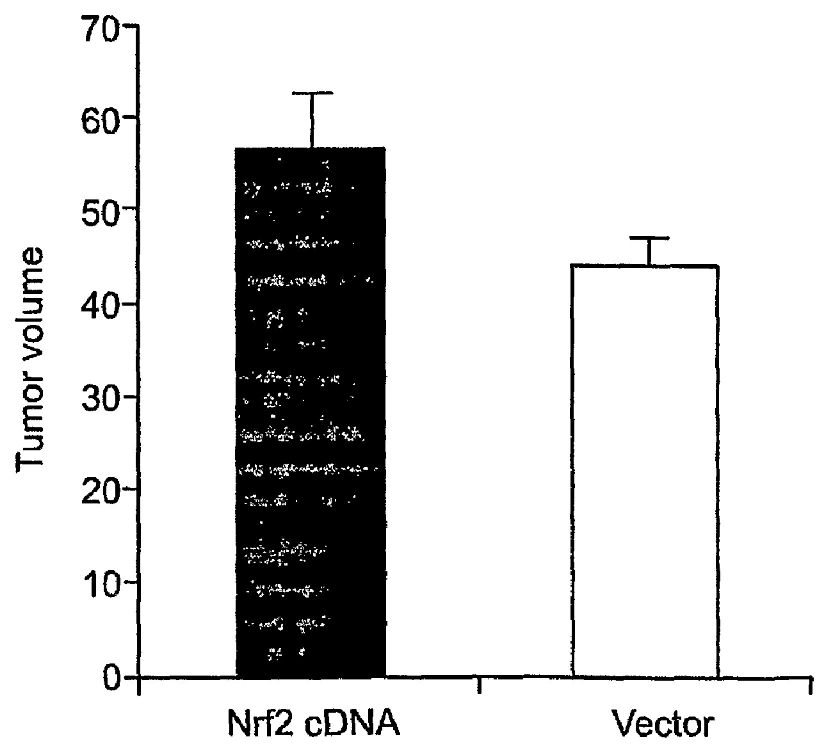

To further study the effect of Nrf2 over-expression in cancer, Renca cells over-expressing Nrf2, which were described above, were injected into Balb/c mice. The Balb/c mice (6-8 weeks of age) were divided into two groups of ten mice each and injected with Renca cells over-expressing Nrf2 or a control vector. Injection of $5\times10^5$ cells was made in a flank incision into the subscapular space of the left kidney after anesthetization of the animals. Four weeks after injection, the mice were sacrificed to determine the weight and volume of the primary tumor in the kidney, and assessment of metastases in the lungs. FIGS. 12A and 12B show the total weight and the total volume, respectively, of the primary tumor in the kidney was significantly higher in mice injected with Renca cells expressing Nrf2 cDNA.

Figure 13A:
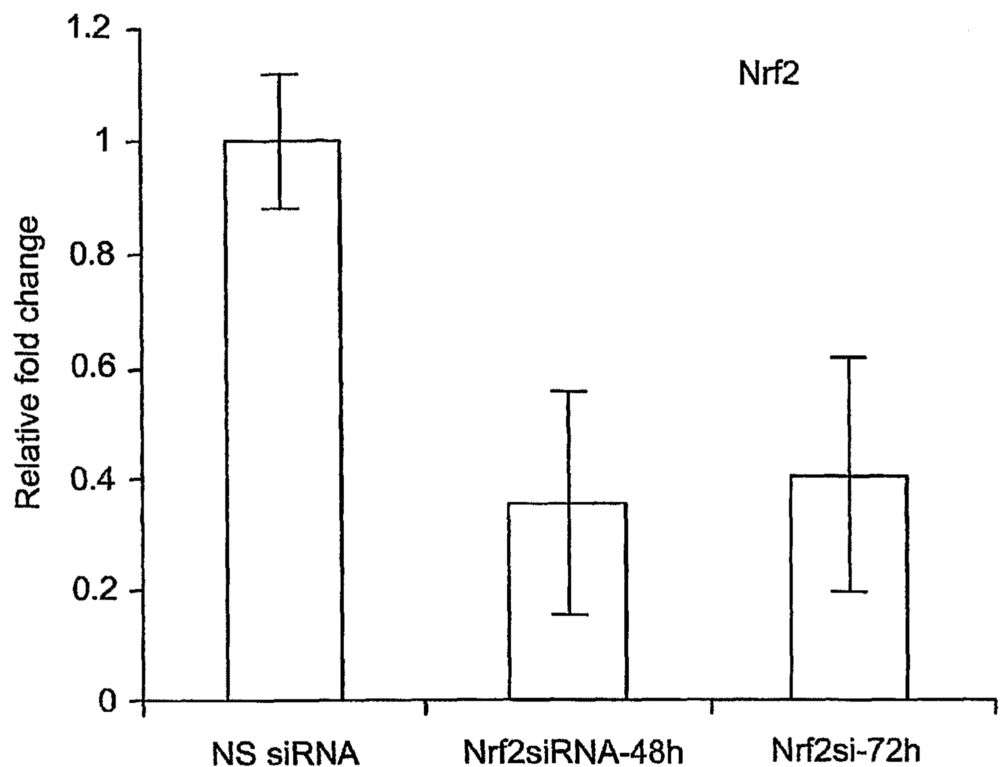
FIGS. 13A and 13B are graphs showing the results of in vivo studies using siRNA oligomers. C57 mice were injected with siRNA oligomers that target Nrf2 or with NS control siRNAs, and the relative fold change in Nrf2 and glutamate-cysteine ligase modifier subunit (GCLm) expression after 48 and 72 hours was measured by RT PCR and indicated on the y-axis.
Figure 13B:
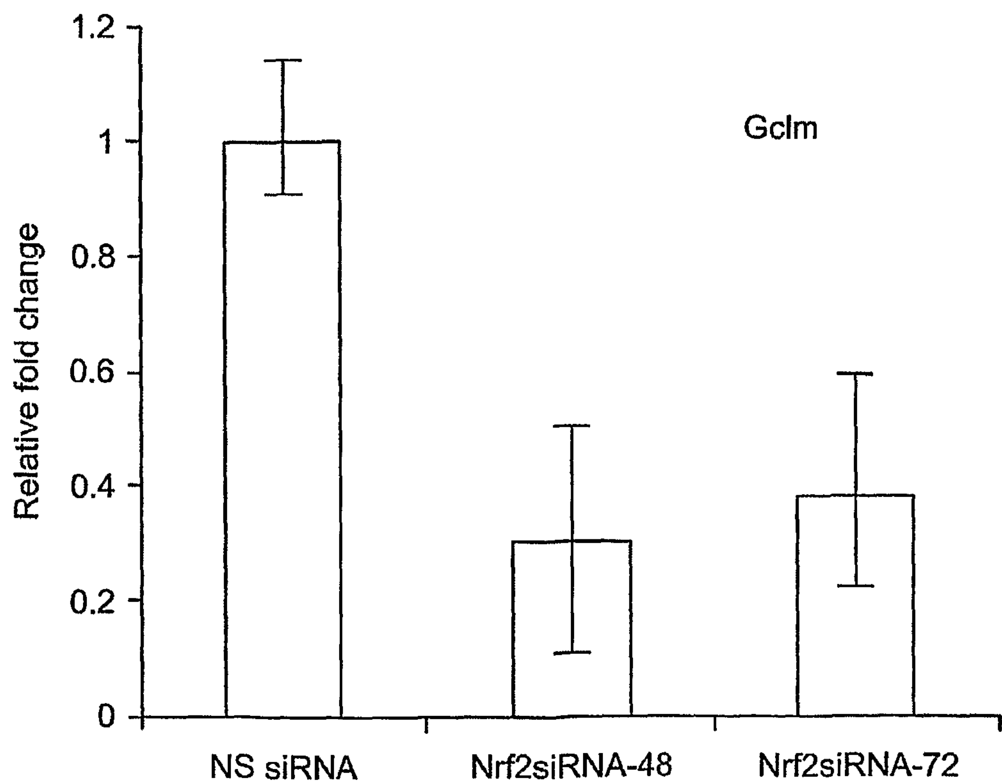

The effect of knockdown of Nrf2 was then examined in vivo. C57 mice were injected with 50 μg of siRNA corresponding to Nrf2 or the NS control oligomers. Mice were sacrificed 48 or 72 hours following injection, and the relative fold change in Nrf2 or Gclm expression was determined using RT-PCR, FIG. 13A and FIG. 13B. These results showed that the Nrf2 oliogomers were effective in knocking down expression of Nrf2 in vivo by 50-60%, and therefore represent an attractive therapeutic option.

In summary, this data shows that over-expression of Nrf2 promoted the growth of cancer cells in vitro and in vivo, and that treatment with Nrf2 siRNA oligomers is effective in knocking down Nrf2 expression.

Example 8

Cell Based Assays for the Identification of Nrf2 Inhibitor

Figure 14:
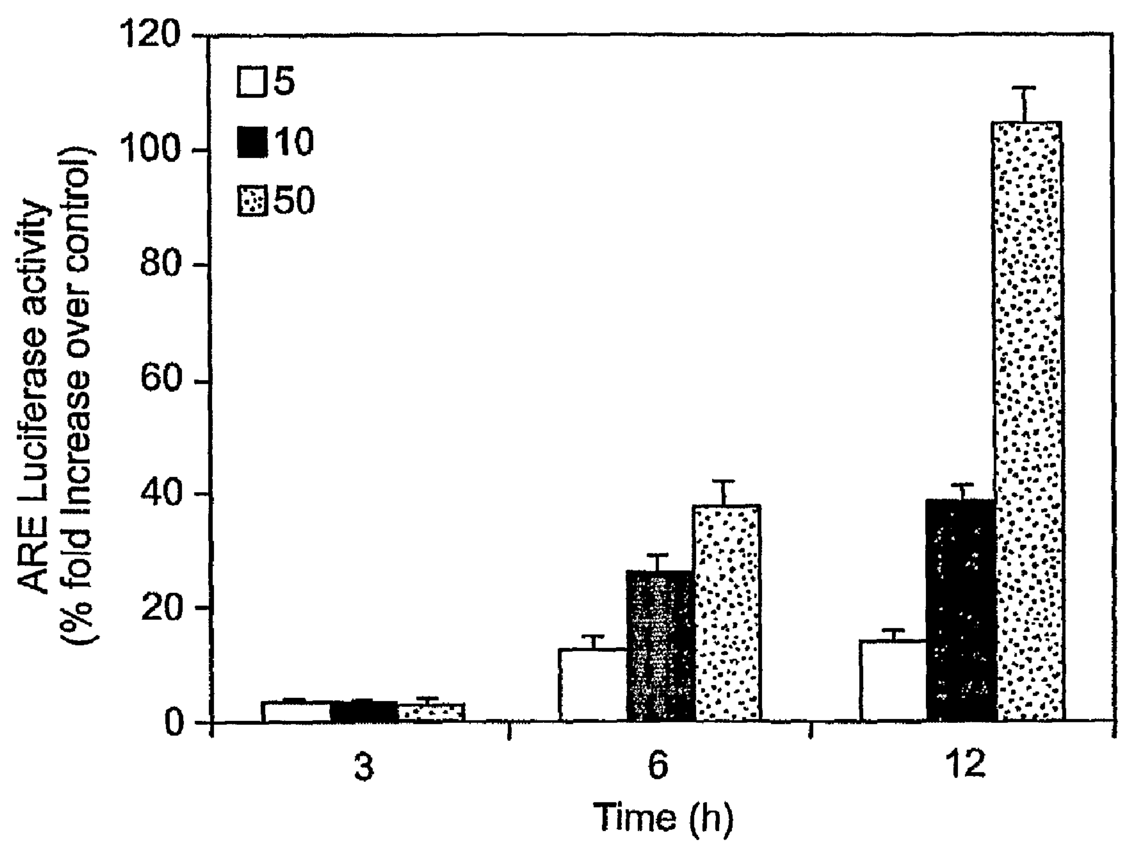
FIG. 14 is a graph depicting an increase in luciferase activity in Hepa cells stably transfected with pARE-luc, and treated with the Nrf2 activators sulforaphane and dibenzoylmethane (DBM) at a range of concentrations (5, 10, 50 μM). The data represent the mean plus or minus the standard deviation of percent increase over the control, as determined from three separate experiments.

In this example, a high throughput approach to screen different chemicals for their potency to inhibit Nrf2 activation is described. A cell based transcriptional reporter assay approach was used for the identification of agents that inhibit Nrf2 mediated transcription. Hepa cells, which are mice liver carcinoma cells, were stably transfected with the ARE-luciferase reporter vector, and plated on to 96 or 340 well plates. After overnight incubation, the cells were pretreated for 1-3 hours with different compounds, and challenged with a known Nrf2 activator, sulforaphane and dibenzoylmethane (DBM). Luciferase activity was measured after 6 hours following the last treatment using a commercially available system. The increase in luciferase activity indicated the degree of Nrf2 activity. FIG. 14 is a graph illustrating the increase in luciferase activity in Hepa cells stably transfected with pARE-luc, and treated with the Nrf2 activator sulforaphane and dibenzoylmethane (DBM) at a range of concentrations (5, 10, 50 μM Various chemical libraries can be used for screening Nrf2 inhibitors, including Chembridge 1(CB01) and Chembridge 2 (CB02), and Spectrum 1(MSSP), both available at Johns Hopkins University.

The experiments reported herein were carried out using the following materials and methods.

Heat Maps

Heat maps were constructed using GeneCluster and Treeview software (Eisen lab, Stanford, Calif.). For displaying gene expression values for the different normal and cancer cell lines, the relative fold-changes for individual cell lines was normalized to the maximum fold-change value across all cell lines, for a particular gene.

Biochemistry

To obtain total protein lysates, cancer cells or tissues were lysed in 50 mM Tris pH 7.2, 1% Triton X-100 containing HALT Protease Inhibitor cocktail (Pierce Biotechnology, Rockford Ill.,) and centrifuged at 12,000 g for 15 minutes at 4° C. To obtain nuclear extracts, NE-PER Nuclear extraction reagents (Pierce Biotechnology) were used. Protein concentrations were estimated by the BCA method (Pierce Biotechnology).

For immunoblot analysis, 30 μg and 100 μg protein from nuclear extracts and total protein lysates, respectively were used and resolved on 10% SDS-PAGE gels. Proteins were transferred onto PVDF membranes and the following antibodies were used for immunoblotting: KEAP1 (gift from M. Velichkova, University of California at San Diego, La Jolla, Calif.), NRF2 (H-300; Santa Cruz), Lamin B1 (Santa Cruz Biotechnology, Santa Cruz, Calif.), and GAPDH (Imgenex, San Diego, Calif.). All primary antibodies were diluted in PBS-T/5%/non fat dry milk and incubated overnight at 4° C.

Enzyme activities of GST, GSR and NQO1 were determined in the total protein lysates by following methods as described and known in the art. Total glutathione (oxidized and reduced) was determined using a modified Tietze method, known in the art, by measuring reduction of 5,5'-dithiobis-2-nitrobenzoic acid in a glutathione reductase-coupled assay.

Immunohistochemistry:

Formalin fixed tissues were treated with anti-NRF2 antibody (H-300, Santa Cruz Biotechnology, Santa Cruz, Calif.) at a dilution of 1:250 for 1 h and developed using horseradish peroxidase (DAKO).

Tumor Samples:

A total of 56 cases of lung tumor, including 40 paired lung tumors and adjacent normal tissues (frozen tissue) and 16 pleural fluid samples, were obtained from the Surgical Pathology archives of the Johns Hopkins Hospital, Baltimore, Md., USA, in accordance with the Institutional Review Board protocol and DNA was isolated using DNeasy Kit (Qiagen, Valencia Calif.). Details of the lung tumor samples are listed in Table 3.

PCR and Sequence Analysis:

Genomic sequence of Human KEAP1 was downloaded from NCBI human genome database. Primers for PCR amplification and sequencing of KEAP1 were designed using the Primer3 software available publicly on the internet, and synthesized by IDT DNA technologies (Coralville, Iowa). PCR amplification of DNA from early passage cell lines or primary tumors was carried out using EX TAQ Premix from Takara Mirus Biosciences (Madison, Wis.) and 10 pmol of each primer. PCR products were directly sequenced after purification using the Qiagen, QIAquick PCR purification kit (Qiagen, Valencia Calif.). Sequencing was carried out at the DNA sequencing core facility located at Johns Hopkins University. The sequence data was downloaded, assembled and analyzed to identify potential genetic alterations. All mutations were confirmed by sequencing in both directions. PCR products from samples showing deletion mutation were reamplified using high fidelity Taq polymerase (Applied Biosystems, Foster City Calif.), cloned into TOPO TA cloning vector (Invitrogen, Carlsbad Calif.) and 5 clones from each sample were sequenced. All deletions were present in at least 2 of the 5 clones sequenced. Exons harboring mutations were reamplified from the original DNA and sequenced. Chromatograms were analyzed by manual review. Sequences of all the primers used for amplification are in table-S5. The PCR cycling conditions were: 94° C. (3 minutes) for 1 cycle, 94° C. (30 seconds), 65° C. (45 seconds), 72° C. (1 minutes) for 35 cycles and a final extension of 72° C. (5 minutes).

Primer sequences used in the studies are listed in the chart below:

Microsattelite Based Loss of Heterozygosity Analysis.

Fluorescent LOH analysis using genomic DNA from matched normal and tumor lung tissues was performed using two novel microsattelite markers. Contig AC011461.5.1.100680 containing KEAP1 flanking sequences was downloaded from the Ensembl database, a publicly available resource. Two pairs of fluorescently labeled microsattelite primers flanking KEAP1 [KEAP-UM1 (CA17) and KEAP-DM1 (CA21)] were designed using Primer3 Software and synthesized by IDT DNA technologies (Coralville, Iowa). Briefly, each PCR was performed in a total volume of 10 μl containing 50 ng DNA, 10 mM Tris-HCl (pH 8.4), 50 mM KCl, 1.5 mM 0.01% gelatin, 200 μM dNTPs, 10 pmols of each primer, and 0.1 U Ampli Taq GOLD DNA polymerase (Applied Biosystems, Foster City Calif.). Cycling conditions were 94° C. for 10 minutes, then 25 cycles of 94° C. for 30 seconds, annealing temperature (66-67° C.) for 30 seconds, and 72° C. for 30 seconds, with a final extension of 72° C. for 20 minutes, in a MI Research tetrad PCR System (Bio-RAD, Hercules Calif.). The data were analyzed by the ABI Genescan and Genotyper software packages (Perkin Elmer, Wellsley Mass.) and allelic loss was scored. The sequence, allele size range for KEAP-DM1 and KEAP-UM1 were determined prior to their use in the analysis of the normal and tumor-matched lung cancer samples. In this system, a relative allele ratio of less than 0.6, which correlates with an allele loss of approximately 40%, was defined as loss of heterozygosity. The XLOH was confirmed at least twice for each marker.

Real Time RT-PCR

Total RNA was extracted from lung tissues and or cells using RNeasy kit (Qiagen, Valencia Calif.) and was quantified by UV absorbance spectrophotometry. The reverse transcription reaction was performed by using the Superscript First Strand Synthesis system (Invitrogen, Carlsbad Calif.) in a final volume of 20 μl containing 2 μg of total RNA, 100 ng of random hexamers, 1× reverse transcription buffer, 2.5 mM MgCl2, 1 mM dNTP, 10 units of RNaseOUT, 20 units of Superscript reverse transcriptase, and DEPC-treated water. Quantitative real time RT-PCR analyses of Human KEAP1, NRF2, GCLc, GCLm, GSR, PRDX1, GSTA3, GSTA2, NQO1, MRP1 and MRP2 were performed by using assay on demand primers and probe sets from Applied Biosystems. Assays were performed by using the ABI 7000 Taqman system (Applied Biosystems, Foster City Calif.). β-ACTIN was used for normalization.

| Primer Name | Forward Primer (5'-3') | Reverse Primer (5'-3') |
|---|---|---|
| KEAP1-UM1 | ACTGCATTTGGTCTTGCTCCTC | GCTTCTTCAAGCATCTGAATGTAGCTGTG |
| KEAP1-DM1 | TGAAGCTGAGGCACAGGAATA | ATGATGGACACTACACCTTCATCG |
| EXON2 | GCAAATGGATTCTGCTTCACCTACTT | TCAAACTGTGGAGACTACACCACCAT |
| EXON3 | CATCACAATGTACGCGGTTCCTATTA | GGCACAGAATCAAAGGTCACTGACTA |
| EXON4 | GATGAACCTGTCTCTTTAAGGGGGAA | GCAGAGAGAGAAGCTTGGACTCTATCAGAA |
| EXON5 | GTGAGAAGGGAGAGGAGAGAGGAAAGGTCT | TCCAGCTGGGCAACAGAGCGAGACCTTGTTT |
| EXON6 | AAGAGACTAAGGTTTTGCTATGTTGC | AGCTGAAACTGAAGGACAACTGTGTG |
| | Site Directed Mutagenesis Primers | |
| | Sense (5'-3') | Antisense (5'-3') |
| H1435 | CTGCGCCCCCATGAGCGTGCCCCTTAACCGCATC | GATGCGGTTAAGGGGCACGCTCATGGGGGCGCAG |
| A849 | GATCTACACCGCGGGCTGCTACTTCCGACAGT | ACTGTCGGAAGTAGCAGCCCGCGGTGTAGATC |

Plasmid Construction:

Plasmid encoding human KEAP1 cDNA in pCMV6-XL5 was purchased from Origene (Origene Technologies Inc., Rockville Md.). The cDNA clone was digested with NotI, and insert was further cloned in pUb6 vector (Invitrogen, Carlsbad Calif.). Glycine to Serine and Leucine to Arginine mutations were introduced into the KEAP1 expression vector (pCMV6-XL5) by using site Directed mutagenesis kit (Stratagene, La Jolla Calif.).

Cell Culture and Reagents:

HBE4, NL20, A549, H460, H1435, and H838 cells were purchased from American Type Culture Collection (ATCC) and cultured under recommended conditions. BEAS2B cells were provided by Dr. Sekhar Reddy (Johns Hopkins University, Baltimore, Md.). H292, H23, H358, H1299, H1993, and H1395 cells were kindly provided by Dr James G Herman (Johns Hopkins University, Baltimore, Md.). All transfections were carried out using Lipofectamine 2000 (Invitrogen, Carlsbad Calif.).

Generation of Stable Transfectants:

H838 cells overexpressing ARE (Antioxidant Response Element) luciferase reporter plasmid were obtained by transfecting H838 cells with 3 μg of NQO1-ARE reporter plasmid and 0.3 μg of pUB6 empty vector (Invitrogen, Carlsbad Calif.). Stable transfectants were selected using Blasticidin at a concentration of 6 μg/ml. Stable clones were expanded and screened for the expression of ARE luciferase. H460 and A549 cells stably expressing WT-KEAP1 were obtained by transfecting the cells with 3 μg of pUB6-Keap1 or pUB6 alone and selecting for Blasticidin resistance at a concentration of 6 μg/ml and 10 μg/ml for H460 and A549 cells, respectively. Cells were selected for Blasticidin resistance for two weeks. Overexpression of KEAP1 was confirmed by Real time RT-PCR.

Luciferase Assay:

H838 cells stably expressing NQO1 ARE luicferase were seeded onto a 24-well dish at a density of $0.2\times10^6$ cells/ml for 12 h before transfection. WT-KEAP1 cDNA constructs along with the mutant cDNA constructs (G333C and 1413R) were transfected into the cells along with pRL-TK plasmid expressing Renilla luciferase as a transfection control. Twenty-four hours after transfection, cells were lysed and both firefly and Renilla luciferase activities were measured with a Dual-Luciferase reporter assay system (Promega, Madison Wis.).

siRNA Duplex Screening and Transfection:

The siRNA sequence targeting NRF2 corresponds to the coding region 1903-1921 nt (5'-GTAAGAAGCCAGATGTTAATT-3'; SEQ ID NO:27) in the NRF2 cDNA. The NRF2 siRNA duplex with the following sense and antisense sequences was used: 5'-GUAAGAAGCCAGAUGUUAAdUdU (sense; SEQ ID NO:50) and dUdUCAUUCUUCGGUCUACAATT-5' (antisense; SEQ ID NO:28). To confirm the specificity of the inhibition, the siCONTROL nontargeting siRNA 1 (NS siRNA; 5'UAGCGACUAAACACAUCAAUU 3'; SEQ ID NO:29) with microarray-defined signature was used as a negative control. All of the siRNA duplexes were synthesized by Dharmacon Research, Inc. (Lafayette). Cells in the exponential growth phase were plated at a density of $0.2\times10^6$ cells/ml, grown for 12 h, and transfected twice at an interval of 48 h with 50 nM siRNA duplexes using Lipofectamine 2000 and OPTI-MEMI reduced serum medium (Invitrogen, Carlsbad Calif.) according to the manufacturer's recommendations. Concentrations of siRNAs were chosen on the basis of dose-response studies.

Drug Accumulation Assay:

Cells transfected with NRF2 siRNA and NS siRNA were seeded at a density of $0.3\times10^6$ cells/ml in 6-well plates. After 12 h, growth medium was aspirated and replaced with 1.5 ml of RPMI 1640 containing 0.2 μM of [$^3$H]Etoposide (646 mCi/mmol; Moravek Biochemicals) and [$^{14}$C] Carboplatin (53 mCi/mmol; Amersham Biosciences,). Cells were incubated with radiolabeled drug for indicated period of time and then cooled on ice, washed four times with ice-cold PBS, and solubilized with 1.0 ml of 1% SDS. The radioactivity in each sample was determined by scintillation counting. Results are presented as means±SD. Comparisons were made by paired t-test and $P<0.05$ was considered statistically significant.

MTT Cell Viability Assay:

Cells were transfected with 50 nM siRNAs two times with a 48 h interval and, 24 h after the second transfection, cells were plated at a density of 7,500 cells/well in 180 μl of growth media in 96-well plates. After 6 hrs incubation at 37° C., cells were treated with various concentrations of drugs dissolved in a volume of 20 μl. After 96 h, drug cytotoxicity was evaluated by using a 3-(4,5-dimethylthiazol-2-yl)-2,5-diphenyl tetrazolium bromide (MTT; Sigma, St. Louis Mo.) reduction conversion assay. Forty μl of MTT at 5 mg/ml was added to each well, and incubation was continued for 4 h. The formazan crystals resulting from mitochondrial enzymatic activity on MTT substrate were solubilized with 200 μl of Dimethyl Sulfoxide, and absorbance was measured at 570 nm by using a SpectraMAX microplate reader (Molecular Devices, Union City Calif.). Cell survival was expressed as absorbance relative to that of untreated controls. Results are presented as means±SD. Comparisons were made by paired t-test and $P<0.05$ was considered statistically significant.

In Vitro Transcription/Translation (IVTT):

Human KEAP1 and NRF2 cDNA were in vitro transcribed and translated using In vitro transcription/translation reactions. These were performed in T7 TNT reticulocyte lysate (Promega, Madison Wis.) following the supplier's instructions.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

LITERATURE CITED

Singleton et al., Dictionary of Microbiology and Molecular Biology (2nd ed. 1994).

Stein C A et al. 1993. Antisense oligonucleotides as therapeutic agents—is the bullet really magical? *Science* 261, 1004-1012.

Delihas N, Rokita S E, Zheng P. 1997 *Nat. Biotechnol.* 157 51-3. Review

Schmajuk G, Sierakowska H, Kole R. 1999. Antisense oligonucleotides with different backbones. Modification of splicing pathways and efficacy of uptake. *J. Biol. Chem.* 274, 21783 21789.
Aboul-Fadl T. 2005. Antisense oligonucleotides: the state of the art. *Curr Med Chem.* 12, 2193-214. Review.
K. D. Tew, *Cancer Res* 54, 4313 (1994).
Bass et al. *Nature* 411:428-429 (2001).
Elbashir et al. *Nature* 411:494-498 (2001).
Zamore et al. *Cell* 101:25-33 (2000).
Tuschl *Chembiochem* 2: 239-245 (2001).
Hutvagner et al. *Curr Opin Genet Dev* 12:225-232 (2002).
Hannon *Nature* 418:244-251 (2002).
Brummelkamp et al. *Science* 296:550-553, 2002.
Paddison et al. *Genes & Devel.* 16:948-958, 2002.
Paul et al. *Nature Biotechnol.* 20:505-508, 2002.
Sui et al. *Proc. Natl. Acad. Sci. USA* 99:5515-5520, 2002.
Yu et al. *Proc. Natl. Acad. Sci. USA* 99:6047-6052, 2002.
Miyagishi et al. *Nature Biotechnol.* 20:497-500, 2002.
Lee et al. *Nature Biotechnol.* 20:500-505 2002
Haseloff et al. *Nature* 334:585-591. 1988
Hampel and Tritz, *Biochemistry,* 28:4929, 1989, and Hampel et al., *Nucleic Acids Research,* 18: 299, 1990.
Cayouette et al., *Human Gene Therapy* 8:423-430, 1997.
Kido et al., *Current Eye Research* 15:833-844, 1996.
Bloomer et al., *Journal of Virology* 71:6641-6649, 1997.
Naldini et al., *Science* 272:263-267, 1996.
Miyoshi et al., *Proc. Natl. Acad. Sci. U.S.A.* 94:10319, 1997
Miller, *Human Gene Therapy* 15-14, 1990.
Friedman, *Science* 244:1275-1281, 1989.
Eglitis et al., *BioTechniques* 6:608-614, 1988.
Tolstoshev et al., *Current Opinion in Biotechnology* 1:55-61, 1990.
Sharp, *The Lancet* 337:1277-1278, 1991.
Cornetta et al., *Nucleic Acid Research and Molecular Biology* 36:311-322, 1987.
Anderson, *Science* 226:401-409, 1984.
Moen, *Blood Cells* 17:407-416, 1991.
Miller et al., Biotechnology 7:980-990, 1989.
Le Gal La Salle et al., *Science* 259:988-990, 1993.
Johnson, *Chest* 107:77 S-83S, 1995
Rosenberg et al., N. Engl. J. Med 323:370, 1990
Feigner et al., *Proc. Natl. Acad. Sci. U.S.A.* 84:7413, 1987.
Ono et al., *Neuroscience Letters* 17:259, 1990.
Brigham et al., *Am. J. Med. Sci.* 298:278, 1989.
Staubinger et al., *Methods in Enzymology* 101:512, 1983).
Suda et al., Endocr. Rev., 1999, 20, 345-357.
S. Yla-Hertttuala and J. F. Martin, The Lancet 355, 213-222, 2000
Wu et al., *Journal of Biological Chemistry* 263:14621, 1988.
Wu et al., *Journal of Biological Chemistry* 264:16985, 1989).
Wolff et al., *Science* 247:1465, 1990
Remington: The Science and Practice of Pharmacy" Ed. A. R. Gennaro, Lippincourt Williams & Wilkins, Philadelphia, Pa., 2000.
Zuckermann, R. N. et al., *J. Med. Chem.* 37:2678-85, 1994
Lam, *Anticancer Drug Des.* 12:145, 1997
DeWitt et al., *Proc. Natl. Acad. Sci. U.S.A.* 90:6909, 1993.
Erb et al., *Proc. Natl. Acad. Sci. USA* 91:11422, 1994.
Zuckermann et al., *J. Med. Chem.* 37:2678, 1994.
Cho et al., *Science* 261:1303, 1993.
Carrell et al., *Angew. Chem. Int. Ed. Engl.* 33:2059, 1994.
Carell et al., *Angew. Chem. Int. Ed. Engl.* 33:2061, 1994.
Gallop et al., *J. Med. Chem.* 37:1233, 1994.
Houghten, *Biotechniques* 13:412-421, 1992.
Lam, *Nature* 354:82-84, 1991.
Fodor, *Nature* 364:555-556, 1993)
Cull et al., *Proc Natl Acad Sci USA* 89:1865-1869, 1992). Scott and Smith, *Science* 249:386-390, 1990.
Devlin, *Science* 249:404-406, 1990.
Cwirla et al. *Proc. Natl. Acad. Sci.* 87:6378-6382, 1990.
Felici, *J. Mol. Biol.* 222:301-310, 1991;
Kittler et al. (*Nature.* 432 (7020):1036-40, 2004.
Miyamoto et al. (*Nature* 416(6883):865-9, 2002.
Ruefli-Brasse et al., Science 302(5650):1581-4, 2003.
Gu et al., Science 302 (5644):445-9, 2003.
Crouch et al. J. Immunol. Metli. 160, 81-8.
Kangas et al. Med. Biol. 62, 338-43, 1984.
Lundin et al., Meth. Enzymol. 133: 27-42, 1986.
Petty et al. *Comparison of J. Biolum. Chemilum.* 10: 29-34, 1995.
Cree et al. *AntiCancer Drugs* 6: 398-404, 1995.
Barltrop, Bioorg. & Med. Chem. Lett. 1: 611, 1991.
Cory et al., *Cancer Comm.* 3: 207-12, 1991.
Paull J. *Heterocyclic Chem.* 25: 911, 1988.
Lockhart, et al. *Nat. Biotech.* 14:1675-1680, 1996.
Schena, et al. *Proc. Natl. Acad. Sci.* 93:10614-10619, 1996.
Ge *Nucleic Acids Res.* 28:e3.i-e3.vii, 2000.
MacBeath et al., *Science* 289:1760-1763, 2000.
Zhu et al. *Nature Genet.* 26:283-289.
Cancer Principles and Practice of Oncology by V. T. Devita and S. Hellman (editors), 6th edition (Feb. 15, 2001), Lippincott Williams & Wilkins Publishers
L. C. Young, B. G. Campling, S. P. Cole, R. G. Deeley, J. H. Gerlach, *Clin Cancer Res* 7,1798 (2001).
Y. Soini et al., *Cancer* 92, 2911 (2001).
M. M. Gottesman, *Annu Rev Med* 53, 615 (2002).
T. Rangasamy et al., *J Clin Invest* 114, 1248 (2004).
R. K. Thimmulappa et al., *Cancer Res* 62, 5196 (2002).
H. S. So et al., *Cell Death Differ* (2006).
A. Hayashi, H. Suzuki, K. Itob, M. Yamamoto, Y. Sugiyama, *Biochem Biophys Res Commun* 310, 824 (2003).
V. Vollrath, A. M. Wielandt, M. Iruretagoyena, J. Chianale, *Biochem J* (2006).
T. Nguyen, P. J. Sherratt, C. B. Pickett, *Annu Rev Pharmacol Toxicol* 43,233 (2003).
Y. Aoki et al., *Toxicol Appl Pharmacol* 173, 154 (2001).
H. Y. Cho et al., *Am J Respir Cell Mol Biol* 26, 175 (2002).
R. K. Thimmulappa et al., *J Clin Invest* 116 (2006).
T. Rangasamy et al., *J Exp Med* 202, 47 (2005).
M. Ramos-Gomez et al., *Proc Natl Acad Sci USA* 98, 3410 (2001).
A. Kobayashi et al., *Mol Cell Biol* 24, 7130 (2004).
D. D. Zhang, S. C. Lo, J. V. Cross, D. J. Templeton, M. Hannink, *Mol Cell Biol* 24, 10941 (2004).
J. Adams, R. Kelso, L. Cooley, *Trends Cell Biol* 10, 17 (2000).
N. Wakabayashi et al., *Proc Natl Acad Sci USA* 101, 2040 (2004).
N. Wakabayashi et al., *Nat Genet.* 35, 238 (2003).
R. N. Karapetian et al., *Mol Cell Biol* 25, 1089 (2005).
L. Girard, S. Zochbauer-Muller, A. K. Virmani, A. F. Gazdar, J. D. Minna, *Cancer Res* 60, 4894 (2000).
A. G. Knudson, Jr., *Cancer Res* 45, 1437 (1985).
P. D'Arpa, L. F. Liu, *Biochim Biophys Acta* 989, 163 (1989).
C. M. Rudin et al., *Cancer Res* 63, 312 (2003).
D. Hamilton, G. Batist, *Curr Oncol Rep* 6, 116 (2004).
R. N. Karapetian et al., *Mol Cell Biol* 25, 1089 (2005).
L. Girard, S. Zochbauer-Muller, A. K. Virmani, A. F. Gazdar, J. D. Minna, *Cancer Res* 60, 4894 (2000).
C. M. Rudin et al., *Cancer Res* 63, 312 (2003).
D. Hamilton, G. Batist, *Curr Oncol Rep* 6; 116 (2004).

What is claimed is:

1. A method for diagnosing a subject as having chemoresistant non-small cell lung cancer, the method comprising obtaining a biological sample from the subject, detecting a mutation in Keap1 and detecting an increase in the expression of Nrf2, GSH, GST, and NQO1 polypeptide marker molecules in the sample relative to the expression of—Nrf2, GSH, GST, and NQO1 polypeptide markers in a normal tissue, thereby diagnosing the subject as having chemoresistant non-small cell lung cancer.

2. A method for diagnosing a subject as having non-small cell lung cancer, the method comprising obtaining a biological sample from the subject, detecting a mutation in Keap1 and detecting an increase in the levels of Nrf2, GSH, GST, and NQO1 polypeptide markers in the biological sample relative to the levels present in a normal control tissue, thereby diagnosing the subject as having non-small cell lung cancer.

3. The method of claim 2, wherein the levels of the markers are determined in an immunological assay.

4. The method of claim 3, wherein the immunological assay is an enzyme-linked immunosorbent assay (ELISA), radioimmune assay (RIA), Western blot assay, slot blot assay, or microchip assay.

* * * * *